US010752598B2

(12) United States Patent
Or et al.

(10) Patent No.: US 10,752,598 B2
(45) Date of Patent: Aug. 25, 2020

(54) ARYLDIAZEPINE DERIVATIVES AS RSV INHIBITORS

(71) Applicant: Enanta Pharmaceuticals, Inc., Watertown, MA (US)

(72) Inventors: Yat Sun Or, Watertown, MA (US); Thomas P. Blaisdell, Brighton, MA (US); Brian C. Shook, Holliston, MA (US); In Jong Kim, Lexington, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/001,247

(22) Filed: Jun. 6, 2018

(65) Prior Publication Data
US 2018/0354912 A1 Dec. 13, 2018

Related U.S. Application Data

(60) Provisional application No. 62/516,274, filed on Jun. 7, 2017.

(51) Int. Cl.
| | |
|---|---|
| *C07D 413/14* | (2006.01) |
| *C07D 417/14* | (2006.01) |
| *C07D 413/12* | (2006.01) |
| *C07D 243/14* | (2006.01) |
| *A61K 45/06* | (2006.01) |
| *A61P 31/14* | (2006.01) |

(52) U.S. Cl.
CPC ............ *C07D 243/14* (2013.01); *A61K 45/06* (2013.01); *A61P 31/14* (2018.01); *C07D 413/12* (2013.01); *C07D 413/14* (2013.01); *C07D 417/14* (2013.01)

(58) Field of Classification Search
CPC ... C07D 413/14; C07D 417/14; C07D 413/12
See application file for complete search history.

(56) References Cited

U.S. PATENT DOCUMENTS

| | | | | |
|---|---|---|---|---|
| 4,010,153 | A | 3/1977 | Kajfez et al. | |
| 4,511,510 | A | 4/1985 | Mauri | |
| 4,988,692 | A * | 1/1991 | Gasc | C07D 243/12 514/221 |
| 5,571,809 | A | 11/1996 | Hargrave et al. | |
| 5,637,697 | A * | 6/1997 | Finch | C07D 243/12 540/518 |
| 5,646,140 | A * | 7/1997 | Sugg | C07K 5/0202 514/221 |
| 5,681,833 | A | 10/1997 | Castro et al. | |
| 7,582,624 | B2 | 9/2009 | Carter et al. | |
| 8,999,969 | B2 | 4/2015 | Mackman et al. | |
| 9,732,098 | B2 | 8/2017 | Hunt et al. | |
| 9,957,281 | B2 | 5/2018 | Shook et al. | |
| 10,358,441 | B2 | 7/2019 | Kim et al. | |
| 10,398,706 | B2 | 9/2019 | Shook et al. | |

| | | |
|---|---|---|
| 2006/0040923 | A1 | 2/2006 Carter et al. |
| 2006/0083741 | A1 | 4/2006 Hoffman et al. |
| 2007/0142403 | A1 | 6/2007 Powell et al. |
| 2007/0185094 | A1 | 8/2007 Lattmann et al. |
| 2007/0185096 | A1 | 8/2007 Powell et al. |
| 2007/0293482 | A1 | 12/2007 Dowdell et al. |
| 2008/0139536 | A1 | 6/2008 Dowdell et al. |
| 2009/0274655 | A1 | 11/2009 Grimes et al. |
| 2010/0015063 | A1 | 1/2010 Carter et al. |
| 2012/0196846 | A1 | 8/2012 Mackman et al. |
| 2014/0038947 | A1 | 2/2014 Glick et al. |
| 2014/0100365 | A1 | 4/2014 Gavai et al. |
| 2015/0065504 | A1 | 3/2015 Wang et al. |
| 2015/0299210 | A1 | 10/2015 Bailey et al. |
| 2017/0022221 | A1 | 1/2017 Blaisdell et al. |

(Continued)

FOREIGN PATENT DOCUMENTS

| | | |
|---|---|---|
| EP | 0703222 A1 | 3/1996 |
| WO | 9308175 A1 | 4/1993 |

(Continued)

OTHER PUBLICATIONS

Aquino et al. J. Med. Chem. 1996, 39, 562-569 (Year: 1996).*
Xiong, et al., "Discover of a potent respiratory syncytial virus RNA polymerase inhibitor," Bioorganic & Chemistry Medicinal Letters, 23:6789-6793, 2013.
Carter, et al., "1,4-Benzodiazepines as Inhibitors of Respiratory Syncytial Virus," Journal of Medicinal Chemistry, 49:2311-2319, 2006.
Henderson, et al., "1,4-Benzodiazepines as Inhibitors of Respiratory Syncytial Virus", The Identification of a Clinical Candidate, Journal of Medicinal Chemistry, 50:1685-1692, 2007.
Albright, et al. (Document No. 130:153583) retrieved from STN; entered in STN on Feb. 16, 1999.

(Continued)

*Primary Examiner* — Matthew P Coughlin
(74) *Attorney, Agent, or Firm* — Elmore Patent Law Group, P.C.; Carolyn Elmore; Edgar Harlan

(57) ABSTRACT

The present invention discloses compounds of Formula (I), and pharmaceutically acceptable salts, esters, or prodrugs thereof:

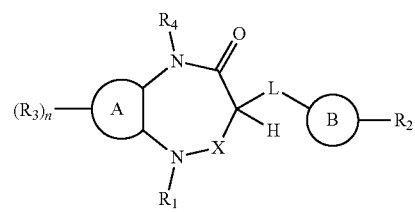

(I)

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

18 Claims, No Drawings

(56) References Cited

U.S. PATENT DOCUMENTS

| | | |
|---|---|---|
| 2017/0226127 A1 | 8/2017 | Estrada et al. |
| 2017/0226129 A1 | 8/2017 | Yu et al. |
| 2017/0305935 A1 | 10/2017 | Hunt et al. |
| 2017/0355717 A1 | 12/2017 | Hunt et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |
| 2019/0092791 A1 | 3/2019 | Hunt et al. |
| 2019/0152968 A1 | 5/2019 | Blaisdell et al. |
| 2019/0177283 A1 | 6/2019 | Hague |
| 2019/0192535 A1 | 6/2019 | Shook et al. |
| 2019/0315766 A1 | 10/2019 | Yu et al. |

FOREIGN PATENT DOCUMENTS

| | | |
|---|---|---|
| WO | 9426718 A1 | 11/1994 |
| WO | 2004026843 A1 | 4/2004 |
| WO | 2004106310 A1 | 12/2004 |
| WO | 2005089769 A1 | 9/2005 |
| WO | 2005090319 A1 | 9/2005 |
| WO | 2006081389 A1 | 8/2006 |
| WO | 2010103306 A1 | 9/2010 |
| WO | 2011005842 A1 | 1/2011 |
| WO | 2011151651 A1 | 6/2011 |
| WO | 2014047369 A1 | 3/2014 |
| WO | 2014125444 A1 | 8/2014 |
| WO | 2014184350 A1 | 11/2014 |
| WO | 2016022464 A1 | 2/2016 |
| WO | 2016055791 A1 | 4/2016 |
| WO | 2016055792 A1 | 4/2016 |
| WO | 2016097761 A1 | 6/2016 |
| WO | 2016166546 A1 | 10/2016 |
| WO | 2017015449 A1 | 1/2017 |
| WO | 2017123884 A1 | 7/2017 |
| WO | 2017175000 A1 | 10/2017 |

OTHER PUBLICATIONS

Albright, et al. (Document No. 129:54301) retrieved from STN; entered in STN on Jun. 17, 1998.
Lee, et al. (Document No. 140:69941) retrieved from STN; entered in STN on Jul. 8, 2003.
Zheng, et al. (Document No. 161:399872) retrieved from STN; entered in STN on Jul. 23, 2014.
Wang, et al. (Document No. 160:385666) retrieved from STN; entered in STN on Feb. 27, 2014.
Xiong, et al. (Document No. 160:101182) retrieved from STN; entered in STN on Nov. 12, 2013.
Heeney, et al. (Document No. 153:359062) retrieved from STN; entered in STN on Sep. 2, 2010.
Andrzej, et al. (Document No. 144:274313) retrieved from STN; entered in STN on Mar. 3, 2006.
Peesapati, et al. (Document No. 120:244848) retrieved from STN; entered in STN on May 14, 1994.
Respiratory syncytial virus (RSV) [online], retrieved from from internet on Jun. 25, 2017.; URL http://www.mayoclinic.org/diseases-condiitons/respiratory-syncytial-virus/basics/prevention.
Kim, In Jong, et al., U.S. Appl. No. 16/023,363, filed Jun. 29, 2018.
Kim, In Jong, et al., U.S. Appl. No. 16/023,422, filed Jun. 29, 2018.
Pubchem-CID: 10595203, p. 3, Fig, Oct. 25, 2006, 1-9.
Fordyce, et al., "Discovery of novel benzothienoazepine derivatives as potent inhibitors of respiratory syncytial virus", Bioorganic & Medicinal Chemistry Letters, 27, 2017, 2201-2206.
Offel, M. et al., "Synthesis of Substituted 3-Anilino-5-phenyl-I,3-dihydro-2H-I, 4-benzodiazepine-2-ones and their Evaluation as Cholecystokinin-Ligands", Archiv Der Pharmazie, vol. 339, No. 4, Apr. 1, 2006, 163-173.
Setoi, Hiroyuki et al., "Preparation of heterocyclylbenzamide derivatives as vasopressin antagonists", Document No. 131:116236, retrieved from STN; entered in STN on Aug. 6, 1999, Aug. 6, 1999.
STN Registry database entry: CAS RN 1348849-53-5 (Entered STN: Dec. 5, 2011) (Year: 2011).
STN Registry database entry: CAS RN 1349533-81-8 (Entered STN: Dec. 6, 2011) (Year: 2011).
STN Registry database entry: CAS RN 1350148-32-1 (Entered STN: Dec. 7, 2011) (Year: 2011).
Armstrong, et al., "An Efficient Asymmetric Synthesis of (R)-3-Amino-2,3,4,5-tetrahydro-1H-[1]benzazepine-2-one", Tetrahedron Letters, 35(20), 1994, 3239-3242.
Chapman, Joanna et al., "RSV604, a Novel Inhibitor of Respiratory Syncytial Virus Replication", Antimicrobial Agents and Chemotherapy, vol. 51, No. 9, 2007, 3346-3353.
Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.
Olszewska, Wieslawa et al., "Emerging drugs for respiratory syncytial virus infection", Expert Opin. Emerg. Drugs (2009), 14(2), 207-217.
Perron, Michel et al., "GS-5806 Inhibits a Broad Range of Respiratory Syncytial Virus Clinical Isolates by Blocking the Virus-Cell Fusion Process", Antimicrobial Agents and Chemotherapy, 2016, 60(3), 1264-1273.
Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.
Sudo, Kenji et al., "YM-53403, a unique anti-respiratory syncytial virus agent with a novel mechanism of action", Antiviral Research, 2005, vol. 65, 2005, 125-131.

* cited by examiner

ARYLDIAZEPINE DERIVATIVES AS RSV INHIBITORS

RELATED APPLICATIONS

This application claims the benefit of U.S. Provisional Application No. 62/516,274, filed on Jun. 7, 2017. The entire teachings of the above application are incorporated herein by reference.

TECHNICAL FIELD

The present invention relates generally to compounds and pharmaceutical compositions useful as Respiratory Syncytial Virus (RSV) inhibitors. Specifically, the present invention relates to aryldiazepine derivatives that can inhibit RSV activities and for treating RSV infection.

BACKGROUND OF THE INVENTION

Human respiratory syncytial virus (HRSV) is a negative-sense, single stranded, RNA paramyxovirus (K M. Empey, et al., *Rev. Anti-Infective Agents*, 2010, 50 (1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immuno-suppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, and *J. Med. Chem.* 2015, 58, 1630-1643. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2013/242525 and *J. Med. Chem.* 2015, 58, 1862-1878.

There is a need for the development of effective treatments for HRSV. The present invention has identified these novel compounds and their inhibitory activity against HRSV. The invention includes methods to prepare the compounds as well as methods of using these compounds to treat disease.

SUMMARY OF THE INVENTION

The present invention provides compounds represented by Formula (I), and pharmaceutically acceptable salts, esters and prodrugs thereof:

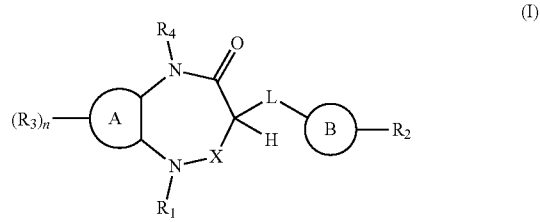

(I)

wherein:
A is aryl or heteroaryl, each of which, when possible, is optionally substituted with one or more substituents which are not $R_3$;
B is optionally substituted heteroaryl or optionally substituted aryl;
L is —NH—, —NHC(O)—, or —NHC(O)NH—;
X is —$CH_2$—, or —C(O)—;
$R_1$ is optionally substituted heteroaryl or optionally substituted aryl;
$R_2$ is absent or selected from the group consisting of:
  1) Optionally substituted —$C_1$-$C_8$ alkyl;
  2) Optionally substituted —$C_2$-$C_8$ alkenyl;
  3) Optionally substituted —$C_2$-$C_8$ alkynyl;
  4) Optionally substituted —$C_1$-$C_8$ alkoxy;
  5) Optionally substituted aryloxy;
  6) Optionally substituted —$C_3$-$C_{12}$ cycloalkyl;
  7) Optionally substituted —$C_3$-$C_{12}$ cycloalkenyl;
  8) Optionally substituted 3- to 12-membered heterocycloalkyl;
  9) Optionally substituted aryl;
  10) Optionally substituted arylalkyl;
  11) Optionally substituted heteroaryl;
  12) Optionally substituted heteroarylalkyl;
  13) —$NR_{13}R_{14}$;
  14) —CO—$NR_{13}R_{14}$; and
  15) —$SO_2$—$NR_{13}R_{14}$;
preferably, $R_2$ is optionally substituted —$C_3$-$C_{12}$ cycloalkyl; optionally substituted —$C_3$-$C_{12}$ cycloalkenyl; optionally substituted 3- to 12-membered heterocycloalkyl; optionally substituted aryl; or optionally substituted heteroaryl;
each $R_3$ is the same or different and independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —$NHC_1$-$C_8$ alkyl, optionally substituted —S—(—$C_1$-$C_8$ alkyl), optionally substituted —$SO_2$—(—$C_1$-$C_8$ alkyl), -optionally substituted —$SO_2$—NH—(—$C_1$-$C_8$ alkyl), optionally substituted —NH—$SO_2$—(—$C_1$-$C_8$ alkyl), —$CO_2R_{12}$, —$NR_{13}R_{14}$, and —CO—$NR_{13}R_{14}$;
$R_{12}$ is independently selected from the group consisting of:
  1) Optionally substituted —$C_1$-$C_8$ alkyl;
  2) Optionally substituted —$C_2$-$C_8$ alkenyl;
  3) Optionally substituted —$C_2$-$C_8$ alkynyl;

4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;
7) Optionally substituted aryl; and
8) Optionally substituted heteroaryl;

$R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted —$C_3$-$C_8$ cycloalkenyl; optionally substituted 3- to 12-membered heterocycloalkyl, optionally substituted aryl; optionally substituted heteroaryl; optionally substituted —$C_1$-$C_8$-alkoxy, —$C(O)R_{12}$, —$S(O)_2R_{12}$, and —$S(O)_2NHR_{12}$; alternatively, $R_{13}$ and $R_{14}$ are taken together with the nitrogen atom to which they are attached to form an optionally substituted heterocyclic ring;

$R_4$ is selected from hydrogen and optionally substituted —$C_1$-$C_8$ alkyl, preferably $R_4$ is hydrogen or $CH_3$; and n is 0 to k, wherein k is the total number of CH and NH groups in the heteroaryl group A when A is unsubstituted; preferably, n is 0, 1 or 2; more preferably n is 0. Most preferably, A is unsubstituted.

Each preferred group stated above can be taken in combination with one, any or all other preferred groups.

DETAILED DESCRIPTION OF THE INVENTION

In one embodiment of the present invention is a compound represented by Formula (I) as described above, or a pharmaceutically acceptable salt, ester or prodrug thereof.

The carbon atom at position 3 of the aryldiazepine ring system of the compounds of the invention is chiral. Thus, compounds of the invention can have the stereochemistry depicted in Formula (Ia) or (Ib):

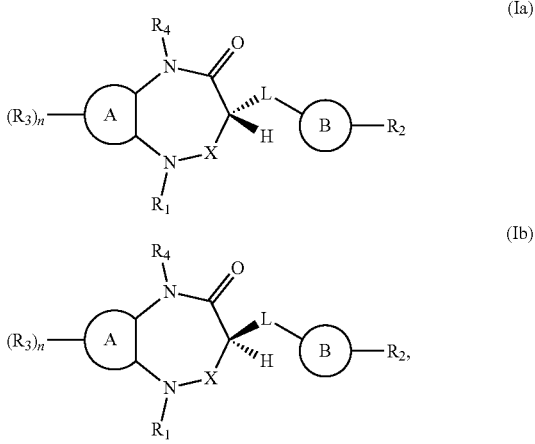

wherein $R_1$, $R_2$, $R_3$, $R_4$, A, B, L, X, and n are as previously defined. A composition of the invention can comprise a compound of the invention as a racemic mixture of Formula Ia and Formula Ib, a pure enantiomer of either Formula Ia or Formula Ib, or an excess of one enantiomer over the other. For example, the composition can comprise the compound in an enantiomeric excess of at least 5, 10, 20, 30, 40, 50, 60, 70, 80 or 90%. In one embodiment, the enantiomeric excess is at least 95%. In compounds of the invention having two or more chiral atoms, such compounds can be present in a composition as a pure stereoisomer or a mixture of stereoisomers, such as a racemic mixture or a mixture of diastereomers. In one embodiment, a composition of the invention comprises a racemic mixture, a single stereoisomer or enantiomers with an enantiomeric excess of at least 5, 10, 20, 30, 40, 50, 60, 70, 80, 90 or 95%.

In a preferred embodiment, a compound of the invention is represented by Formula (Ib). Compositions of the invention preferably comprise a substantially pure compound of Formula (Ib), or a mixture of a compound of Formula (Ib) and the corresponding compound of Formula (Ia), with an enantiomeric excess of the compound of Formula (Ib) as discussed above.

In certain embodiments, the present invention relates to compounds of Formula (I), and pharmaceutically acceptable salts thereof, wherein A is optionally substituted aryl. Preferably A is optionally substituted phenyl, more preferably A is unsubstituted phenyl.

In certain embodiments, the present invention relates to compounds of Formula (I), and pharmaceutically acceptable salts thereof, wherein A is optionally substituted heteroaryl. Preferably A is optionally substituted heteroaryl. More preferably A is optionally substituted monocyclic 5-membered heteroaryl. In one embodiment, A is a five-membered heteroaryl group containing sulfur.

In another embodiment, the present invention relates to compounds of Formula (I), and pharmaceutically acceptable salts thereof, wherein A is derived from one of the following by removal of the hydrogen atoms from two adjacent carbon atoms:

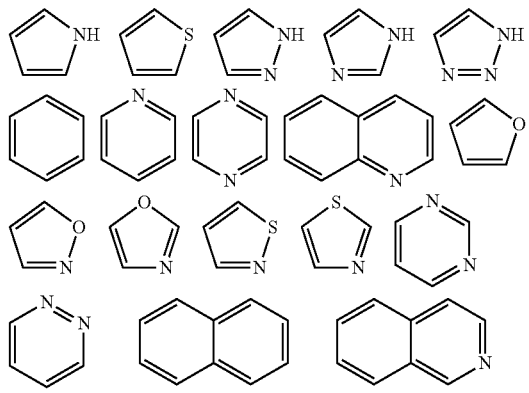

each of which, when possible, is optionally substituted with one or more substituents which are not $R_3$.

In certain embodiments, the present invention relates to compounds of Formula (I), and pharmaceutically acceptable salts thereof, wherein each $R_3$ is independently halo, optionally substituted —$C_1$-$C_4$-alkyl, or —$C_1$-$C_4$-alkoxy. In certain embodiments, the present invention relates to compounds of Formula (I), and pharmaceutically acceptable salts thereof, wherein each $R_3$ is independently —F, —$CH_3$, —$CF_3$, —$OCF_3$, —CN, —$SO_2Me$, or —$CH_2N(CH_3)_2$. In certain embodiments, the present invention relates to compounds of Formula (I), and pharmaceutically acceptable salts thereof, wherein n is 0 to 3, 0 to 2, 1 or 0. More preferably, n is 0.

In certain embodiments, the present invention relates to compounds of Formula (I), and pharmaceutically acceptable salts thereof, wherein $R_1$ is optionally substituted aryl. In certain embodiments, the present invention relates to compounds of Formula (I), and pharmaceutically acceptable salts thereof, wherein $R_1$ is optionally substituted heteroaryl.

In certain embodiments, the present invention relates to compounds of Formula (I), and pharmaceutically acceptable salts thereof, wherein $R_1$ is phenyl optionally substituted with one to three substituents selected from the group consisting of halo, —$CF_3$, —$OCF_3$, —$CH_3$, —$SO_2Me$, and cyano. Preferably, $R_1$ is unsubstituted phenyl.

In one embodiment, the present invention relates to compounds of Formula (I), and pharmaceutically acceptable salts thereof, wherein $R_4$ is optionally substituted methyl. In another embodiment, the present invention relates to compounds of Formula (I), and pharmaceutically acceptable salts thereof, wherein $R_4$ is hydrogen.

In one embodiment, the present invention relates to compounds of Formula (I), and pharmaceutically acceptable salts thereof, wherein X is —$CH_2$—. In another embodiment, the present invention relates to compounds of Formula (I), and pharmaceutically acceptable salts thereof, wherein X is —C(O)—.

In one embodiment, the present invention relates to compounds of Formula (I), and pharmaceutically acceptable salts thereof, wherein L is —NH—. In another embodiment, the present invention relates to compounds of Formula (I), and pharmaceutically acceptable salts thereof, wherein L is —NHC(O)—. In another embodiment, the present invention relates to compounds of Formula (I), and pharmaceutically acceptable salts thereof, wherein L is —NHC(O)NH—.

In certain embodiments, the present invention relates to compounds of Formula (I), and pharmaceutically acceptable salts thereof, wherein B is optionally substituted aryl, optionally substituted heteroaryl. Preferably B is optionally substituted monocyclic 5-membered heteroaryl, a monocyclic 6-membered heteroaryl or an 8-10-membered fused heteroaryl. In one embodiment, B is a five-membered nitrogen containing heteroaryl group.

In another embodiment, the present invention relates to compounds of Formula (I), and pharmaceutically acceptables salt thereof, wherein B is derived from one of the following by removal of two hydrogen atoms:

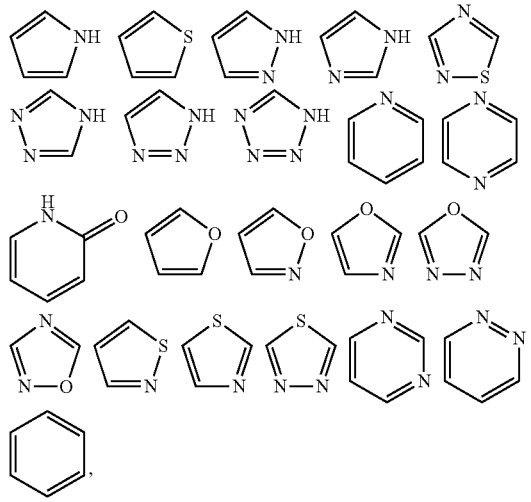

wherein each of the above is optionally substituted when possible.

In certain embodiments, B is selected from, but not limited to, the groups set forth below, where one of the indicated valences is the point of attachment of the heteroaryl group to $R_2$ and the other is the point of attachment to L. Each of these groups is optionally additionally substituted when possible. The atom of B which connects to L is a carbon atom. The atom of B that connects to $R_2$ is a carbon atom or, when possible, a nitrogen atom:

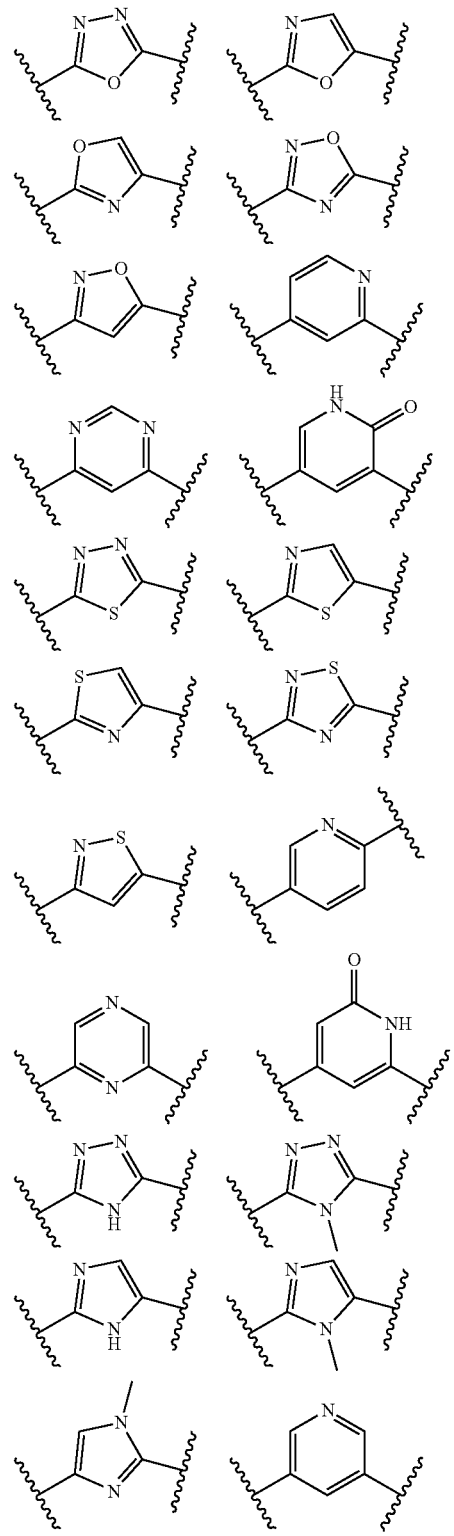

-continued

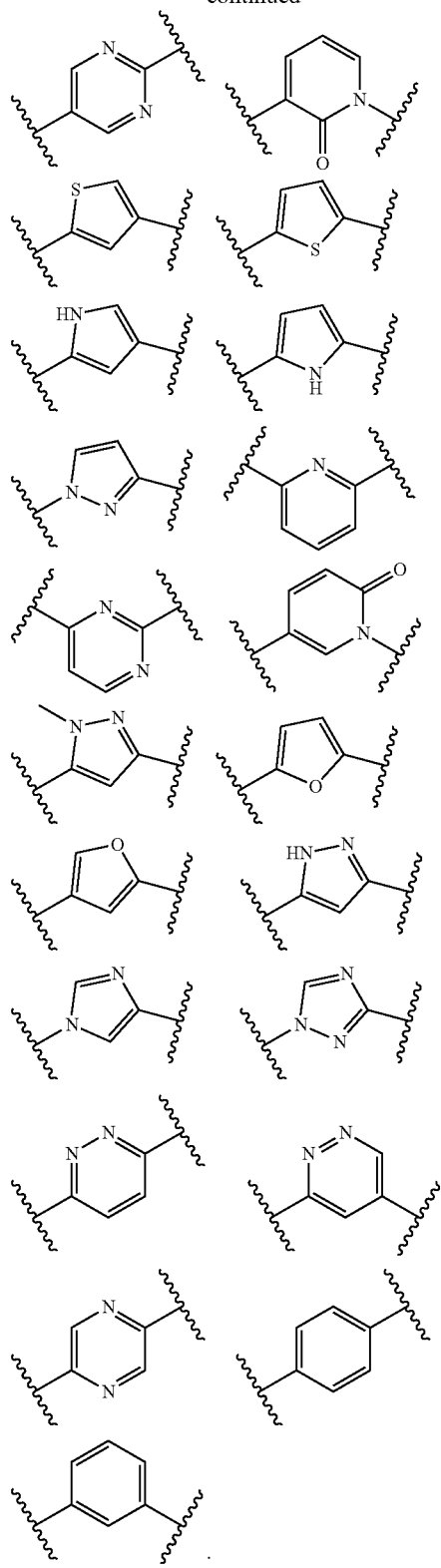

In another particular embodiment, the present invention relates to compounds of Formula (I), and pharmaceutically acceptable salts thereof, wherein B is derived from a fused bicyclic group selected from one of the following by removal of two hydrogen atoms.

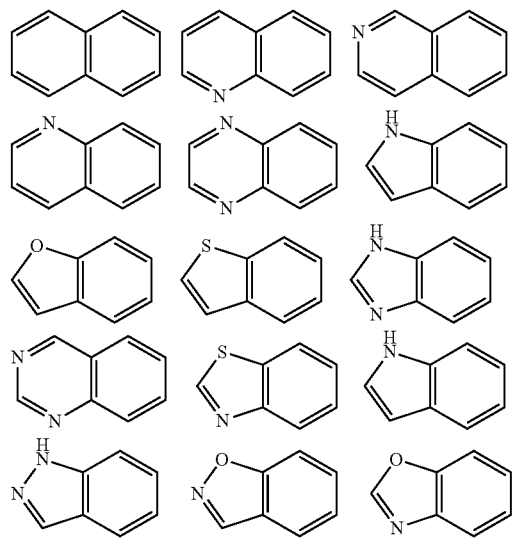

In certain embodiments, the present invention relates to compounds of Formula (I), and pharmaceutically acceptable salts thereof, where B is selected from the groups set forth below,

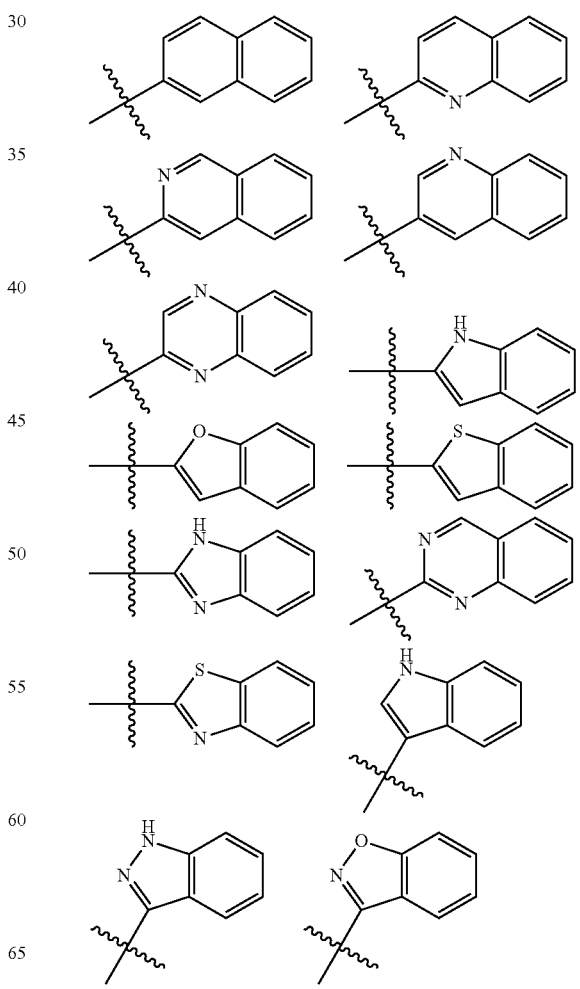

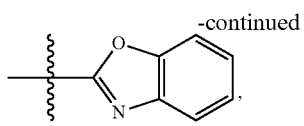

wherein the point of attachment to L is indicated and $R_2$ is attached to any other available ring position. In one embodiment, $R_2$ is attached to an atom of the benzo ring. When B is naphthyl, $R_2$ and L are preferably attached to carbon atoms from different rings. Each of the above shown groups is optionally substituted, and preferably the optional substituents are independently selected from halo, —$CH_3$, —$CF_3$, —$OCF_3$, —CN, —$NH_2$, —OH, —$CH_2N(CH_3)_2$, —C(O)$CH_3$, —NH—($C_1$-$C_6$)alkyl, —$SO_2$—($C_1$-$C_6$)alkyl, —$SO_2$—NH—($C_1$-$C_6$)alkyl, —NH—$SO_2$—($C_1$-$C_6$)alkyl, and —$C_1$-$C_8$-alkoxy. Preferably, in addition to $R_2$, there are 0, 1, 2 or 3 substituents, more preferably 0, 1 or 2 substituents, and most preferably 0 or 1 substituent.

In certain embodiments of the compounds of the invention, $R_2$ is absent.

In certain embodiments, $R_2$ is an optionally substituted aryl, heteroaryl, 3- to 12-membered heterocycloalkyl, —$C_3$-$C_{12}$-cycloalkyl, —$C_3$-$C_{12}$ cycloalkenyl, aryl-O—, heteroaryl-O, aryl-$C_1$-$C_4$-alkyl or heteroaryl-$C_1$-$C_4$-alkyl. In certain embodiments, $R_2$ is phenyl, naphthyl, 5-membered heteroaryl or 6-membered heteroaryl, each of which is optionally substituted. In certain embodiments, $R_2$ is a 5- or 6-membered heteroaryl fused with a 6-membered aryl, heteroaryl, carbocyclic or heterocyclic ring, such as a benzo-fused-5- or 6-membered heteroaryl or a pyrido-fused 5- or 6-membered heteroaryl.

In certain embodiments of the compounds of the invention, $R_2$ is a group derived from one of the following by removal of one hydrogen atom from a ring atom:

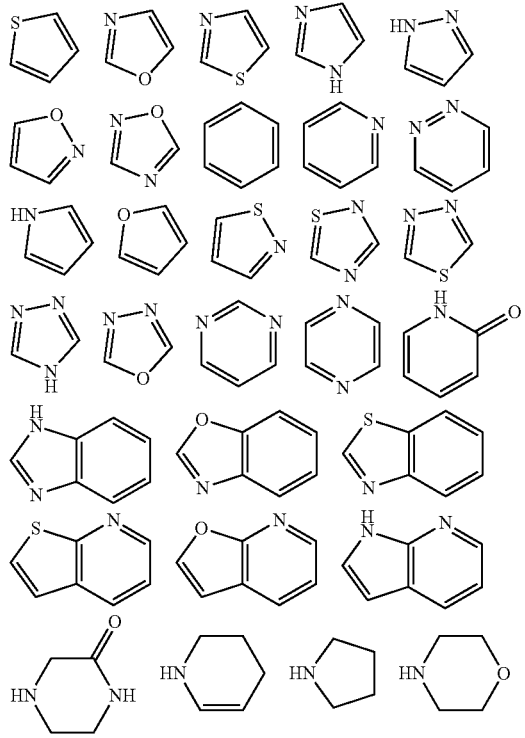

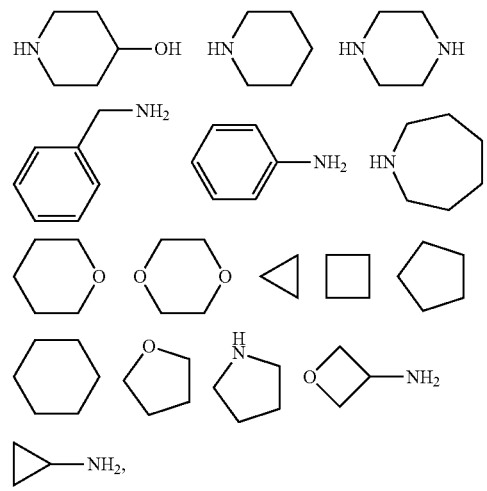

wherein each of the above shown is optionally substituted when possible.

In certain embodiments, $R_2$ is selected from the groups shown below, each of which is optionally substituted,

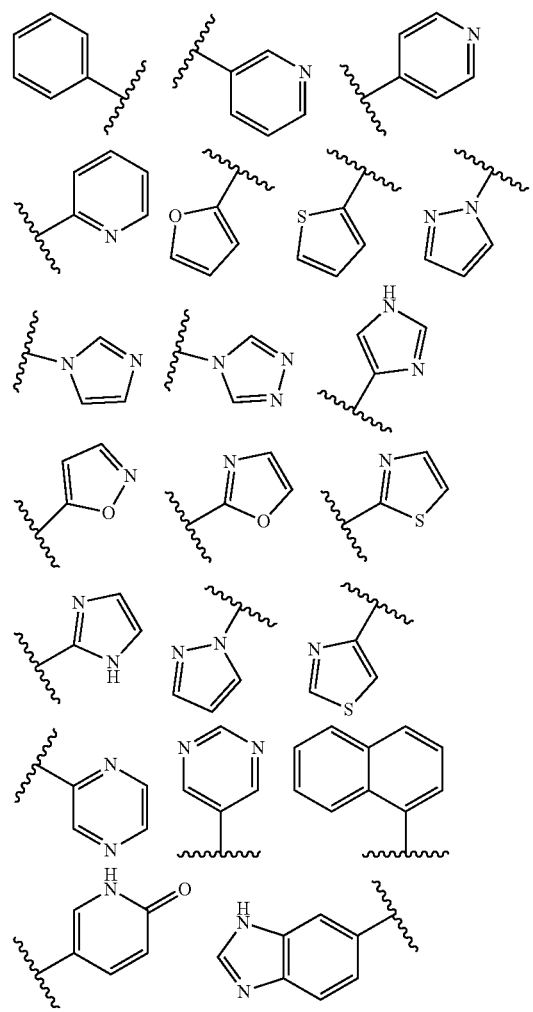

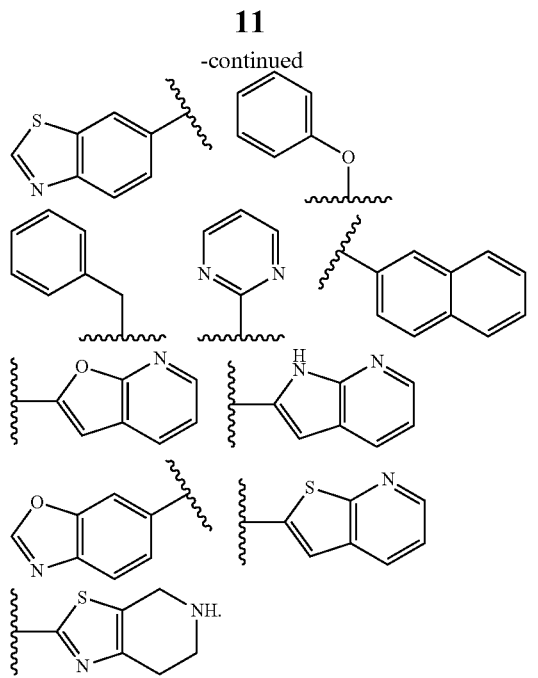

In certain embodiments, $R_2$ is optionally substituted with one or more substituents independently selected from halo, $-CH_3$, $-CF_3$, $-OCF_3$, $-CN$, $-NH_2$, $-OH$, $-CH_2N(CH_3)_2$, $-C(O)CH_3$, optionally substituted $-NH-(C_1-C_6)$alkyl, optionally substituted $-NH-(C_1-C_6)$alkyl-$(C_1-C_6)$alkoxy, optionally substituted $-SO_2-(C_1-C_6)$alkyl, optionally substituted $-SO_2-NH-(C_1-C_6)$alkyl, optionally substituted $-NH-SO_2-(C_1-C_6)$alkyl, optionally substituted 3- to 12-membered heterocycloalkyl, optionally substituted aryl, optionally substituted heteroaryl, optionally substituted $-C_1-C_8$-alkyl, optionally substituted $-C_1-C_8$-alkenyl, optionally substituted $-C_3-C_8$-cycloalkyl, optionally substituted $-C_3-C_8$-cycloalkenyl, and optionally substituted $-C_1-C_8$-alkoxy. In certain embodiments, there are 0 to 4, 0 to 3, 0 to 2, 1 or 0 substituents. Preferably, there are 0 to 2 substituents and more preferably, 0 or 1 substituent. More preferably optionally substituted groups can be more than one. In this embodiment, $R_2$ is optionally substituted with one or more aryl, heteroaryl, 3- to 12-membered heterocycloalkyl, $C_3-C_{12}$-cycloalkyl, $C_3-C_{12}$ cycloalkenyl, aryl-O—, heteroaryl-O, aryl-$C_1$-$C_4$-alkyl or heteroaryl-$C_1$-$C_4$-alkyl, as described above. In this embodiment, $R_2$ is preferably optionally substituted aryl, heteroaryl, 3- to 12-membered heterocycloalkyl, $C_3$-$C_{12}$-cycloalkyl, or $C_3$-$C_{12}$ cycloalkenyl.

In certain embodiments of the compounds of the invention, $R_2$ is selected from the groups below, each of which is optionally substituted:

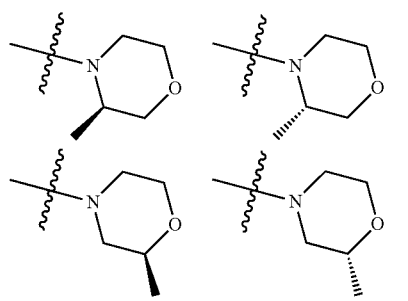

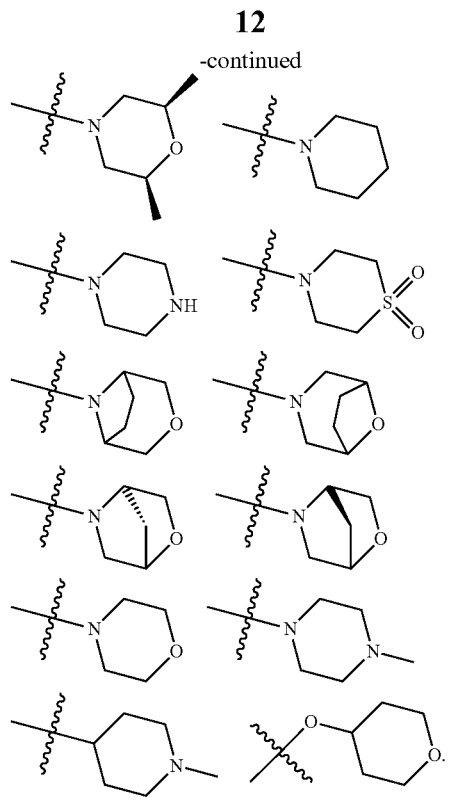

In certain embodiments of the compounds of the invention, $R_2$ is selected from the groups below, each of which is optionally substituted:

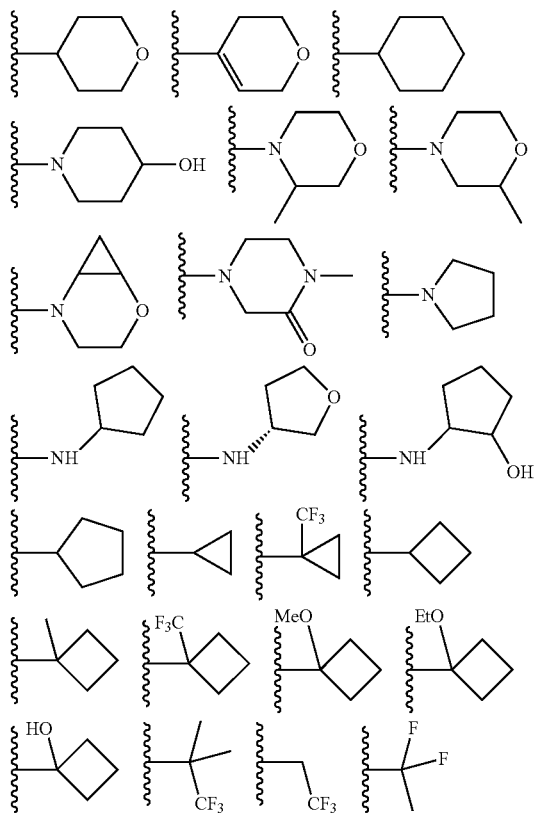

-continued

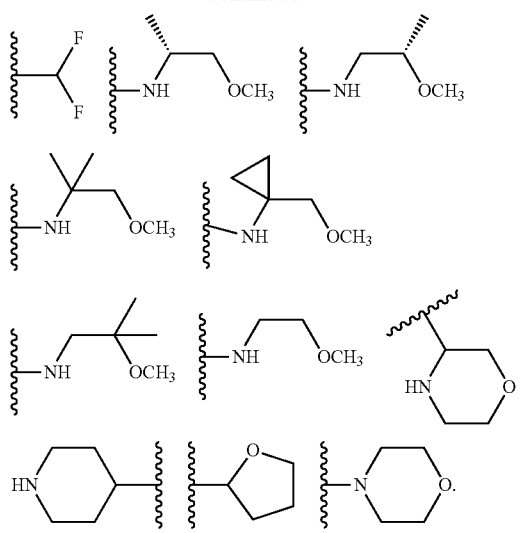

In certain embodiments of the compounds of the invention, R₂ is optionally substituted with one or more substituents independently selected from the groups below, each of which can be optionally substituted further:

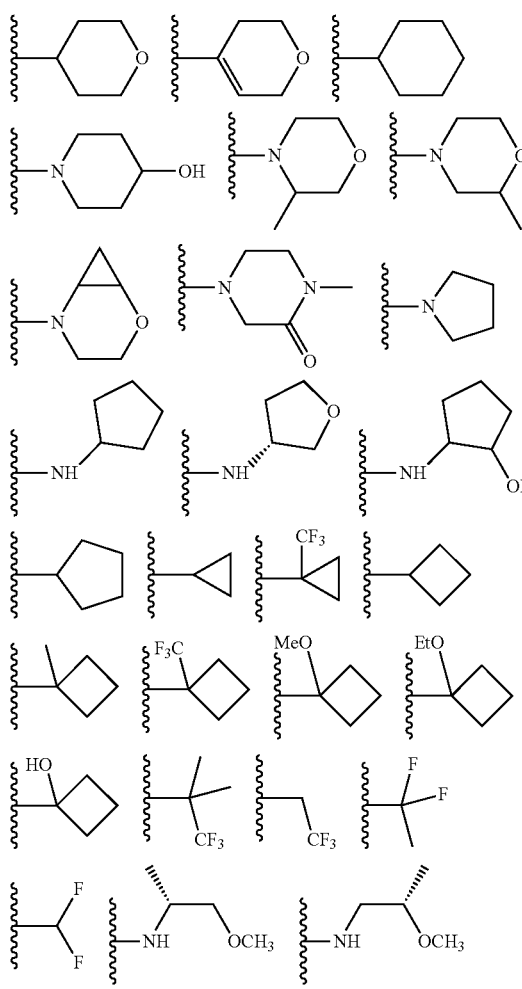

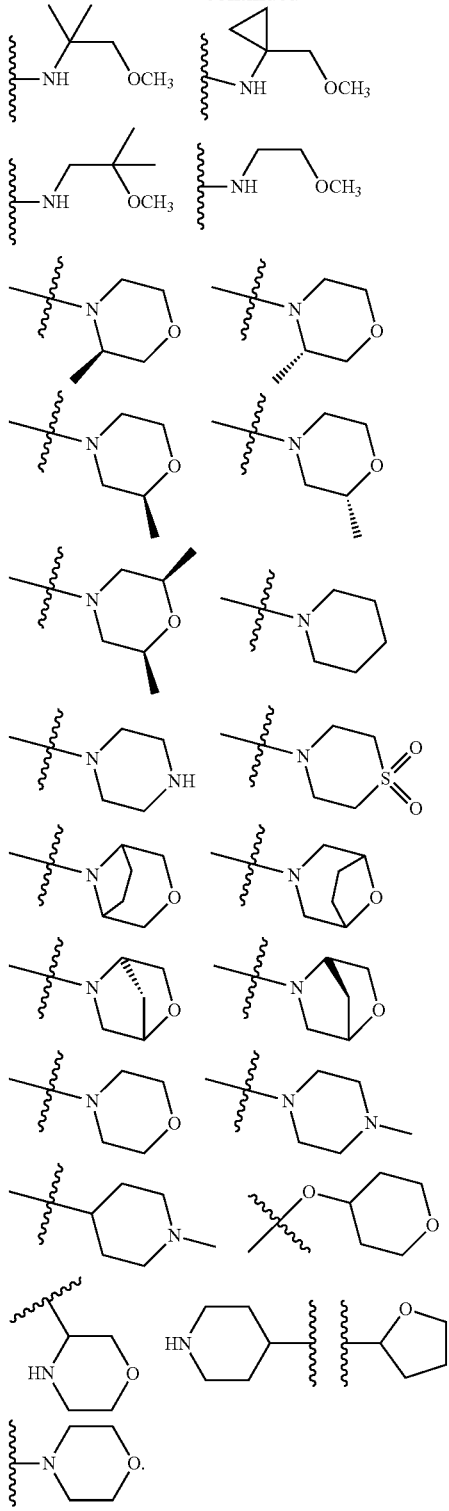

In certain embodiments of the compounds of the invention, A is a optionally substituted monocyclic 5-membered heteroaryl; R₁ is optionally substituted aryl; R₂ is optionally substituted aryl or optionally substituted heteroaryl; R₄ is methyl or hydrogen; and L is —NH—. Preferably A is optionally substituted thiophene. Preferably R₁ is optionally substituted phenyl. Preferably B is optionally substituted triazole, optionally substituted oxadiazolyl, optionally substituted oxazolyl, or optionally substituted thiadiazolyl.

In certain embodiments of the compounds of the invention, A is optionally substituted aryl; $R_1$ is optionally substituted aryl; $R_2$ is optionally substituted aryl or optionally substituted heteroaryl; $R_4$ is methyl or hydrogen; and L is —NH—. Preferably A is optionally substituted phenyl. Preferably $R_1$ is optionally substituted phenyl. Preferably B is optionally substituted triazolyl, optionally substituted oxadiazolyl, optionally substituted oxazolyl, or optionally substituted thiadiazolyl.

In another embodiment, the invention provides a compound represented by one of Formulas (II-1)~(II-3), (IIa-1)~(IIa-3), and (IIb-1)~(IIb-3) or a pharmaceutically acceptable salt, ester or prodrug thereof:

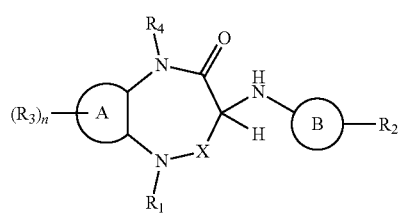
(II-1)

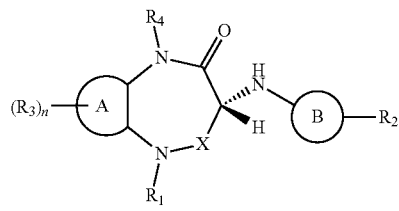
(IIa-1)

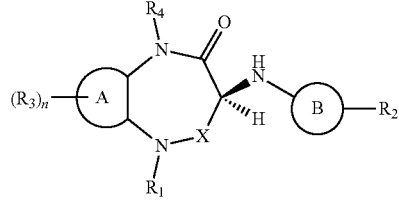
(IIb-1)

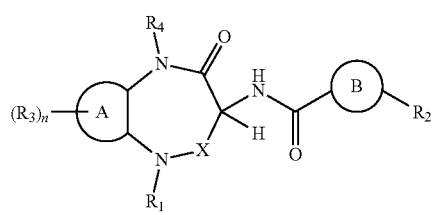
(II-2)

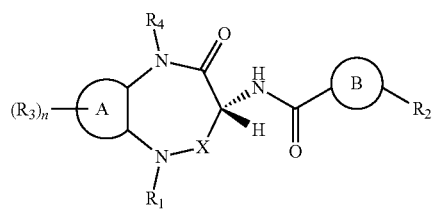
(IIa-2)

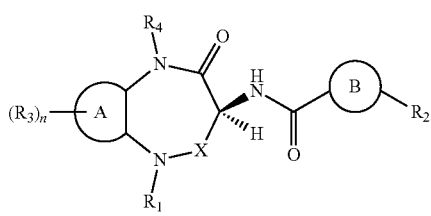
(IIb-2)

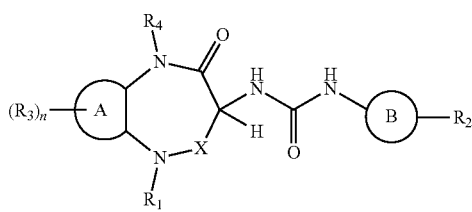
(II-3)

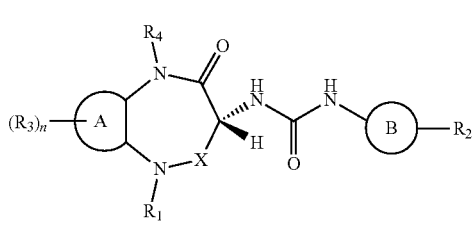
(IIa-3)

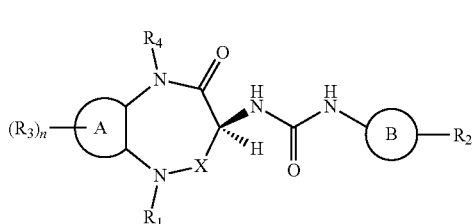
(IIb-3)

wherein $R_1$, $R_2$, $R_3$, $R_4$, A, B, X, and n are as previously defined.

In another embodiment, the invention provides a compound represented by one of Formulas (III-1) and (III-2), or a pharmaceutically acceptable salt, ester or prodrug thereof:

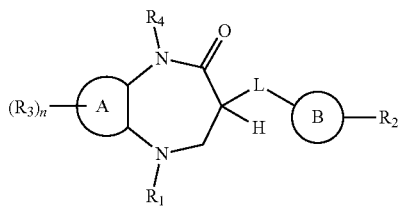
(III-1)

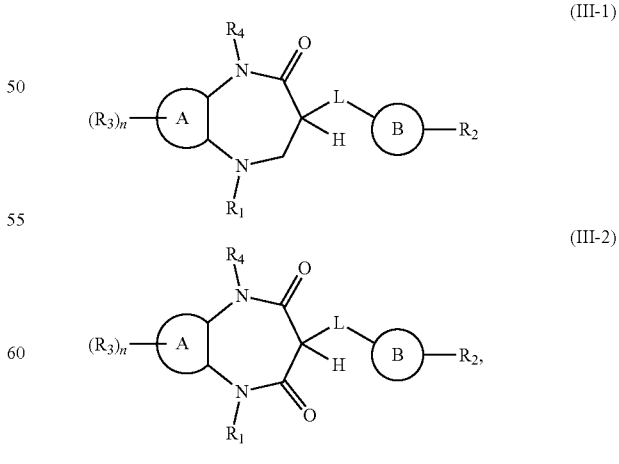
(III-2)

wherein $R_1$, $R_2$, $R_3$, $R_4$, A, B, L, and n are as previously defined.

In another embodiment, the invention provides a compound represented by one of Formulas (IV-1) and (IV-2), or a pharmaceutically acceptable salt, ester or prodrug thereof:

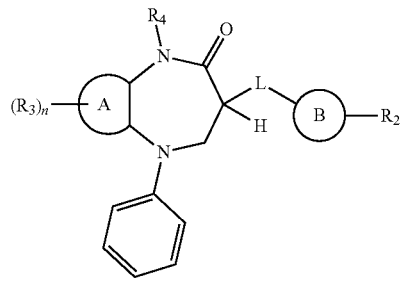

(IV-1)

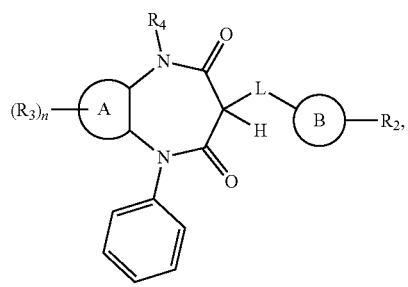

(IV-2)

wherein $R_2$, $R_3$, $R_4$, A, B, L, and n are as previously defined.

In another embodiment, the invention provides a compound represented by one of Formulas (V-1) and (V-2), or a pharmaceutically acceptable salt, ester or prodrug thereof:

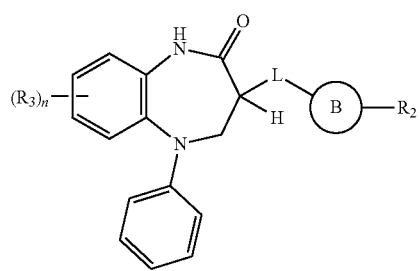

(V-1)

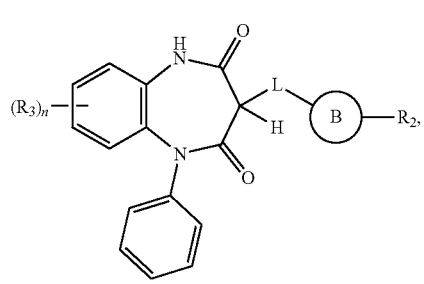

(V-2)

wherein $R_2$, $R_3$, B, L, and n are as previously defined.

In another embodiment, the invention provides a compound represented by one of Formulas (VI-1)~(VI-8), (VIa-1)~(VIa-8), and (VIb-1)~(VIb-8), or a pharmaceutically acceptable salt, ester or prodrug thereof:

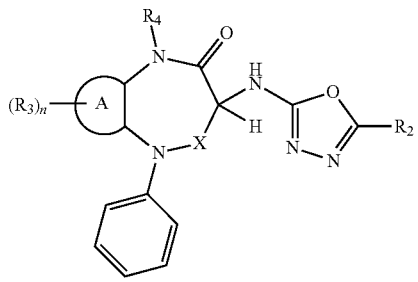

VI-1

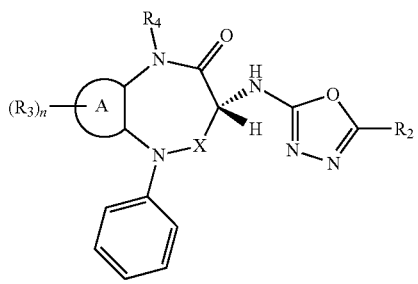

VIa-1

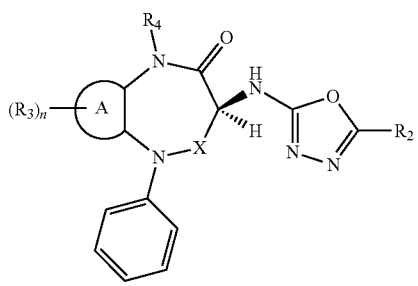

VIb-1

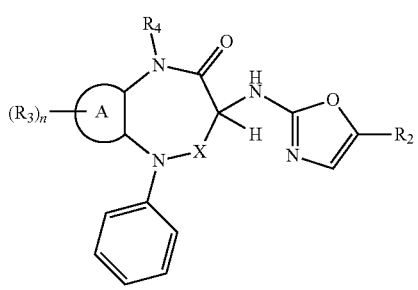

VI-2

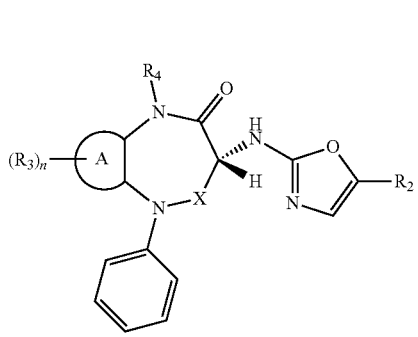

VIa-2

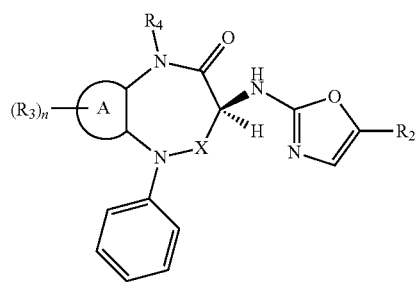
VIb-2
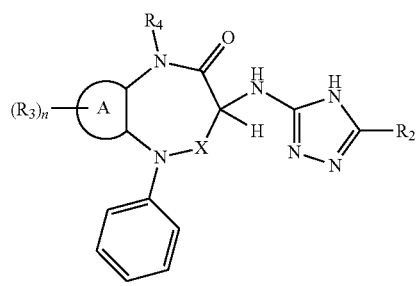
VI-3
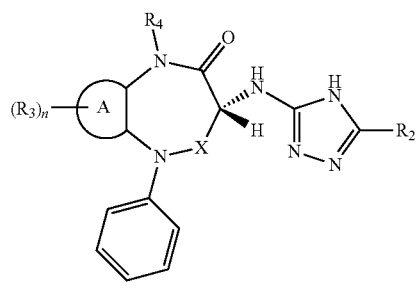
VIa-3
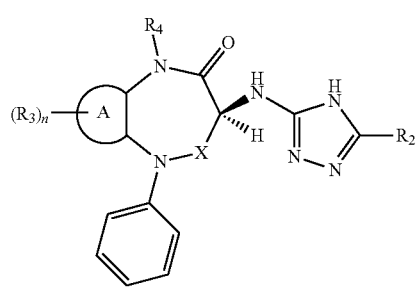
VIb-3
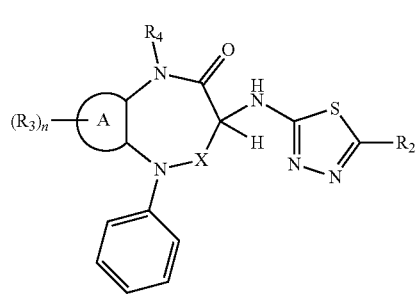
VI-4
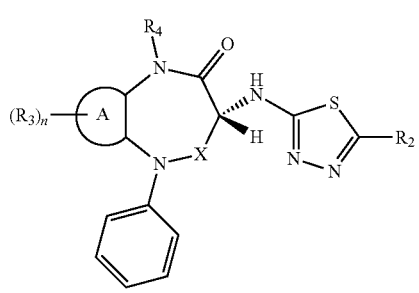
VIa-4
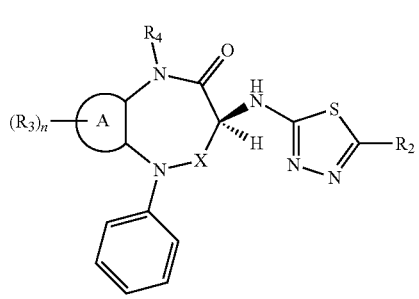
VIb-4
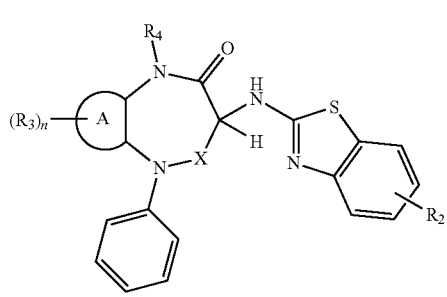
VI-5
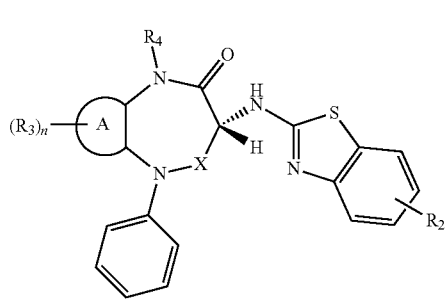
VIa-5
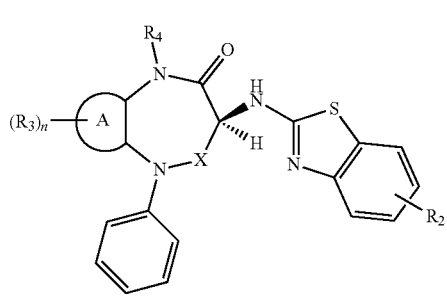
VIb-5

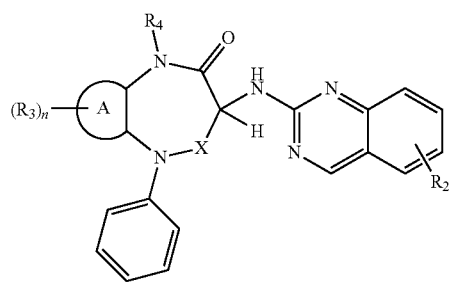
VI-6
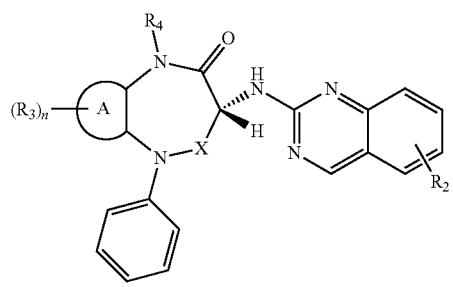
VIa-6
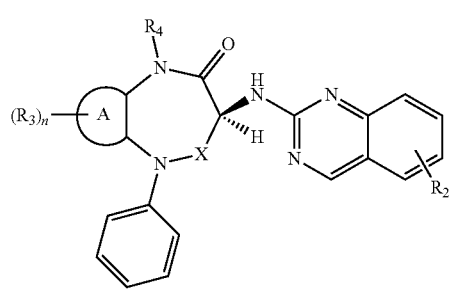
VIb-6
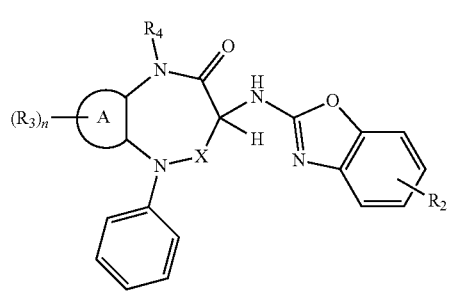
VI-7
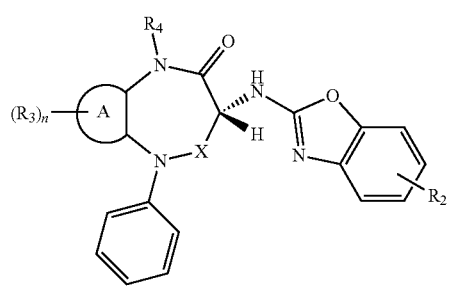
VIa-7
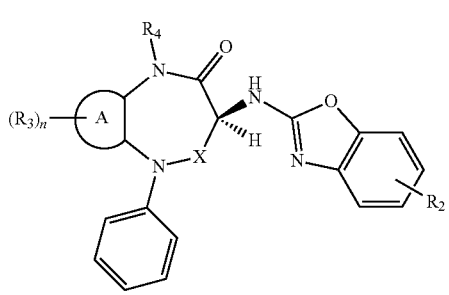
VIb-7
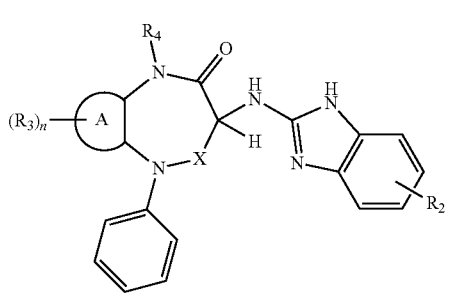
VI-8
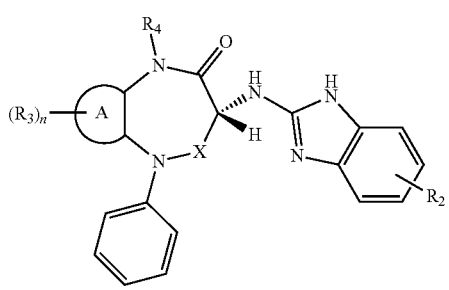
VIa-8
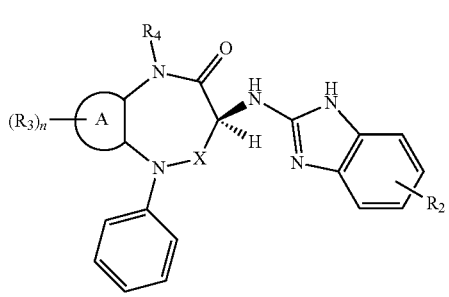
VIb-8
wherein $R_2$, $R_3$, $R_4$, A, X, and n are as previously defined. Preferably $R_4$ is hydrogen, A is phenyl, and n is 0.

In another embodiment of the invention is a compound represented by one of Formulas (VII-1)~(VII-8), (VIIa-1)~(VIIa-8), and (VIIb-1)~(VIIb-8) or a pharmaceutically acceptable salt, ester or prodrug thereof:
VII-1
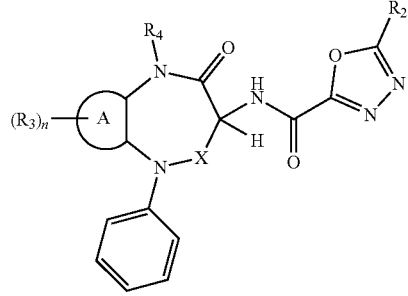
VIIa-1
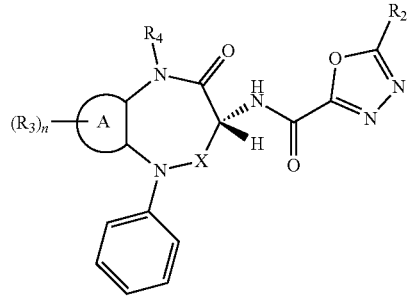
VIIb-1
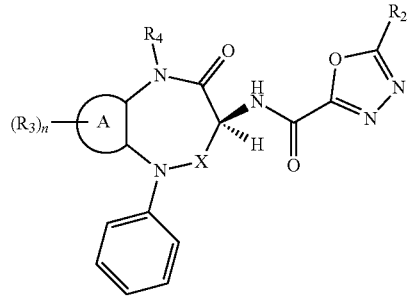
VII-2
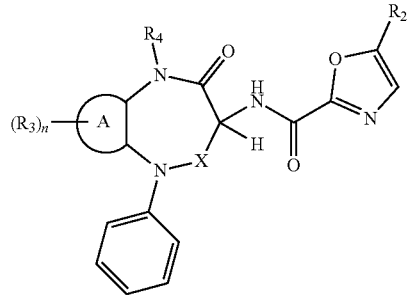
VIIa-2
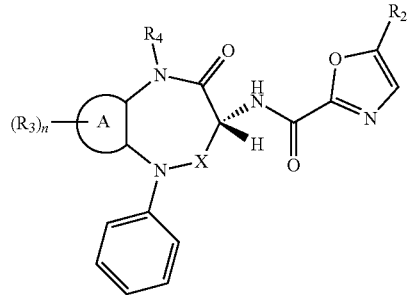
VIIb-2
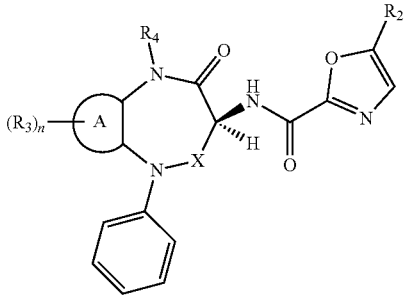
VII-3
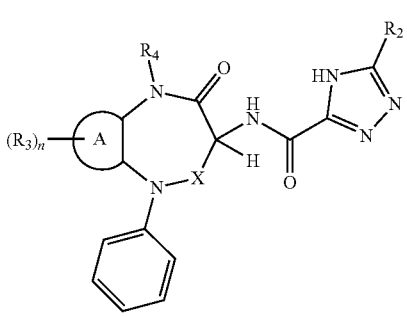
VIIa-3
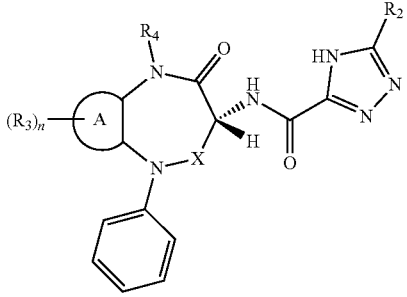
VIIb-3
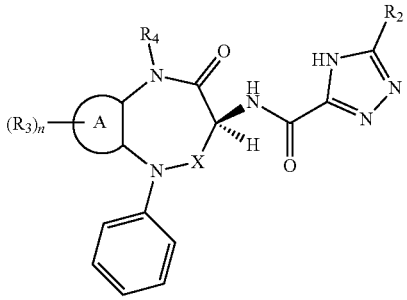
VII-4
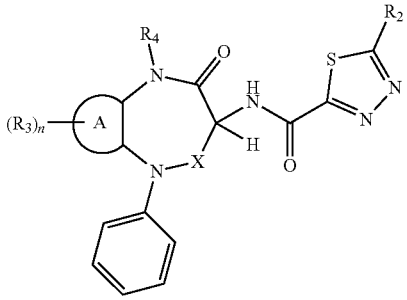

-continued
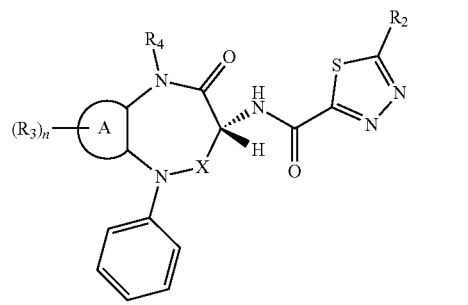
VIIa-4
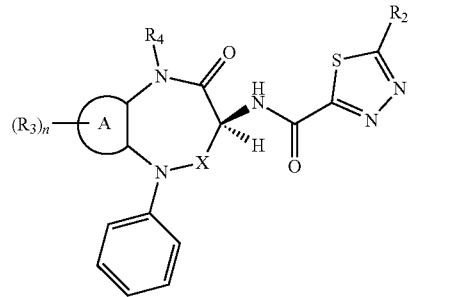
VIIb-4
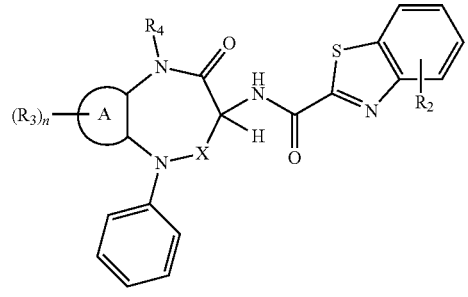
VII-5
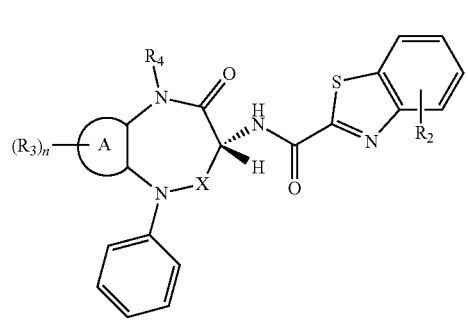
VIIa-5
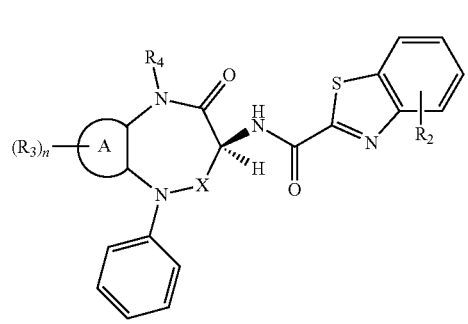
VIIb-5
-continued
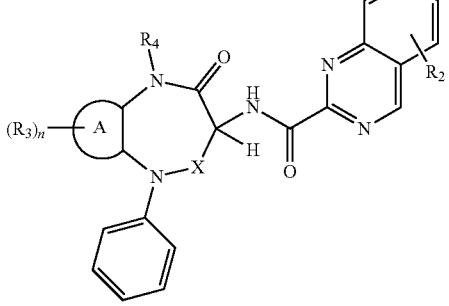
VII-6
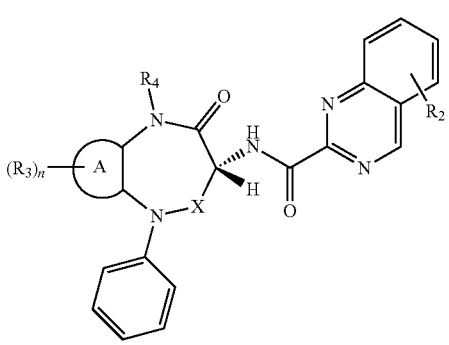
VIIa-6
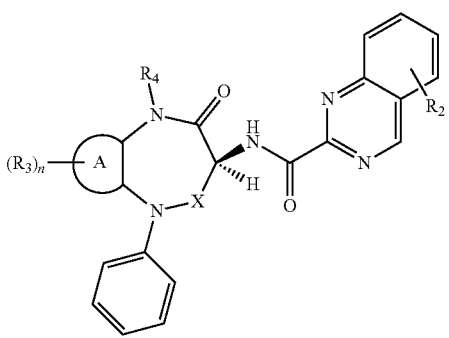
VIIb-6
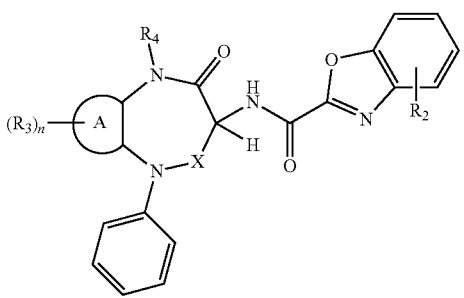
VII-7
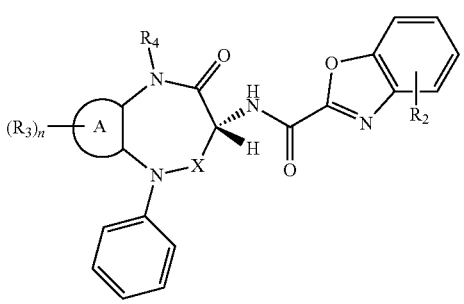
VIIa-7

-continued
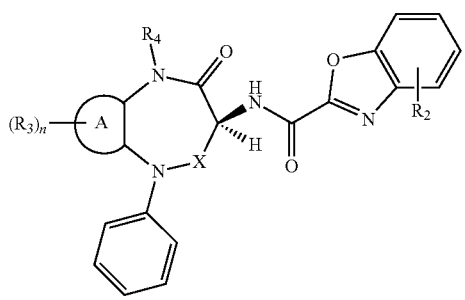
VIIb-7
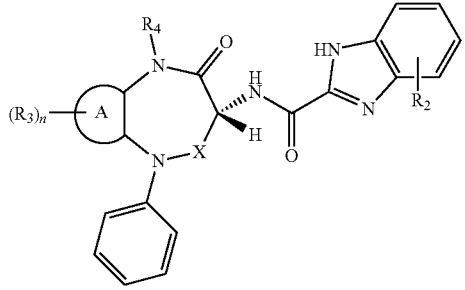
VII-8
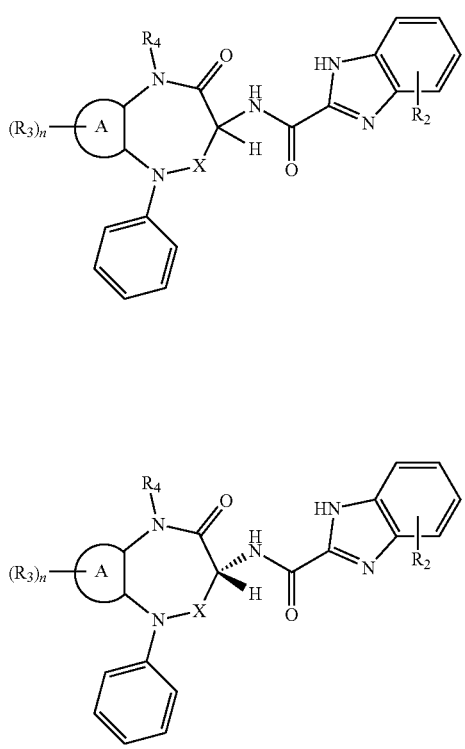
VIIa-8
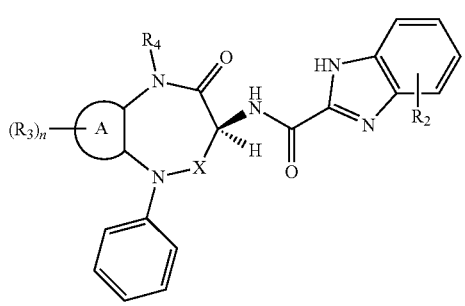
VIIb-8
wherein R$_2$, R$_3$, R$_4$, A, X, m and n are as previously defined. Preferably R$_4$ is hydrogen, A is phenyl, and n is 0.
In another embodiment, the invention provides compounds represented by Formulas (VIII-1)~(VIII-8), (VIIIa-1)~(VIIIa-8), and (VIIIb-1)~(VIIIb-8) and pharmaceutically acceptable salts, esters and prodrugs thereof:
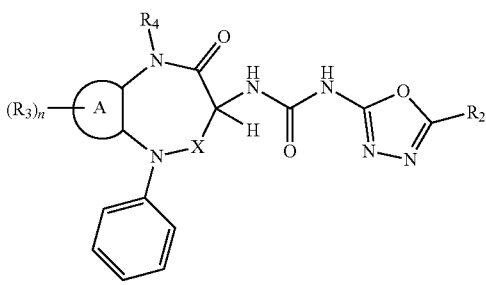
VIII-1
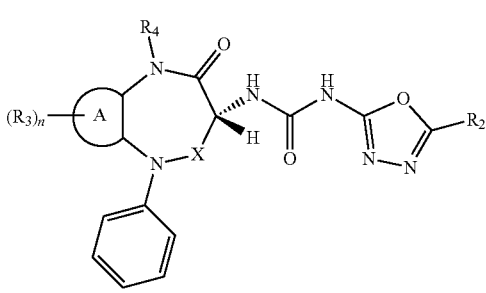
VIIIa-1
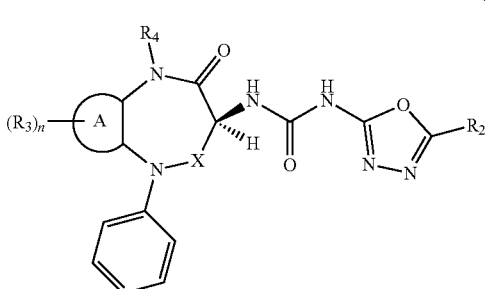
VIIIb-1
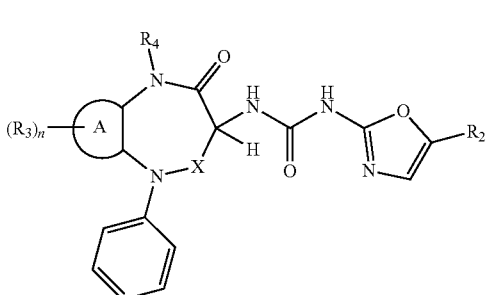
VIII-2
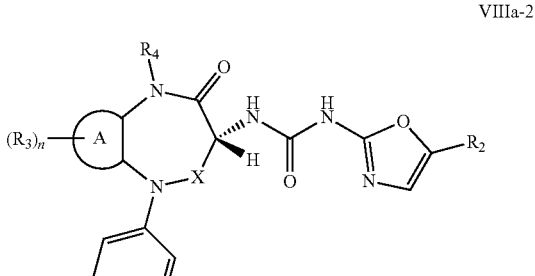
VIIIa-2

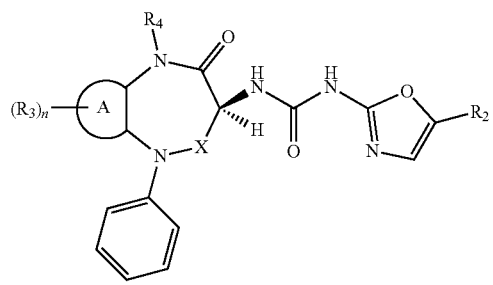
VIIIb-2
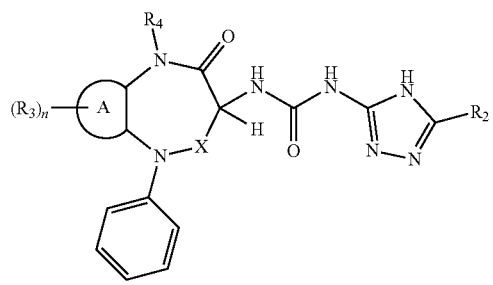
VIII-3
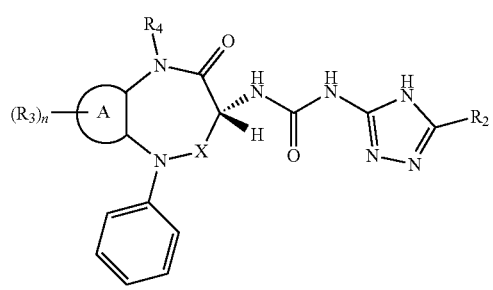
VIIIa-3
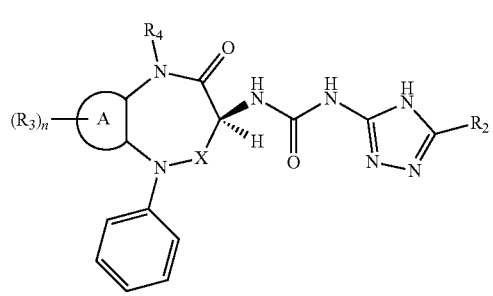
VIIIb-3
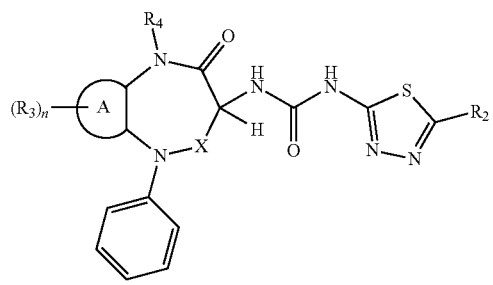
VIII-4
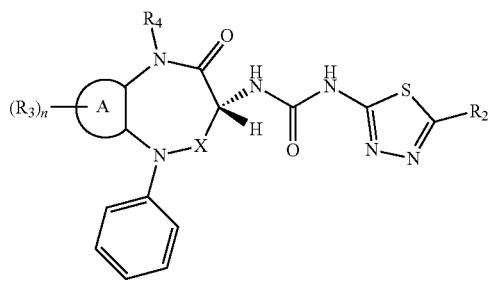
VIIIa-4
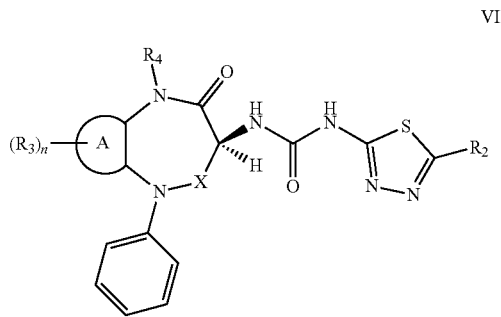
VIIIb-4
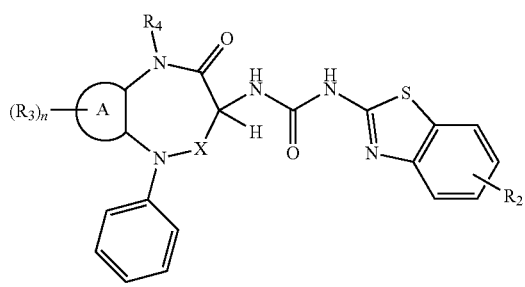
VIII-5
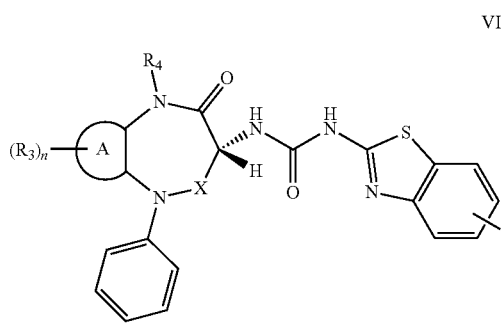
VIIIa-5
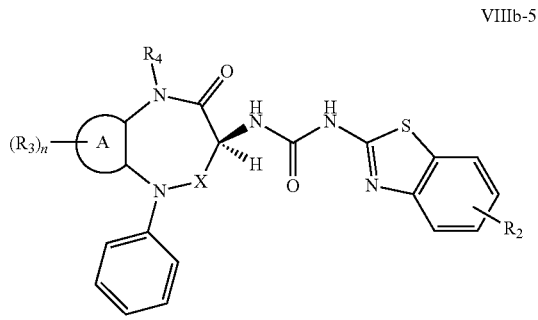
VIIIb-5

VIII-6

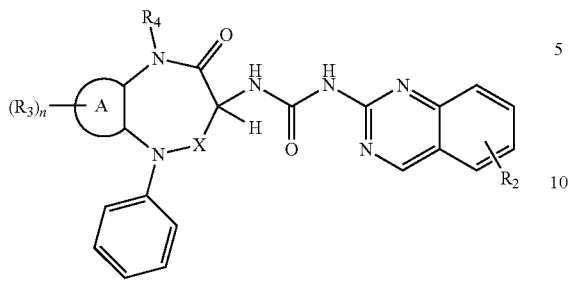

VIIIa-6

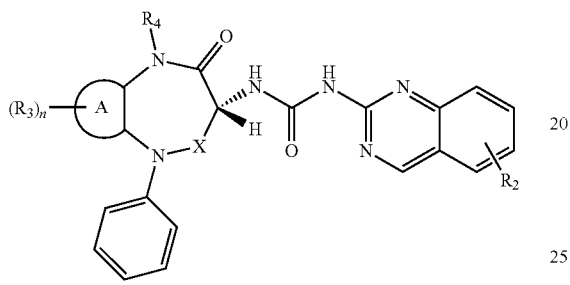

VIIIb-6

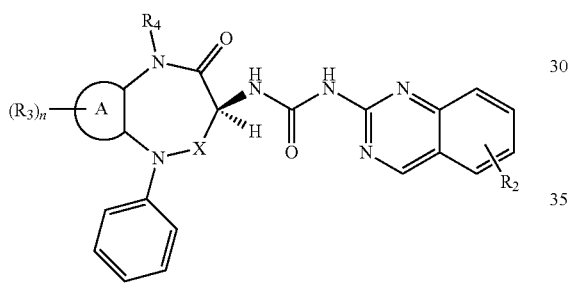

VIII-7

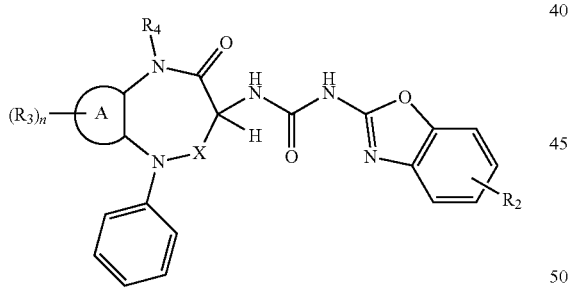

VIIIa-7

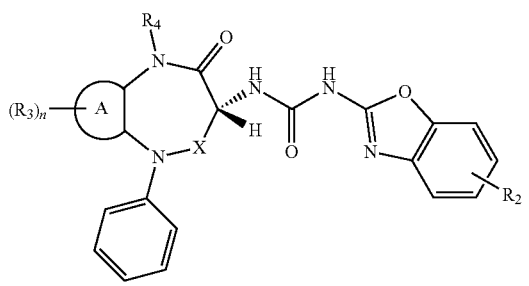

VIIIb-7

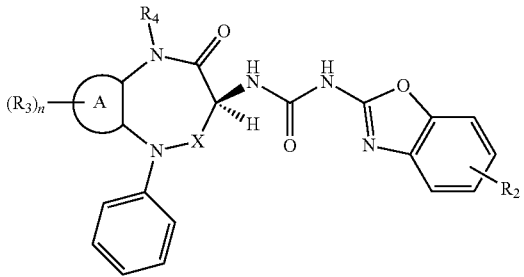

VIII-8

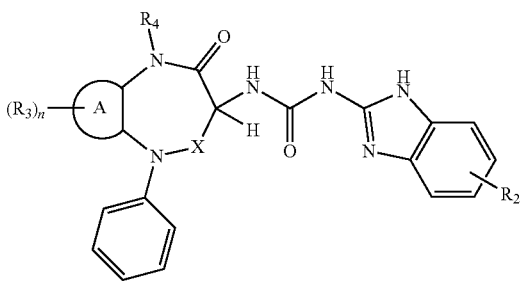

VIIIa-8

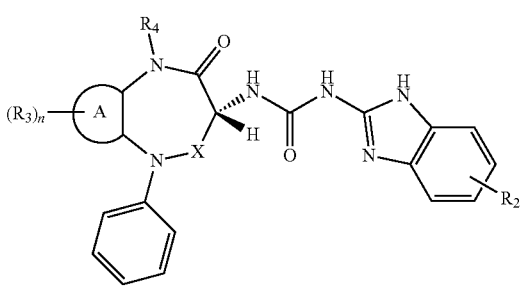

VIIIb-8

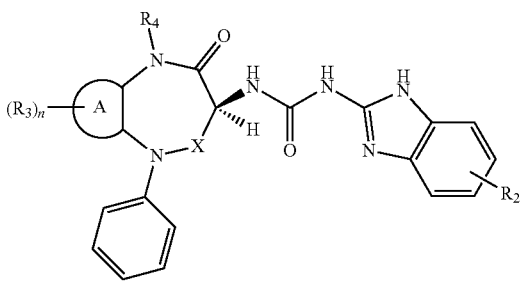

wherein $R_2$, $R_3$, $R_4$, A, X, m and n are as previously defined. Preferably $R_4$ is hydrogen, A is phenyl, and n is 0.

In particular embodiments, the invention provides compounds of Formulas (VI-1)~(VI-8), (VIa-1)~(VIa-8), (VIb-1)~(VIb-8), (VII-8), (VIIa-1)~(VIIa-8), (VIIb-1)~(VIIb-8), (VIII-8), (VIIIa-1)~(VIIIa-8), and (VIIIb-1)~(VIIIb-8) and pharmaceutically acceptable salts, esters and prodrugs thereof, where $R_2$ is selected from the groups set forth in Table 1 (Entry 1 to Entry 186 in Table 1), each of which is optionally further substituted.

TABLE 1

| Entry | R₂ |
|---|---|
| 1 | phenyl |
| 2 | 2-fluorophenyl |
| 3 | 3-fluorophenyl |
| 4 | 4-fluorophenyl |
| 5 | 2,4-difluorophenyl |
| 6 | pyridin-4-yl |
| 7 | pyridin-2-yl |
| 8 | 5-methoxypyridin-2-yl |
| 9 | 4-methoxypyridin-2-yl |
| 10 | 6-methoxypyridin-2-yl |
| 11 | 6-(methoxymethyl)pyridin-2-yl |
| 12 | thiophen-2-yl |
| 13 | thiophen-2-yl |
| 14 | furan-2-yl |
| 15 | furan-3-yl |
| 16 | 5-methylfuran-2-yl |
| 17 | 1H-pyrrol-2-yl |
| 18 | 1H-pyrrol-3-yl |
| 19 | 1H-pyrrol-1-yl |
| 20 | oxazol-2-yl |
| 21 | oxazol-5-yl |

TABLE 1-continued
| Entry | R₂ |
|---|---|
| 22 | 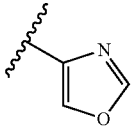 [SMILES: *c1cocn1] |
| 23 | 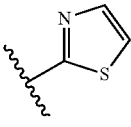 |
| 24 | 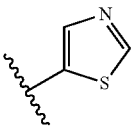 [SMILES: *c1cncs1] |
| 25 | 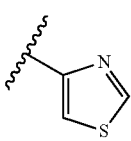 |
| 26 | 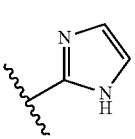 |
| 27 | 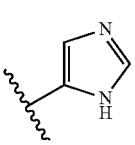 |
| 28 | 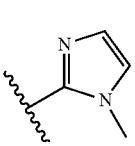 |
| 29 | 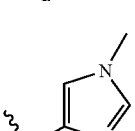 |
| 30 | 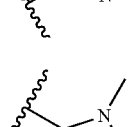 |
| 31 | 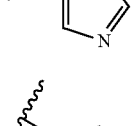 |
| 32 | 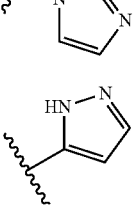 |
| 33 | 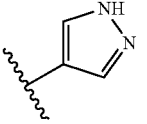 [SMILES: *c1cn[nH]c1] |
| 34 | 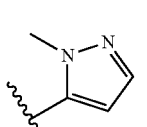 |
| 35 | 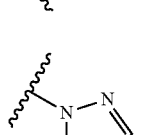 |
| 36 | 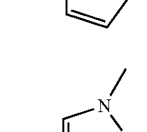 |
| 37 | 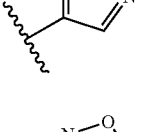 |
| 38 | 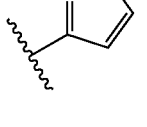 |
| 39 | 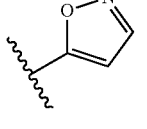 |
| 40 | 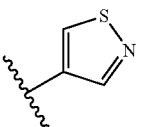 [SMILES: *c1cnsc1] |
| 41 | 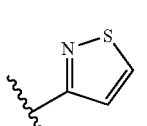 |
| 42 | 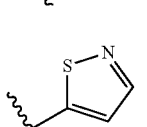 |

TABLE 1-continued
| Entry | R₂ |
|---|---|
| 43 | 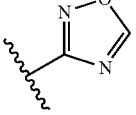 |
| 44 | 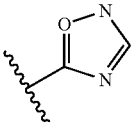 |
| 45 | 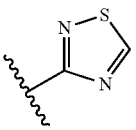 |
| 46 | 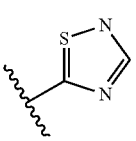 |
| 47 | 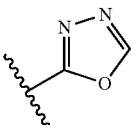 |
| 48 | 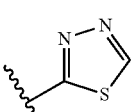 |
| 49 | 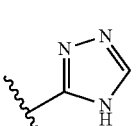 |
| 50 | 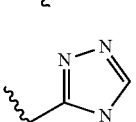 |
| 51 | 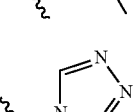 |
| 52 | 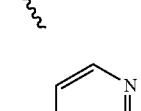 |
| 53 | 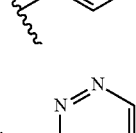 |
| 54 | 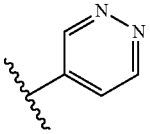 [SMILES: *c1ccnnc1] |
| 55 | 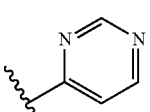 |
| 56 | 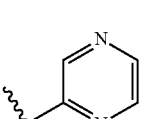 |
| 57 | 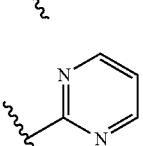 |
| 58 | 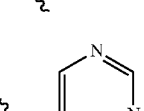 |
| 59 | 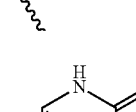 |
| 60 | 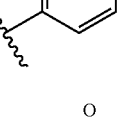 |
| 61 | 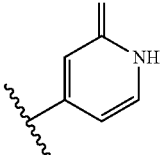 |
| 62 | 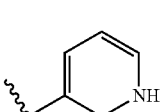 |
| 63 | 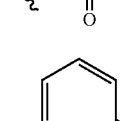 |

TABLE 1-continued
| Entry | R₂ |
|---|---|
| 64 | 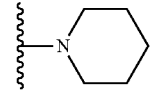 [SMILES: *N1CCCCC1] |
| 65 | 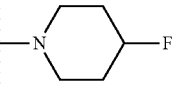 |
| 66 | 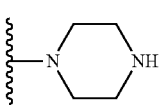 |
| 67 | 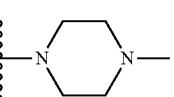 |
| 68 | 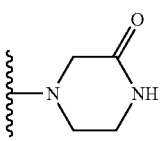 [SMILES: *N1CCNC(=O)C1] |
| 69 | 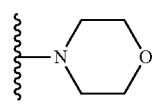 |
| 70 | 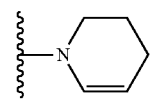 |
| 71 | 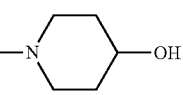 |
| 72 | 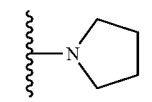 |
| 73 | 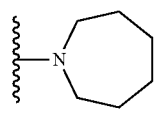 |
| 74 | 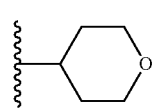 |
| 75 | 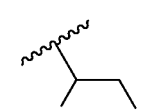 |
| 76 | 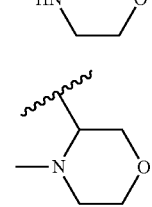 |
| 77 | 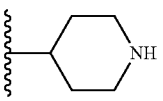 |
| 78 | 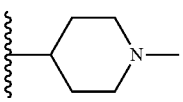 |
| 79 | 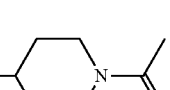 |
| 80 | 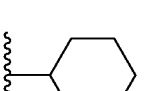 |
| 81 | 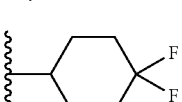 |
| 82 | 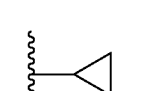 |
| 83 | 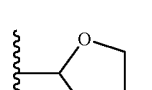 |
| 84 | 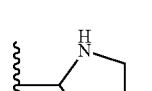 |
| 85 | 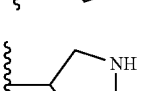 |
| 86 | 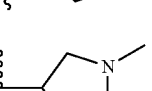 |
| 87 | 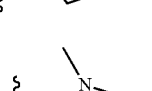 |
| 88 | 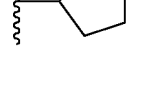 |
| 89 | 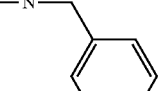 |

TABLE 1-continued

| Entry | R₂ |
|---|---|
| 90 | -NH-phenyl |
| 91 | -NH-oxetan-3-yl |
| 92 | -CH₂-phenyl |
| 93 | -C(O)NH-(3-fluorophenyl) |
| 94 | -S(O)₂-NH-Me |
| 95 | 4-methoxyphenyl |
| 96 | 3-methoxyphenyl |
| 97 | -C(O)-piperidin-1-yl |
| 98 | 2-methoxyphenyl |
| 99 | 3-methoxy-4-fluorophenyl |
| 100 | 2,3-difluorophenyl |
| 101 | 3,4-difluorophenyl |
| 102 | 4-chlorophenyl |
| 103 | 4-(trifluoromethyl)phenyl |
| 104 | 4-cyanophenyl |
| 105 | 4-(trifluoromethoxy)phenyl |
| 106 | 4-(methylsulfonyl)phenyl |
| 107 | 4-sulfamoylphenyl |

TABLE 1-continued
| Entry | R₂ |
|---|---|
| 108 | 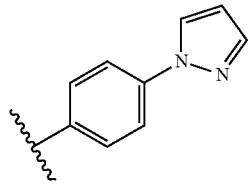 [SMILES: *c1ccc(-n2cccn2)cc1] |
| 109 | 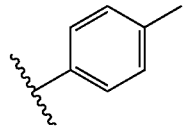 [SMILES: *c1ccc(C)cc1] |
| 110 | 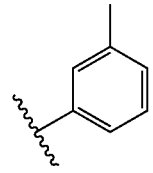 [SMILES: *c1cccc(C)c1] |
| 111 | 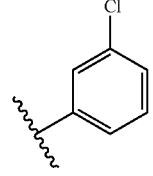 [SMILES: *c1cccc(Cl)c1] |
| 112 | 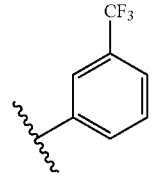 [SMILES: *c1cccc(C(F)(F)F)c1] |
| 113 | 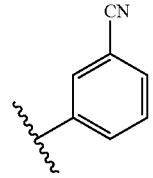 [SMILES: *c1cccc(C#N)c1] |
| 114 | 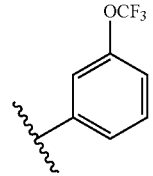 [SMILES: *c1cccc(OC(F)(F)F)c1] |
| 115 | 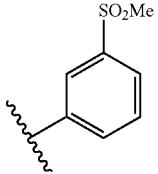 [SMILES: *c1cccc(S(C)(=O)=O)c1] |
| 116 | 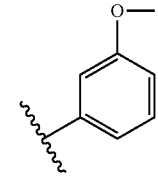 |
| 117 | 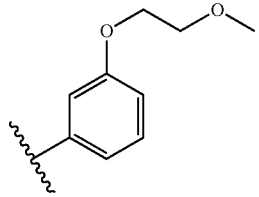 [SMILES: *c1cccc(OCCOC)c1] |
| 118 | 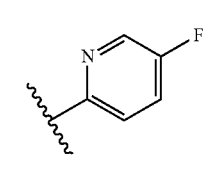 [SMILES: *c1ccc(F)cn1] |
| 119 | 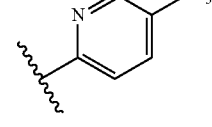 |
| 120 | 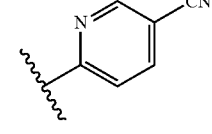 |
| 121 | 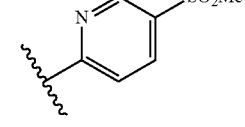 |
| 122 | 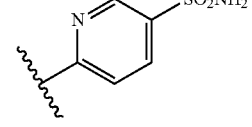 |
| 123 | 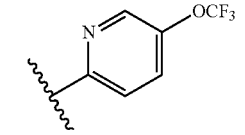 [SMILES: *c1ccc(OC(F)(F)F)cn1] |
| 124 | 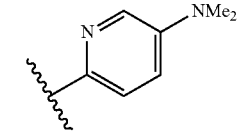 [SMILES: *c1ccc(N(C)C)cn1] |

TABLE 1-continued
| Entry | R₂ |
|---|---|
| 125 | 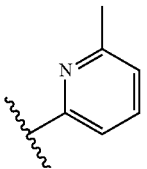 [SMILES: *c1cccc(C)n1] |
| 126 | 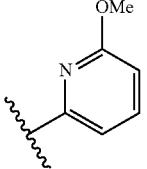 [SMILES: *c1cccc(OC)n1] |
| 127 | 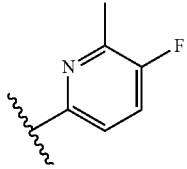 [SMILES: *c1ccc(F)c(C)n1] |
| 128 | 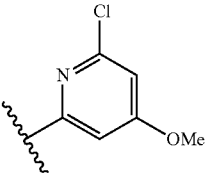 [SMILES: *c1cc(OC)cc(Cl)n1] |
| 129 | 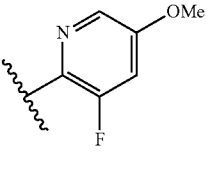 [SMILES: *c1ncc(OC)cc1F] |
| 130 | 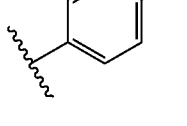 |
| 131 | 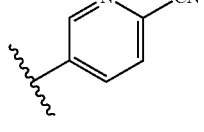 |
| 132 | 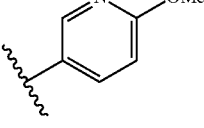 |
| 133 | 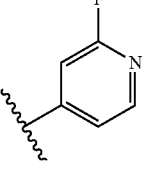 |
TABLE 1-continued
| Entry | R₂ |
|---|---|
| 134 | 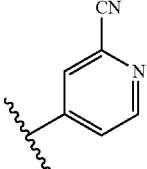 [SMILES: *c1ccnc(C#N)c1] |
| 135 | 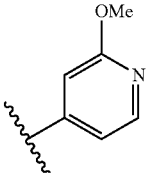 [SMILES: *c1ccnc(OC)c1] |
| 136 | 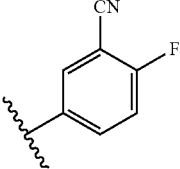 [SMILES: *c1ccc(F)c(C#N)c1] |
| 137 | 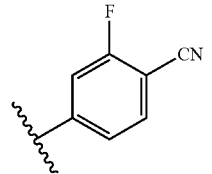 [SMILES: *c1ccc(C#N)c(F)c1] |
| 138 | 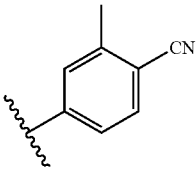 [SMILES: *c1ccc(C#N)c(C)c1] |
| 139 | 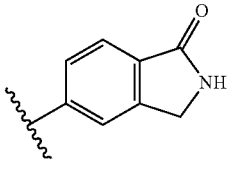 [SMILES: *c1ccc2c(c1)CNC2=O] |
| 140 | 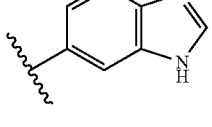 |
| 141 | 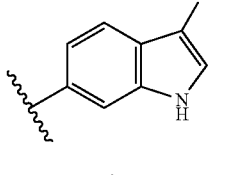 |
| 142 | 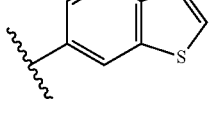 |

TABLE 1-continued
| Entry | R2 |
|---|---|
| 143 | 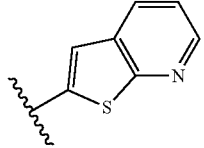 [SMILES: *c1cc2cccnc2s1] |
| 144 | 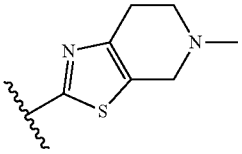 [SMILES: *c1nc2c(s1)CN(C)CC2] |
| 145 | 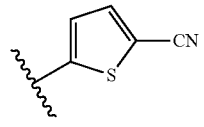 |
| 146 | 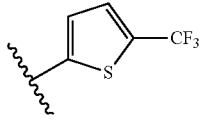 [SMILES: *c1ccc(C(F)(F)F)s1] |
| 147 | 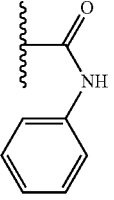 [SMILES: *C(=O)Nc1ccccc1] |
| 148 | 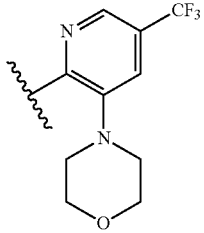 [SMILES: *c1ncc(C(F)(F)F)cc1N1CCOCC1] |
| 149 | 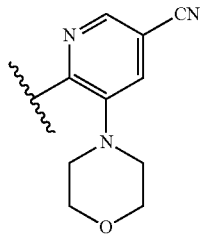 [SMILES: *c1ncc(C#N)cc1N1CCOCC1] |
| 150 | 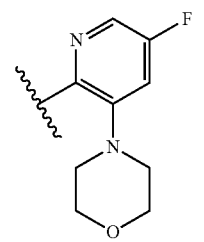 [SMILES: *c1ncc(F)cc1N1CCOCC1] |
| 151 | 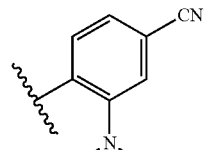 |
| 152 | 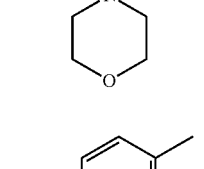 |
| 153 | 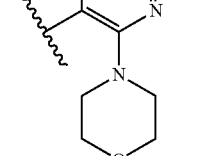 |
| 154 | 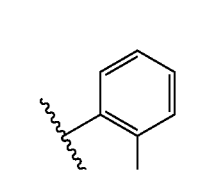 |
| 155 | 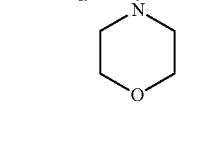 |
| 156 | 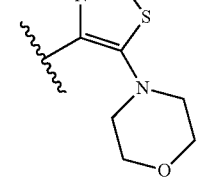 |

TABLE 1-continued

| Entry | R₂ |
|---|---|
| 157 | 3-fluorophenyl sulfonamide |
| 158 | 4-fluorophenyl sulfonamide |
| 159 | pyridin-2-yl sulfonamide |
| 160 | pyridin-3-yl sulfonamide |
| 161 | pyridin-4-yl sulfonamide |
| 162 | tetrahydropyran-4-yl sulfonamide |
| 163 | morpholine sulfonamide |
| 164 | 3-methylisoxazol-5-yl |
| 165 | 4-(dimethylamino)phenyl |
| 166 | 6-(1H-pyrazol-1-yl)pyridin-3-yl |
| 167 | 6-(1H-pyrazol-1-yl)pyridin-3-yl (isomer) |
| 168 | 4-(pyrrolidin-1-yl)phenyl |
| 169 | 4-morpholinophenyl |
| 170 | 4-(1H-imidazol-1-yl)phenyl |
| 171 | 4-(3-(trifluoromethyl)-1H-pyrazol-1-yl)phenyl |

TABLE 1-continued

| Entry | R₂ |
|---|---|
| 172 | (4-(1,2,4-triazol-1-yl)phenyl) |
| 173 | (4-(2-methyltetrazol-5-yl)phenyl) |
| 174 | (2-methylbenzothiazol-6-yl) |
| 175 | (2-methyl-3-cyanopyridin-6-yl) |
| 176 | (5-(methoxymethyl)furan-2-yl) |
| 177 | (5-((dimethylamino)methyl)furan-2-yl) |
| 178 | isopropyl |
| 179 | (5-methylthiophen-2-yl) |
| 180 | cyclopentyl |
| 181 | cyclobutyl |
| 182 | (5-chlorofuran-2-yl) |
| 183 | naphthalen-1-yl |
| 184 | naphthalen-2-yl |
| 185 | N,N-dimethylsulfamoyl |
| 186 | N-cyclopropylsulfamoyl |

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection is subjects. The method comprises administering a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that a pharmaceutical composition contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon radicals. Preferred alkyl radicals include $C_1$-$C_6$ alkyl and $C_1$-$C_8$ alkyl radicals. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl groups include, but are not limited to, methyl, ethyl, propyl, isopropyl, n-butyl, tert-butyl, neopentyl, n-hexyl, heptyl, and octyl radicals.

The term "alkenyl" as used herein, refers to straight- or branched-chain hydrocarbon radicals having at least one carbon-carbon double bond by the removal of a single hydrogen atom. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl" as used herein, refers to straight- or branched-chain hydrocarbon radicals having at least one carbon-carbon triple bond by the removal of a single hydrogen atom. Preferred alkynyl radicals include $C_2$-$C_6$ alkynyl and $C_2$-$C_8$ alkynyl radicals. Representative alkynyl radicals include, but are not limited to, for example, ethynyl, 1-propynyl, 1-butynyl, heptynyl, octynyl and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "alkynylene" refers to an alkynyl group from which an additional hydrogen atom has been removed to form a diradical group. Alkynylene groups include, but are not limited to, for example, ethynylene, propynylene, butynylene, 1-methyl-2-butyn-1-ylene, heptynylene, octynylene, and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure, the carbocycle group can be attached to the two other elements through any two substitutable ring atoms. A $C_4$-$C_6$ carbocycle has 4-6 ring atoms.

The term "cycloalkyl", as used herein, refers to a monocyclic or polycyclic saturated carbocyclic ring compound, and the carbon atoms may be optionally oxo-substituted. A polycyclic cycloalkenyl can comprise fused rings. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl", as used herein, refers to monocyclic or polycyclic carbocyclic ring compound having at least one carbon-carbon double bond and the carbon atoms may be optionally oxo-substituted. A polycyclic cycloalkenyl can comprise fused rings, covalently attached rings or a combination thereof. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo [2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, indenyl and the like. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. A polycyclic heteroaryl can comprise fused rings, covalently attached rings or a combination thereof.

In accordance with the invention, aromatic groups can be substituted or unsubstituted.

The term "arylalkyl," as used herein, refers to functional group wherein an alkylene chain is attached to an aryl group. Examples include, but are not limited to, benzyl, phenethyl and the like. The term "substituted arylalkyl" means an arylalkyl functional group in which the aryl group is substituted. Similarly, the term "heteroarylalkyl" means a functional group wherein an alkylene chain is attached to a heteroaryl group. Examples include, but are not limited to, pyridinylmethyl, pyrimidinylethyl and the like. The term "substituted heteroarylalkyl" means a heteroarylalkyl functional group in which the heteroaryl group is substituted.

The term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "halo" or halogen" alone or as part of another substituent, as used herein, refers to a fluorine, chlorine, bromine, or iodine atom.

The term "hydrogen" includes hydrogen and deuterium. In addition, the recitation of an atom includes other isotopes of that atom so long as the resulting compound is pharmaceutically acceptable.

The term "substituted" as used herein, refers to independent replacement of one, two, three or more of the hydrogen atoms thereon with substituents including, but not limited to, deuterium, tritium, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —CN, —$NH_2$, —$N_3$, protected amino, alkoxy, thioalkoxy, oxo, thioxo, alkyl, -halo-$C_2$-$C_{12}$-alkenyl, -halo-$C_2$-$C_{12}$-alkynyl, -halo-$C_3$-$C_{12}$-cycloalkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, —$NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$— $C_1$-$C_{12}$-alkyl, —$SO_2NH$— $C_2$-$C_{12}$-alkenyl, —$SO_2NH$— $C_2$-$C_{12}$-alkynyl, —$SO_2NH$— $C_3$-$C_{12}$-cycloalkyl, —$SO_2NH$— aryl, —$SO_2NH$-heteroaryl, —$SO_2NH$— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —$NO_2$, —CN, and —$NH_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure (s) the hydroxy protecting group as described herein may be selectively removed. Hydroxy protecting groups as known in the are described generally in T. H. Greene and P. G., S. M. Wuts, *Protective Groups in Organic Synthesis*, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$), and the like.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The compounds described herein contain one or more asymmetric centers and thus give rise to enantiomers, diastereomers, and other stereoisomeric forms that may be defined, in terms of absolute stereochemistry, as (R)- or (S), or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrates.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BTC for bis(trichloromethyl)carbonate; triphosgene;
BzCl for benzoyl chloride;
CAN for ceric ammonium nitrate;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-;
1-O-(2-cyanoethyl)-(N,N-diisopropyl)-phosphoramidite;
DBU for 1,8-Diazabicycloundec-7-ene;
DCC for N,N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N,N'-disuccinimidyl carbonate;
DUPHOS for

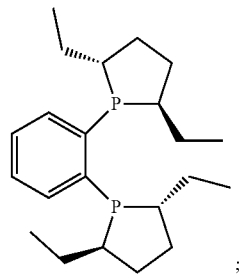 [SMILES: CC[C@@H]1CC[C@@H](CC)P1c1ccccc1P1[C@H](CC)CC[C@H]1CC ; ";"]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PMB for para-methoxybenzyl;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethyl amine;
$Tf_2O$ for trifluoromethanesulfonic anhydride;
TFA for trifluoroacetic acid;
THF for tetrahydrofuran;
TLC for thin layer chromatography;
$(TMS)_2NH$ for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or $PPh_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene;
X-Phos for 2-(dicyclohexylphosphino)-2',4',6'-triisopropylbiphenyl; and
Zhan 1 B for

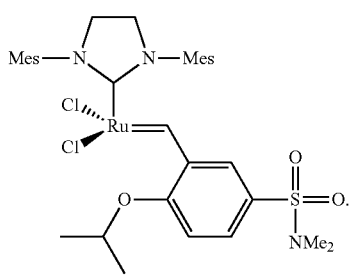

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1-1, novel RSV analogs of the compound of formula 8 are prepared starting from compounds 1 and 2. Compound 2 can be protected by groups such as, but not limited to, tert-butyloxycarbonyl (BOC), acetyl (Ac) and 2-(trimethylsilyl-ethoxy)methyl (SEM). Initially, compounds 1 and 2 are heated to reflux in the presence of $K_2CO_3$ to form compound 3. Compound 3 is converted to the corresponding aniline 4 using reduction conditions such as, but not limited to, Fe/NH4Cl in hot EtOH. Compound 4 is cyclized using amide coupling conditions like, but not restricted to, 2-(1H-benzotriazol-1-yl)-1,1,3,3-tetramethyluronium hexafluorophosphate (HBTU) and $Et_3N$ in DMF at ambient temperature to yield compound 5. Compound 5 is reacted with an alkyl, aryl or heteroaryl halide to produce compound 6. The transformation requires either C—N cross-coupling conditions using Pd or Cu catalysts or alkylation conditions requiring an inorganic or amine base. Deprotection of compound 6 with appropriate reaction conditions such as, but not limited to, acid, base or a nucleophilic fluoride source yields compound 7. Compound 7 is reacted with either an aryl, heteroaryl or alkyl halide via a displacement of the halogen (X) or via suitable coupling conditions using Pd or Cu catalysts to afford compound 8.

Scheme 1

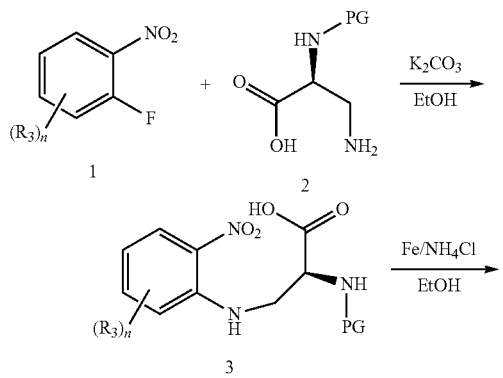

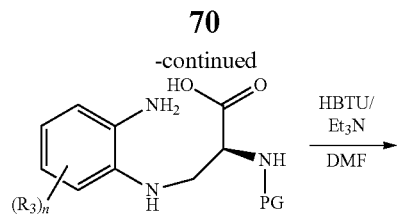

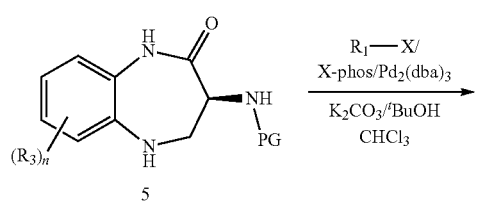

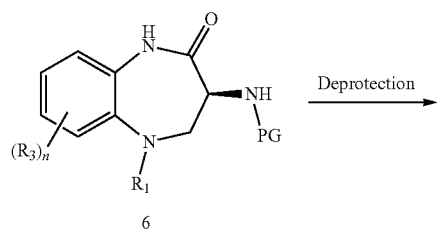

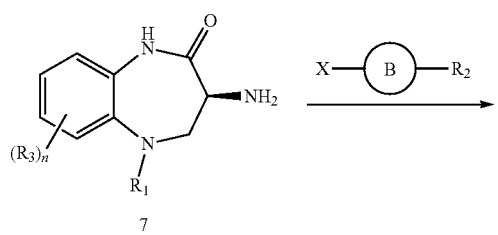

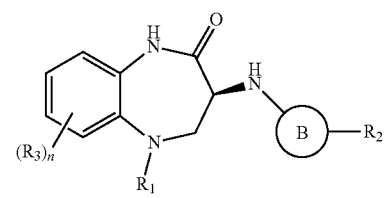

Scheme 1-2 illustrates alternative methods for assembling compounds having oxadiazole rings. Compounds 7 can be reacted with oxadiazolone 9 in the presence of a coupling reagent such as, but not limited to, (benzotriazol-1-yloxy)tris(dimethylamino)phosphonium hexafluorophosphate (BOP) to afford compounds 10, containing an oxadiazole ring. Alternatively, compound 7 is reacted with 1,1'-carbonyldiimidazole (CDI) to yield the 1H-imidazole-1-carboxamide intermediate 11. Reaction of this intermediate and hydrazide 12 produces the amino semicarbazide 13, which is cyclized to the oxadiazole compound 10 using 4-toluenesulfonyl chloride (TsCl), phosphorus(V) oxychloride ($POCl_3$) or other activating reagents.

Scheme 1-2

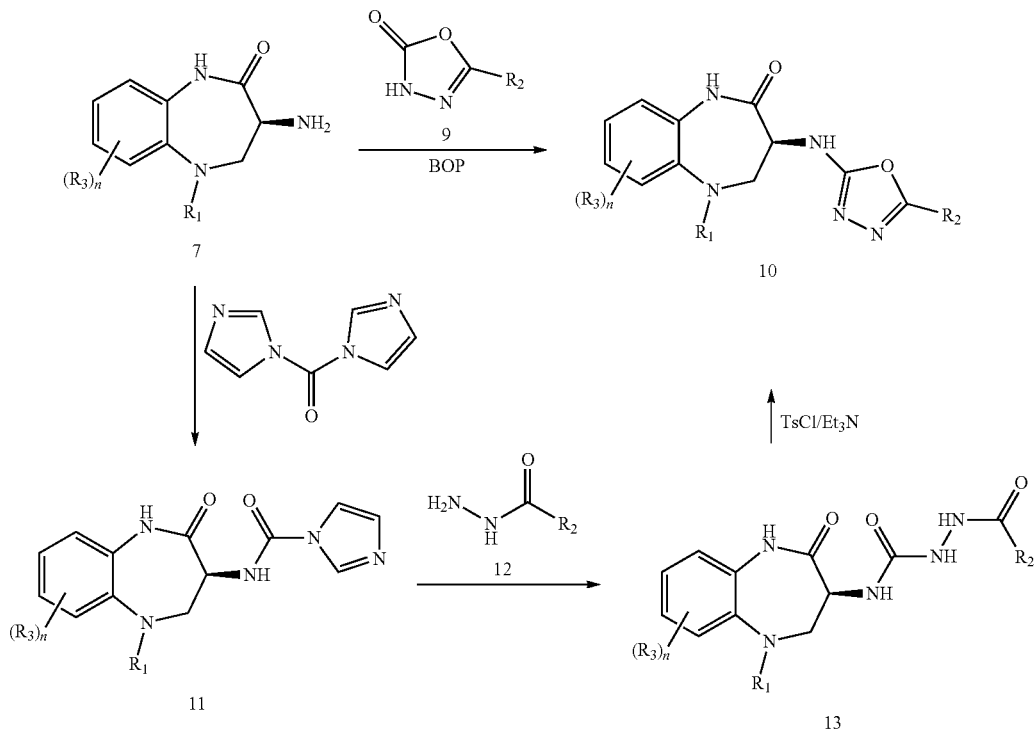

As shown in Scheme 1-3, two separate classes of compounds, 15 and 17, are made from 7. Compound 7 is reacted with alkyl, aryl or heteroaryl isocyanate 14 to yield urea-based compounds 15. Alternatively, amine 7 is reacted with acyl halide 16 to furnish amide compounds 17.

As shown in Scheme 2, amine intermediate 25 is prepared starting from compounds 18 and 3-ethoxy-3-oxopropanoic acid. Diamine 18 and 3-ethoxy-3-oxopropanoic acid are coupled using, but not limited to, N,N'-dicyclohexylcarbodiimide (DCC), which yields intermediates 19. The carbox- Scheme 1-3

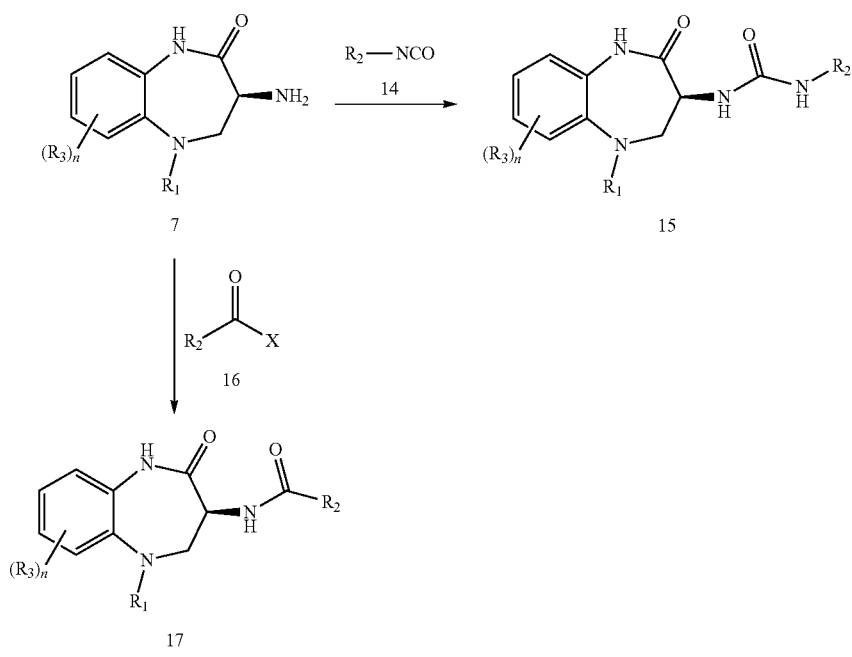

ylic acids 20 are furnished through the saponification of 19. Compound 20 is cyclized to 21 using coupling reagents such as, but not limited to, 1-ethyl-3-(3-dimethylaminopropyl) carbodiimide (EDCI) and 1-hydroxybenzotriazole (HOBt) or phosphorus pentachloride ($PCl_5$). The PMB-protected amide 22 is furnished through reaction of the amide 21 with $K_2CO_3$ and 4-methoxybenzyl chloride (PMBCl). The introduction of an azide to the malonamide derivative 22 is achieved through reaction with KOtBu and 2,4,6-triisopropylbenzenesulfonyl azide. The reduction of azide 23 to amine 24 is accomplished using palladium on carbon under a hydrogen atmosphere. Amine 25 is furnished upon cleavage of the PMB group using ceric ammonium nitrate (CAN).

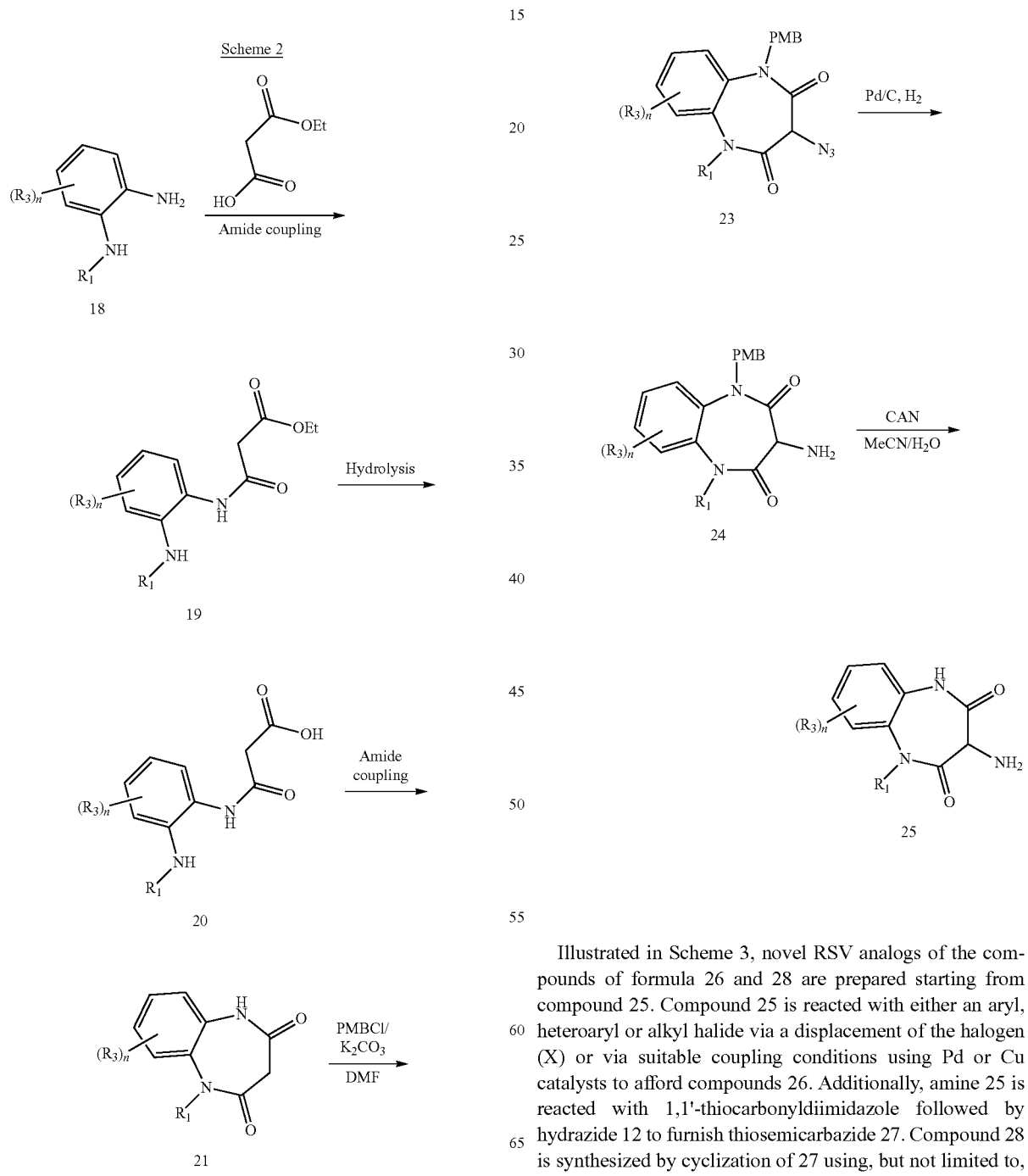

Illustrated in Scheme 3, novel RSV analogs of the compounds of formula 26 and 28 are prepared starting from compound 25. Compound 25 is reacted with either an aryl, heteroaryl or alkyl halide via a displacement of the halogen (X) or via suitable coupling conditions using Pd or Cu catalysts to afford compounds 26. Additionally, amine 25 is reacted with 1,1'-thiocarbonyldiimidazole followed by hydrazide 12 to furnish thiosemicarbazide 27. Compound 28 is synthesized by cyclization of 27 using, but not limited to, EDCI and DMF at elevated temperatures.

Scheme 3

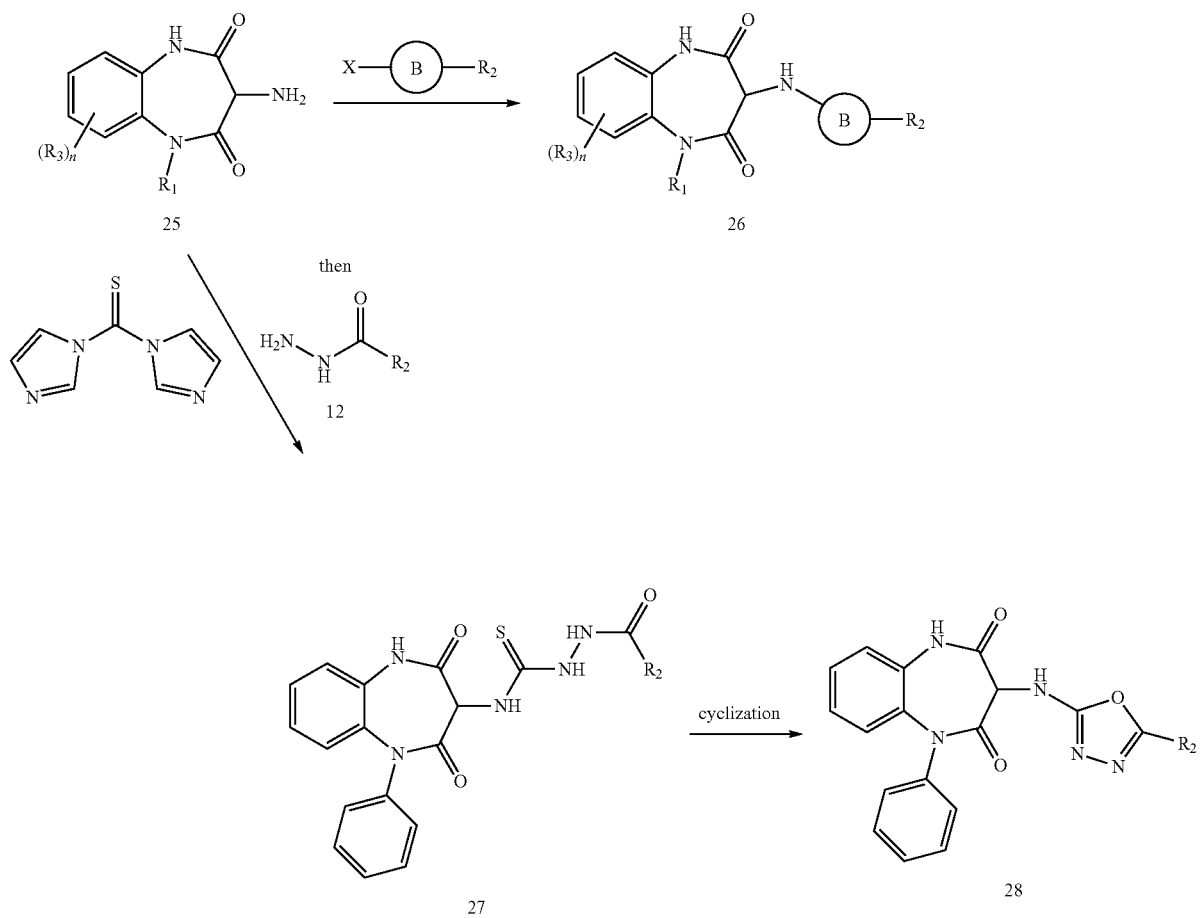

Scheme 4 depicts the various synthetic routes of hydrazide 31 starting from ester 29, wherein ⓞ is aryl, heteroaryl, —$C_3$-$C_{12}$ cycloalkyl, or 3- to 12-membered heterocycloalkyl. Compound 29 is reacted with morpholine via a displacement of the halogen (X) or via suitable coupling conditions using Pd or Cu catalysts to afford compound 30. The ester 30 is converted to the hydrazide 31 upon subjection to hydrazine hydrate and EtOH at either ambient or elevated temperatures. Alternatively, hydrazide 31 can be made in reverse fashion where 29 is converted to the hydrazide 32, which to subsequently converted to 31 when reacted with morpholine. Furthermore, 31 can be synthesized without the use of hydrazine. Ester 29 is hydrolyzed using a hydroxide base such as LiOH. Next, the carboxylic acid 33 is reacted with BOC-protected hydrazine and a coupling reagents, such as, but not limited to, 1-[Bis(dimethylamino)methylene]-1H-1,2,3-triazolo[4,5-b]pyridinium 3-oxid hexafluorophosphate (HATU), which yields intermediate 34. Subjection of the halide-containing compound 34 and morpholine to displacement or coupling conditions furnishes 35, which upon acid-promoted deprotection of the BOC group, yields hydrazide 31.

Scheme 4

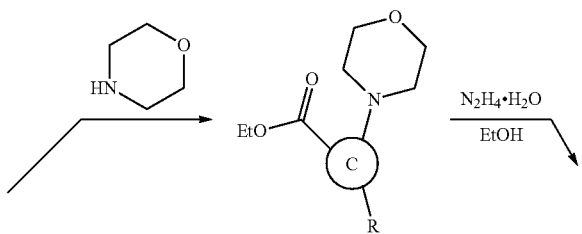

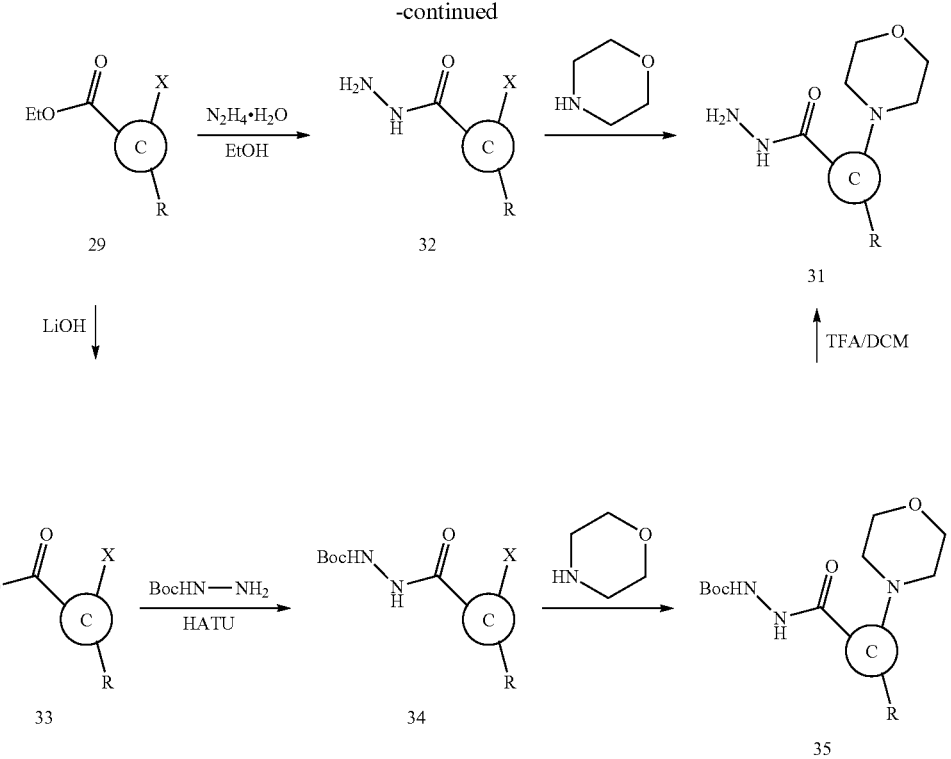

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Examples 1-18 were prepared and tested as the indicated enantiomer. Examples 19-21 were prepared and tested as a racemic mixture.

Example 1

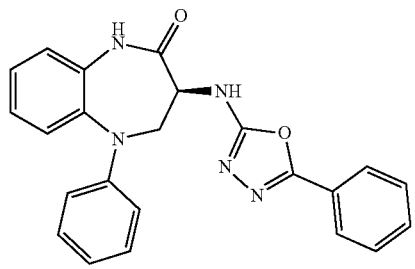 [SMILES: O=C1Nc2ccccc2N(c2ccccc2)C[C@@H]1Nc1nnc(-c2ccccc2)o1]

Example 1 Step a

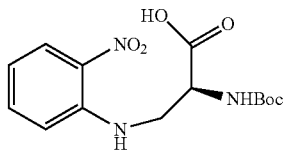 [SMILES: CC(C)(C)OC(=O)N[C@@H](CNc1ccccc1[N+](=O)[O-])C(=O)O]

A mixture of 1-fluoro-2-nitrobenzene (4.23 g, 30 mmol), $K_2CO_3$ (12.42 g, 90 mmol) and (S)-3-amino-2-(tert-butoxycarbonylamino)propanoic acid (6.73 g, 33 mmol) in EtOH (100 mL) were refluxed for 16 hours. The reaction mixture was poured into water and adjusted to pH=3-4. Then it was extracted with EtOAc. The organic layer was dried over $Na_2SO_4$, filtered and concentrated to afford (S)-2-((tert-butoxycarbonyl)amino-3-((2-nitrophenyl)amino)propanoic acid as a red solid (9.4 g) that was used without further purification. ESI-MS m/z: 326.50 $[M+H]^+$.

Example 1 Step b

A solution of the compound from step a (9.4 g, 28.9 mmol), Fe (6.48 g, 115.6 mmol) and saturated $NH_4Cl$ (45 mL) in EtOH (200 mL) was stirred at 80° C. for 1.5 hrs. Solid was filtered through celite and the filtrate was diluted with EtOAc, washed with water and separated. The organic layer was dried over Na$_2$SO$_4$, filtered and concentrated under vacuum to afford (S)-3-((20aminophenyl)amino)-2-((tert-butoxycarbonyl)amino) propanoic acid as a dark solid (10.6 g) that was used without further purification. ESI-MS m/z: 296.00 [M+H]$^+$.

Example 1 Step c

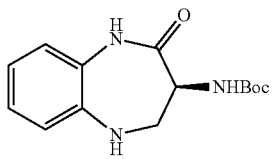 [SMILES: CC(C)(C)OC(=O)N[C@H]1CNc2ccccc2NC1=O]

A solution of the compound from step b (10.6 g, 36 mmol), HBTU (12.7 g, 39.6 mmol) and Et$_3$N (10.9 g, 108 mmol) in DMF (200 mL) was stirred at r.t. for 2 hrs. The reaction mixture was diluted with EtOAc, washed with water and brine and separated. The organic layer was dried over Na$_2$SO$_4$, filtered and concentrated. The crude product was purified by Flash (MeCN/H$_2$O) to give tert-butyl (S)-(2-oxo-2,3,4,5-tetrahydro-1H-benzo[b][1,4]diazepin-3-yl) carbmate (5.0 g) as a yellow solid ESI-MS m/z: 278.05 [M+H]$^+$.

Example 1 Step d

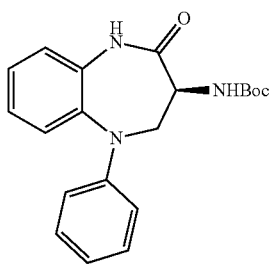 [SMILES: CC(C)(C)OC(=O)N[C@H]1CN(c2ccccc2)c2ccccc2NC1=O]

A mixture of the compound from step c (1.0 g, 36 mmol), bromobenzene (1.13 g, 7.22 mmol), X-Phos (343 mg, 0.72 mmol), Pd$_2$(dba)$_3$ (745 mg, 0.72 mmol) and K$_2$CO$_3$ (2.48 g, 18 mmol) in tBuOH (20 mL) was degassed and stirred at 80° C. for 12 hrs under N$_2$. The crude product was purified by silica gel column to give tert-butyl (S)-(4-oxo-2,3,4,5-tetrahydro-1H-benzo[b][1,4]diazepin-3-yl)carbamate (240 mg) as a yellow solid (370 mg). ESI-MS m/z: 354.25 [M+H]$^+$.

Example 1 Step e

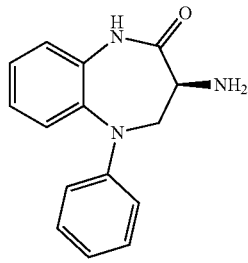 [SMILES: N[C@H]1CN(c2ccccc2)c2ccccc2NC1=O]

A mixture of the compound from step d (370 mg) in DCM (5 mL) was added TFA (2.5 mL). The reaction was stirred at r.t. for 2 hrs. Solvent was removed and the residue was basified with ammonia, extracted with DCM, washed with water and brine and separated. The organic layer was dried over Na$_2$SO$_4$, filtered and concentrated under vacuum to afford the title compound (240 mg) as a white solid ESI-MS m/z=254.20 [M+H]$^+$.

Example 1 Step f

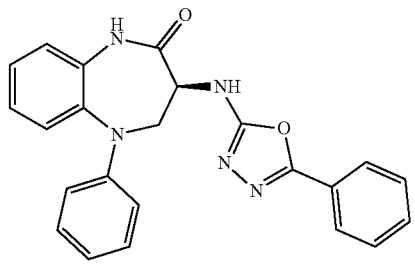 [SMILES: O=C1Nc2ccccc2N(c2ccccc2)C[C@@H]1Nc1nnc(-c2ccccc2)o1]

A solution of the compound from step e (50 mg, 0.2 mmol), 5-phenyl-1,3,4-oxadiazol-2(3H)-one (65 mg, 0.4 mmol), BOP (220 mg, 0.5 mmol) and DIPEA (104 mg, 0.8 mmol) in DMF (1 mL) was stirred at r.t. for 48 hrs. The crude product was diluted with EtOAc, washed with water (×3) and brine. The organic layer was dried over Na$_2$SO$_4$, filtered and concentrated to dryness. The crude mixture was purified by Prep-HPLC (MeCN/H$_2$O) to give (S)-5-phenyl-3-((5-phenyl-1,3,4-oxadiazol-2-yl)amino)-1,3,4,5-tetrahydro-2H-benzo[b][1,4]diazepin-2-one as a white solid (15.3 mg). ESI-MS m/z: 398.10 [M+H]$^+$.

Example 2

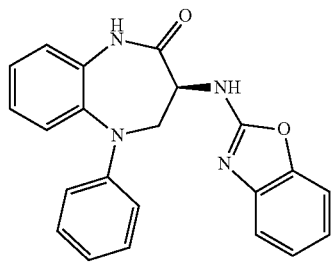 [SMILES: O=C1Nc2ccccc2N(c2ccccc2)C[C@@H]1Nc1nc2ccccc2o1]

A mixture of the compound from the step e of example 1 (50 mg, 0.2 mmol), 2-chlorobenzo[d]oxazole (60 mg, 0.4 mmol), Et₃N (104 mg, 1.0 mmol) in DMF (2 mL) was stirred at 60° C. for 12 hrs. The reaction mixture was diluted with EtOAc, washed with water (×3) and brine. The organic layer was dried over Na₂SO₄, filtered and concentrated to dryness. The crude product was purified by Prep-HPLC (MeCN/H₂O) to give (S)-3-(benzo[d]oxazol-2-ylamino)-5-phenyl-1,3,4,5-tetrahydro-2H-benzo[b][1,4]diazepin-2-one as a white solid (26.6 mg). ESI-MS m/z: 371.05 [M+H]⁺.

Example 3

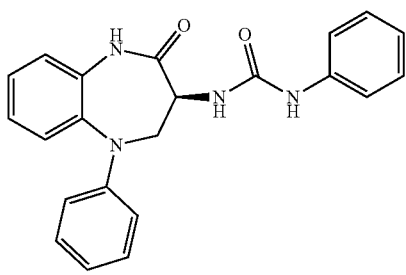 [SMILES: O=C(Nc1ccccc1)N[C@H]1CN(c2ccccc2)c2ccccc2NC1=O]

Example 3 was prepared from the compound (step e in example 1) and phenyl isocyanate. ESI-MS m/z: 373.05 [M+H]⁺.

Example 4

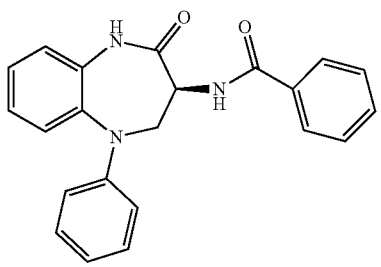 [SMILES: O=C(N[C@H]1CN(c2ccccc2)c2ccccc2NC1=O)c1ccccc1]

A mixture of the compound from the step e of example 1 (50 mg, 0.2 mmol), benzoic acid (49 mg, 0.4 mmol), HATU (152 mg, 0.4 mmol) and DIPEA (52 mg, 0.4 mmol) in DMF (2 mL) was stirred at r.t. for 2 hrs. The crude product was purified by Prep-HPLC (MeCN/H₂O) to give (S)—N-(4-oxo-1-phenyl-2,3,4,5-tetrahydro-1H-benzo[b][1,4]diazepin-3-yl)benzamide as a white solid (34.4 mg). ESI-MS m/z: 358.10 [M+H]⁺. ¹H NMR (300 MHz, DMSO-d₆) δ 3.88-4.26 (m, 2H), 4.82 (dt, J=12.2, 7.6 Hz, 1H), 6.63-6.76 (m, 2H), 6.84 (t, J=7.3 Hz, 1H), 7.14-7.38 (m, 5H), 7.44-7.69 (m, 3H), 7.82-8.04 (m, 2H), 8.69 (d, J=8.3 Hz, 1H), 10.05 (s, 1H).

Example 5

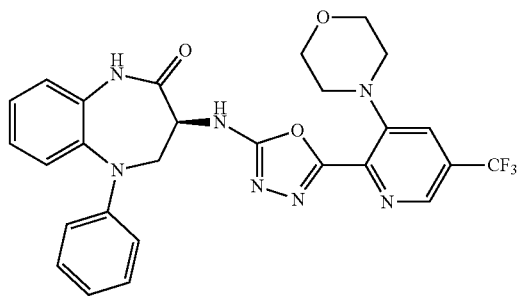 [SMILES: O=C1Nc2ccccc2N(c2ccccc2)C[C@@H]1Nc1nnc(-c2ncc(C(F)(F)F)cc2N2CCOCC2)o1]

Example 5 Step a

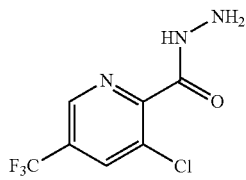 [SMILES: NNC(=O)c1ncc(C(F)(F)F)cc1Cl]

A mixture of ethyl 3-chloro-5-(trifluoromethyl)picolinate (1.336 g, 5.27 mmol) and hydrazine hydrate (2 mL, 41.2 mmol) in ethanol (4 ml) was heated at 70° C. for 30 min (confirmed by TLC). After cooling, the reaction diluted with DCM (30 mL), washed with water and separated. The aqueous layer was extracted with DCM. The combined organic layer was washed with water and brine. The organic layer was dried (Na₂SO₄), filtered and concentrated to dryness. The residue was directly used for next reaction. ESI-MS m/z=240.2 [M+H]⁺.

Example 5 Step b

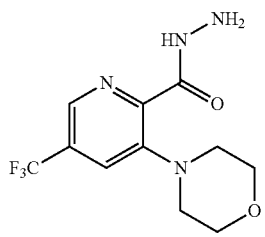 [SMILES: NNC(=O)c1ncc(C(F)(F)F)cc1N1CCOCC1]

A mixture of 3-chloro-5-(trifluoromethyl)picolinohydrazide (1.216 g, 5.08 mmol) and morpholine (6 ml, 68.6 mmol) was heated at 110° C. for 4 hrs. The reaction was concentrated, diluted with DCM (20 mL), washed with water and separated. The aqueous layer was extractd with DCM. The combined organic layer was washed with H₂O and brine. The organic layer was dried (Na₂SO₄), filtered and concentrated to dryness. The residue was dissolved in EtOAc (8.4 mL, 7 vols) by instant heating. Then, the seed was added and kept at room temperature for 4 days (needle crystal formed). It was fitered through a fritted funnel, washed with 20% EtOAc in hexanes and dried. 1ˢᵗ crystal: 630 mg. The mother liquor was concentrated to ~⅓, kept for overnight, filtered, washed with 20% EtOAc in hexanes and dried to give 2$^{nd}$ crystal: 162.6 mg. It was identical to 1st one (by HPLC and proton-NMR). Total: 792.6 mg as a light yellow solid. ESI-MS m/z=291.0 [M+H]$^+$. $^1$H-NMR (300 MHz, DMSO-d$_6$): δ 9.63 (s, 1H), 8.49 (s, 1H), 7.71 (s, 1H), 4.54 (m, 2H), 3.77-3.68 (m, 4H), 3.18-3.06 (m, 4H).

Example 5 Step c

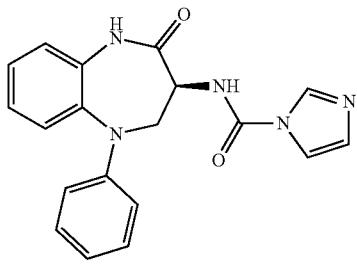 [SMILES: O=C1Nc2ccccc2N(c2ccccc2)C[C@@H]1NC(=O)n1ccnc1]

To a oven-dried round-bottomed flask, CDI (960 mg, 5.92 mmol) was dissolved in acetonitrile (9.87 mL) under nitrogen. The reaction mixture was cooled to 0° C. and (S)-3-amino-5-phenyl-1,3,4,5-tetrahydro-2H-benzo[b][1,4]diazepin-2-one (500 mg, 1.974 mmol) was added portionwise over 5 minutes. The reaction mixture was stirred at 0° C. for 1 hour and then removed from the ice bath. The reaction mixture was warmed to RT and stirred for 2 hours. Next, water (213 μl, 11.84 mmol) was added dropwise with syringe. The reaction mixture was concentrated to a viscous oil, which was taken forward crude. ESI-MS m/z=348.2 [M+H]$^+$.

Example 5 Step d

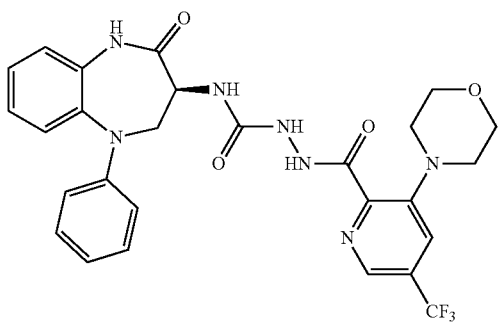 [SMILES: O=C(NNC(=O)c1ncc(C(F)(F)F)cc1N1CCOCC1)N[C@H]1CN(c2ccccc2)c2ccccc2NC1=O]

In a oven-dried vial, (S)—N-(4-oxo-1-phenyl-2,3,4,5-tetrahydro-1H-benzo[b][1,4]diazepin-3-yl)-1H-imidazole-1-carboxamide (274 mg, 0.789 mmol) was dissolved in DMSO (1578 μl). At room temperature, 3-morpholino-5-(trifluoromethyl)picolinohydrazide (229 mg, 0.789 mmol) was added to the vial. The reaction mixture was allowed to stir at room temperature for 24 hours. Upon reaction completion, water was added to the flask and the aqueous was extracted with EtOAc (3×). The organic layer was dried with Na$_2$SO$_4$, filter and concentrated. (S)-2-(3-morpholino-5-(trifluoromethyl)picolinoyl)-N-(4-oxo-1-phenyl-2,3,4,5-tetrahydro-1H-benzo[b][1,4]diazepin-3-yl)hydrazine-1-carboxamide (425 mg). ESI-MS m/z=570.2 [M+H]$^+$.

Example 5 Step e

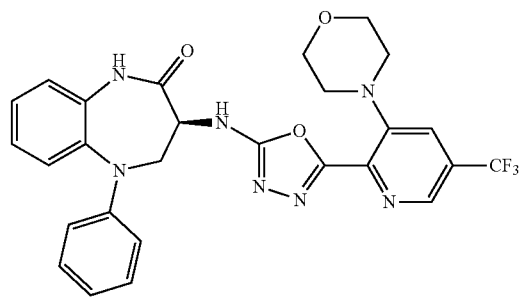 [SMILES: O=C1Nc2ccccc2N(c2ccccc2)C[C@@H]1Nc1nnc(-c2ncc(C(F)(F)F)cc2N2CCOCC2)o1]

In a oven-dried vial, (S)-2-(3-morpholino-5-(trifluoromethyl)picolinoyl)-N-(4-oxo-1-phenyl-2,3,4,5-tetrahydro-1H-benzo[b][1,4]diazepin-3-yl)hydrazine-1-carboxamide (449 mg, 0.788 mmol) was dissolved in dichloromethane (15.767 mL). The reaction mixture was cooled to 0° C. and triethylamine (0.275 mL, 1.971 mmol) and tosyl-Cl (225 mg, 1.183 mmol) were added, respectively. The reaction mixture was warmed to room temperature and stirred overnight. The reaction was quench with NaHCO3 (sat.) and the aqueous layer was extracted with DCM (3×). The organic layer was dried with Na$_2$SO$_4$, filtered and concentrated. The crude product was added to a silica gel column and was eluted with acetone/hexane 0% to 100% to give (S)-3-((5-(3-morpholino-5-(trifluoromethyl)pyridin-2-yl)-1,3,4-oxadiazol-2-yl)amino)-5-phenyl-1,3,4,5-tetrahydro-2H-benzo[b][1,4]diazepin-2-one (153 mg) as a yellow solid. The enantiopurity was enriched through HPLC chiral separation. (Column=CHIRALPAK IA-3, 5*0.46 cm (5 uM); Mobile Phase=50% EtOH/50% hexanes (0.1% diethylamine); Flow rate=1 mL/min). ESI-MS m/z=552.2 [M+H]$^+$.

Example 6

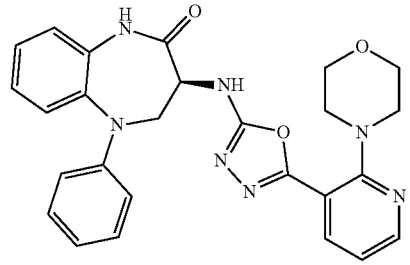 [SMILES: O=C1Nc2ccccc2N(c2ccccc2)C[C@@H]1Nc1nnc(-c2cccnc2N2CCOCC2)o1]

Example 6 Step a

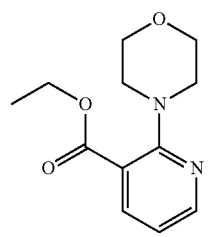 [SMILES: CCOC(=O)c1cccnc1N1CCOCC1]

A solution of ethyl 2-chloropyridine-3-carboxylate (1 g, 5.39 mmol, 1 equiv.), morpholine (1.2 g, 13.8 mmol, 2.5 equiv.) in DMSO (5 mL) was stirred at 100° C. for 1.5 hours. The mixture was cooled to r.t and diluted with water, extracted with EA (3×). The combined organic phase was washed with water and brine then dried, evaporated to give the title compound (1.48 g, crude). as yellow oil ESI-MS m/z=237.05 [M+H]⁺.

Example 6 Step b

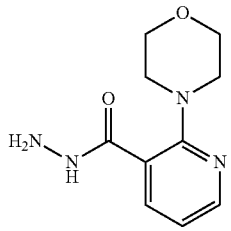 [SMILES: NNC(=O)c1cccnc1N1CCOCC1]

A solution of ethyl 2-morpholinonicotinate (1.45 g, 6.14 mmol, 1 equiv.), hydrazine hydrate (8 mL) in EtOH (8 mL) was stirred at 85° C. for 1 hour. The resulting mixture was concentrated under vacuum. The residue was purified by silica gel column chromatography, eluted with CH₂Cl₂/MeOH (0 to 10:1) to afford the title compound (1.28 g) as a yellow solid. ESI-MS m/z=223.00 [M+H]⁺.

Example 6 Step c

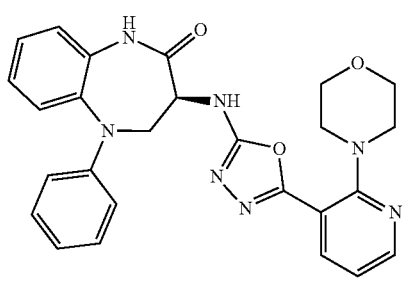 [SMILES: O=C1Nc2ccccc2N(c2ccccc2)C[C@@H]1Nc1nnc(-c2cccnc2N2CCOCC2)o1]

A solution of TCDI (213.8 mg, 1.2 mmol, 1.2 equiv.) and (S)-3-amino-5-phenyl-1,3,4,5-tetrahydro-2H-benzo[b][1,4]diazepin-2-one (253 mg, 1.0 mmol, 1.0 equiv.) in DMF (2 mL) was stirred at r.t for 15 minutes. Then 2-morpholinonicotinohydrazide (333 mg, 1.5 mmol, 1.5 equiv.) was added. The mixture was stirred at r.t for 1 hour and diluted with water. The precipitated solids were collected by filtration and washed with water to afford semicarbazide (336 mg, crude) as a yellow solid. The crude semicarbazide (336 mg, 0.649 mmol, 1 equiv.) and EDCI (620 mg, 3.25 mmol, 5 equiv.) in DMF (4 mL) was stirred at 60° C. for 1.5 hours. The resulting mixture was diluted with water. The precipitated solids were collected by filtration and washed with water. The crude product was purified by Prep Chiral-HPLC to afford the title compound (53.1 mg) as off white solid. ESI-MS m/z=484.30 [M+H]⁺. ¹H-NMR (300 MHz, DMSO-d₆): δ 3.14 (s, 4H), 3.68 (d, J=4.6 Hz, 4H), 3.98 (d, J=11.6 Hz, 1H), 4.21 (d, J=10.3 Hz, 1H), 6.71 (d, J=8.2 Hz, 2H), 6.87 (d, J=7.3 Hz, 1H), 7.05 (, 4.8 Hz, 1H), 7.24 (m, 5H), 7.96 (m, 1.8 Hz, 1H), 8.31 (d, J=9.1 Hz, 1H), 8.36 (m, 1H), 10.13 (s, 1H).

Example 7

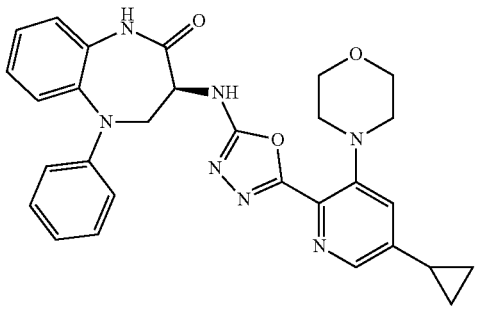 [SMILES: O=C1Nc2ccccc2N(c2ccccc2)C[C@@H]1Nc1nnc(-c2ncc(C3CC3)cc2N2CCOCC2)o1]

Example 7 Step a

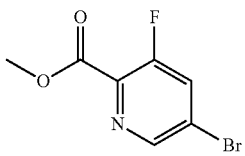

A solution of 5-bromo-3-fluoropyridine-2-carboxylic acid (2.7 g, 12.27 mmol, 1 equiv.) and H₂SO₄ (5 mL) in MeOH (10 mL) was stirred at 85° C. for 1 hour. The mixture was basified to pH 7 with saturated NaHCO₃. The resulting mixture was extracted with EA (3×) and evaporated to afford the title compound (2.3 g) as off white solid. ESI-MS m/z=233.90 [M+H]⁺.

Example 7 Step b

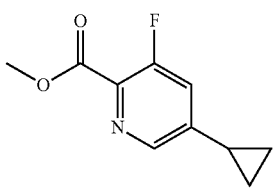

A solution of methyl 5-bromo-3-fluoropicolinate (1.7 g, 19.79 mmol, 2 equiv.), K₃PO₄ (4.6 g, 19.79 mmol, 2 equiv), Pd(dppf)Cl₂ (230 mg) and H₂O (0.5 mL) in toluene (23 mL). The resulting solution was stirred at 100° C. for 1 hour. The mixture was cooled to room temperature and extracted with EA (3×). The combined organic phase was evaporated to afford the title compound (1.48 g) as yellow oil. ESI-MS m/z=195.95 [M+H]⁺.

Example 7 Step c

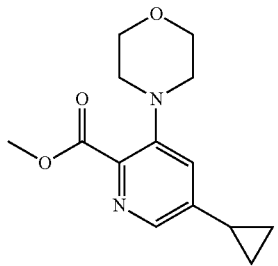 [SMILES: COC(=O)c1ncc(C2CC2)cc1N1CCOCC1]

A solution of methyl 5-cyclopropyl-3-fluoropicolinate (1.3 g, 6.66 mmol, 1 equiv.), morpholine (1.2 g, 13.33 mmol, 2 equiv.) and DIPEA (1.7 g, 13.33 mmol, 2 equiv.) in DMSO (8 mL) was stirred at 120° C. for 2 hours. The resulting mixture was extracted with EA (3×) and washed with water, dried over Na$_2$SO$_4$. After filtration, the filtrate was concentrated under reduced pressure. The residue was purified by silica gel column chromatography, eluted with EA/PE (5:1) to afford methyl 5-cyclopropyl-3-morpholinopicolinate as yellow solid (1.2 g). ESI-MS m/z=263.00 [M+H]$^+$.

Example 7 Step d

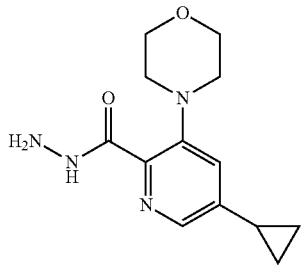 [SMILES: NNC(=O)c1ncc(C2CC2)cc1N1CCOCC1]

A solution of methyl 5-cyclopropyl-3-morpholinopicolinate (500 mg, 1.91 mmol, 1 equiv.) and hydrazine hydrate (4 mL) in EtOH (4 mL) was stirred at 85° C. for 2 hours. The resulting mixture was concentrated under vacuum. The residue was purified by silica gel column chromatography, eluted with CH$_2$Cl$_2$/MeOH (0 to 10:1) to afford product (450 mg) as brown oil. ESI-MS m/z=263.05 [M+H]$^+$.

Example 7 Step e

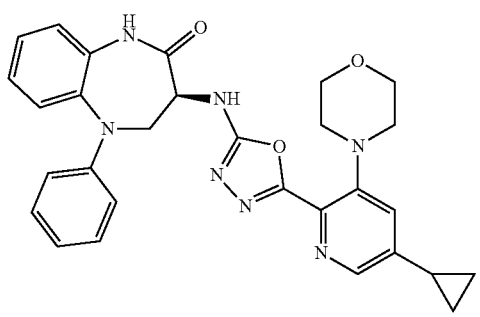 [SMILES: O=C1Nc2ccccc2N(c2ccccc2)C[C@@H]1Nc1nnc(-c2ncc(C3CC3)cc2N2CCOCC2)o1]

Prepared in a similar fashion to example 6 step c using 5-cyclopropyl-3-morpholinopicolinohydrazide. ESI-MS m/z=524.25 [M+H]$^+$. $^1$H-NMR (300 MHz, DMSO-d$_6$): δ 0.82-0.94 (m, 2H), 1.01-1.14 (m, 2H), 1.95-2.12 (m, 1H), 2.96 (m, 4H), 3.70 (t, J=4.5 Hz, 4H), 3.87-4.01 (m, 1H), 4.19 (m, 1H), 4.46 (m, 1H), 6.70 (d, J=8.1 Hz, 2H), 6.85 (m, 1H), 7.12-7.38 (m, 8H), 8.13 (d, J=1.8 Hz, 1H), 8.30 (d, J=9.3 Hz, 1H), 10.11 (s, 1H).

Example 8

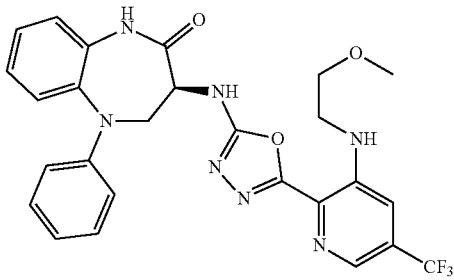 [SMILES: COCCNc1cc(C(F)(F)F)cnc1-c1nnc(N[C@H]2CN(c3ccccc3)c3ccccc3NC2=O)o1]

Example 8 Step a

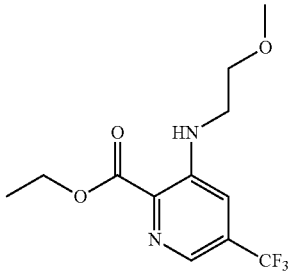 [SMILES: CCOC(=O)c1ncc(C(F)(F)F)cc1NCCOC]

A solution of ethyl 3-chloro-5-(trifluoromethyl)pyridine-2-carboxylate (3 g, 11.86 mmol, 1 equiv.), DIPEA (3.1 g, 23.72 mmol, 2 equiv.) and methoxyethan-1-amine (0.9 g, 11.86 mmol, 1 equiv.) in DMSO was stirred at 100° C. overnight. The mixture was cooled to room temperature and diluted with water, extracted with EA (3×). The combined organic phase was washed with water and brine then dried, evaporated. The residue was purified by silica gel column chromatography, eluted with EA/PE (0 to 1:1) to afford ethyl 3-((2-methoxyethyl)amino)-5-(trifluoromethyl)picolinate (700 mg) as yellow solid. ESI-MS m/z=293.10 [M+H]$^+$.

Example 8 Step b

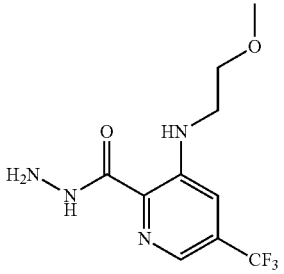 [SMILES: COCCNc1cc(C(F)(F)F)cnc1C(=O)NN]

A solution of ethyl 3-((2-methoxyethyl)amino)-5-(trifluoromethyl)picolinate (500 mg, 2 mmol, 1 equiv.) and hydrazine hydrate (8 mL) in EtOH (8 mL) was stirred at 85° C. for 1.5 hours. The resulting mixture was concentrated under vacuum. The residue was purified by silica gel column chromatography, eluted with CH$_2$Cl$_2$/MeOH (0 to 10:1) to afford product (480 mg) as yellow solid. ESI-MS m/z=278.95 [M+H]$^+$.

Example 8 Step c

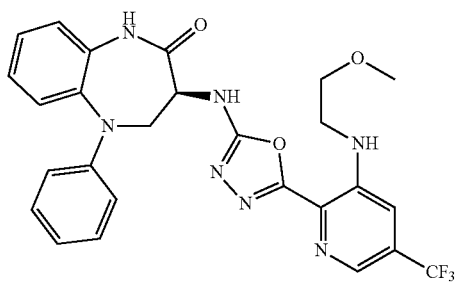 [SMILES: COCCNc1cc(C(F)(F)F)cnc1-c1nnc(N[C@H]2CN(c3ccccc3)c3ccccc3NC2=O)o1]

Prepared in a similar fashion to Example 6, step c using 3-((2-methoxyethyl)amino)-5-(trifluoromethyl)picolinohydrazide. ESI-MS m/z=540.15 [M+H]$^+$. $^1$H-NMR (300 MHz, DMSO-d$_6$) δ 3.54 (m, 2H), 3.59 (d, J=4.7 Hz, 2H), 3.88-4.02 (m, 1H), 4.23 (m, 6.6 Hz, 1H), 4.43-4.58 (m, 1H), 6.71 (d, J=8.2 Hz, 2H), 6.86 (m, 1H), 7.12-7.37 (m, 6H), 7.59 (d, J=1.8 Hz, 1H), 7.79 (m, 1H), 8.25 (d, J=1.7 Hz, 1H), 8.68 (d, J=9.1 Hz, 1H), 10.15 (s, 1H).

Example 9

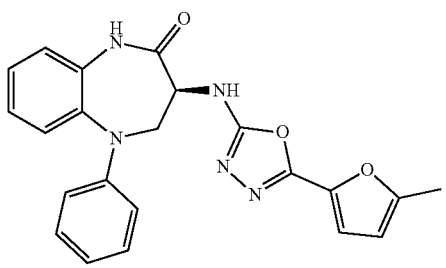 [SMILES: Cc1ccc(-c2nnc(N[C@H]3CN(c4ccccc4)c4ccccc4NC3=O)o2)o1]

Example 9 Step a

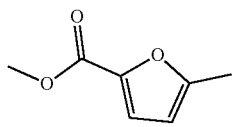

The solution of 5-methylfuran-2-carboxylic acid (1 g, 7.93 mmol, 1 equiv.), H$_2$SO$_4$ (2 mL) in MeOH (10 mL) was stirred at 85° C. for 1 hour. The pH value of the solution was adjusted to 7 with Na$_2$CO$_3$. The resulting solution was extracted with EA (3×) and evaporated to afford product (900 mg, crude) as brown solid and used directly for next step.

Example 9 Step b

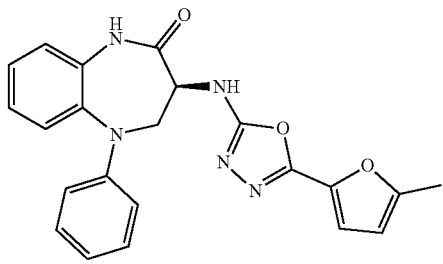 [SMILES: Cc1ccc(-c2nnc(N[C@H]3CN(c4ccccc4)c4ccccc4NC3=O)o2)o1]

A solution of methyl 5-methylfuran-2-carboxylate (900 mg, crude, step a), hydrazine hydrate (4 mL) in EtOH (4 mL) was stirred at 85° C. for 1 hour. The resulting mixture was concentrated under vacuum. The residue was purified by silica gel column chromatography, eluted with CH$_2$Cl$_2$/MeOH (0 to 10:1) to afford product (1.4 g, crude) as yellow oil. ESI-MS m/z=182.00 [M+ACN+H]$^+$.

Example 9 Step c

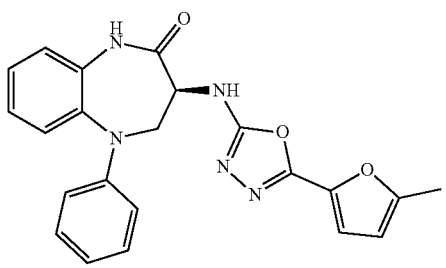 [SMILES: Cc1ccc(-c2nnc(N[C@H]3CN(c4ccccc4)c4ccccc4NC3=O)o2)o1]

Prepared in a similar fashion to Example 6, step c using 5-methylfuran-2-carbohydrazide. ESI-MS m/z=402.25 [M+H]$^+$. $^1$H-NMR (300 MHz, DMSO-d$_6$): δ 2.38 (s, 3H), 3.85-3.99 (m, 1H), 4.12-4.25 (m, 1H), 4.40 (d, J=13.6 Hz, 1H), 6.35 (m, 1H), 6.69 (d, J=8.2 Hz, 2H), 6.85 (t, J=7.4 Hz, 1H), 6.95 (d, J=3.5 Hz, 1H), 7.25 (m, 6H), 8.33 (d, J=9.2 Hz, 1H), 10.12 (s, 1H).

Example 10

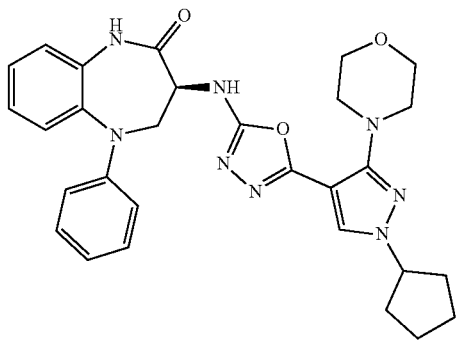 [SMILES: O=C1Nc2ccccc2N(c2ccccc2)C[C@@H]1Nc1nnc(-c2cn(C3CCCC3)nc2N2CCOCC2)o1]

Example 10 Step a

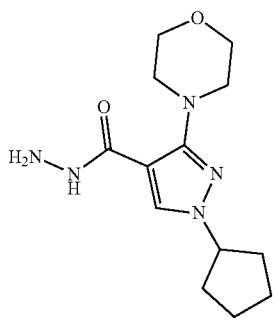 [SMILES: NNC(=O)c1cn(C2CCCC2)nc1N1CCOCC1]

The solution of ethyl 1-cyclopentyl-3-morpholino-1H-pyrazole-4-carboxylate (300 mg, 1.02 mmol, 1 equiv.), hydrazine hydrate (3 mL) in EtOH (3 mL) was stirred at 85° C. for 12 hours. The resulting mixture was concentrated under vacuum. The residue was purified by silica gel column chromatography, eluted with $CH_2Cl_2$/MeOH (0 to 10:1) to afford 1-cyclopentyl-3-morpholino-1H-pyrazole-4-carbohydrazide (360 mg, crude) as yellow solid. ESI-MS m/z=280.15 [M+H]$^+$.

Example 10 Step b

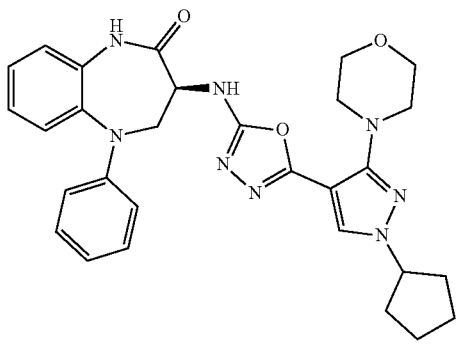 [SMILES: O=C1Nc2ccccc2N(c2ccccc2)C[C@@H]1Nc1nnc(-c2cn(C3CCCC3)nc2N2CCOCC2)o1]

Prepared in a similar fashion to Example 6, step c using 1-cyclopentyl-3-morpholino-1H-pyrazole-4-carbohydrazide. ESI-MS m/z=540.15 [M+H]$^+$. $^1$H-NMR (300 MHz, DMSO-d$_6$): δ 1.64 (m, 2H), 1.73-1.84 (m, 2H), 1.92 (m, 2H), 2.03 (m, 2H), 3.16 (s, 4H), 3.68 (m, 4H), 3.87-4.01 (m, 1H), 4.16 (m, 1H), 4.39 (m, 1H), 4.63 (m, 1H), 6.69 (d, J=8.1 Hz, 2H), 6.85 (m, 1H), 7.11-7.37 (m, 6H), 8.03 (d, J=9.3 Hz, 1H), 8.05 (s, 1H), 10.09 (s, 1H).

Example 11

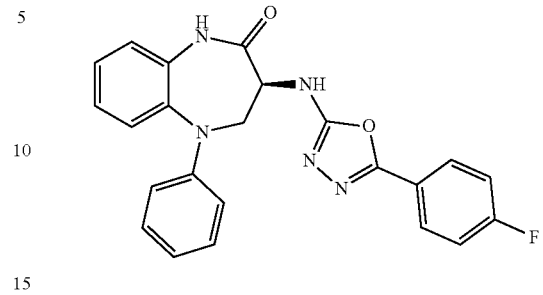

Example 11 Step a

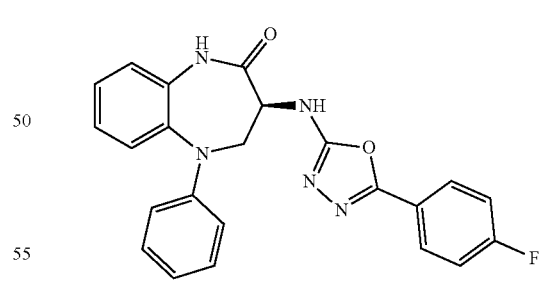

A solution of methyl 4-fluorobenzoate (3.4 g, 22.06 mmol, 1 equiv.) and hydrazine hydrate (10 mL) in EtOH (10 mL) was stirred at 85° C. for 1 hour. The resulting mixture was concentrated under vacuum. The residue was purified by silica gel column chromatography, eluted with $CH_2Cl_2$/MeOH (0 to 10:1) to afford product (2.5 g) as a white solid. ESI-MS m/z=540.15 [M+H]$^+$. ESI MS m/z=154.95 [M+H]$^+$.

Example 11 Step b

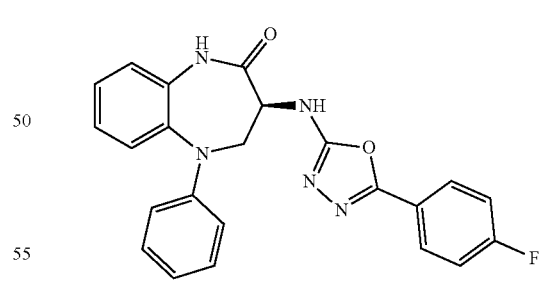

Prepared in a similar fashion to Example 6, step c using 4-fluorobenzohydrazide. ESI-MS m/z=416.20 [M+H]$^+$. $^1$H-NMR (300 MHz, DMSO-d$_6$): δ 3.90-4.00 (m, 1H), 4.20 (m, 1H), 4.40-4.52 (m, 1H), 6.70 (d, J=8.0 Hz, 2H), 6.85 (m, 1H), 7.13-7.34 (m, 6H), 7.41 (m, 2H), 7.81-7.93 (m, 2H), 8.35 (d, J=9.1 Hz, 1H), 10.13 (s, 1H).

Example 12

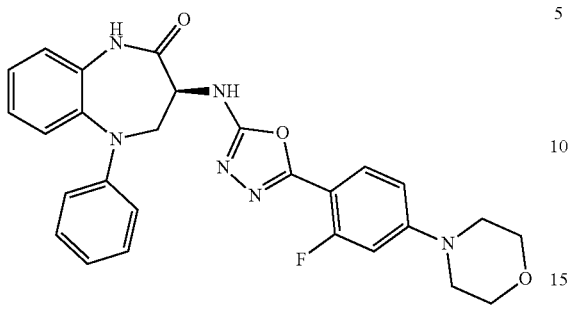

Example 12 Step a

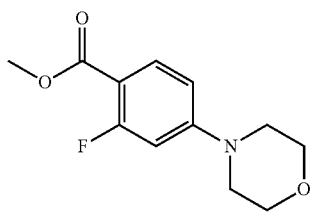 [SMILES: COC(=O)c1ccc(N2CCOCC2)cc1F]

A solution of methyl 4-bromo-2-fluorobenzoate (1 g, 4.29 mmol, 1 equiv.), morpholine (748 mg, 8.58 mmol, 2 equiv.), Ruphos (300 mg), Cs$_2$CO$_3$ (1.6 g, 5.06 mmol, 1.2 equiv.) and Ruphos-2nd-precatlyst (130 mg) in 1,4-dioxane (10 mL) was stirred at 100° C. for 1 hour. The resulting mixture was extracted with EA (3×) and combined organic phase, then it was concentrated under vacuum to give the residue. The residue was purified by silica gel column chromatography, eluted with EA/PE (1:3) to afford methyl 2-fluoro-4-morpholinobenzoate (840 mg) as a yellow solid. ESI-MS m/z=240.10 [M+H]$^+$.

Example 12 Step b

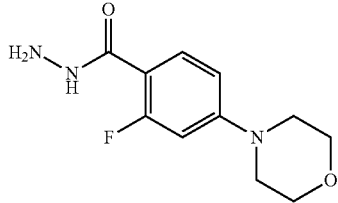 [SMILES: NNC(=O)c1ccc(N2CCOCC2)cc1F]

A solution of methyl 2-fluoro-4-morpholinobenzoate (840 mg, 3.51 mmol, 1 equiv.) and hydrazine hydrate (2 mL) in EtOH (2 mL) was stirred at 85° C. overnight. The resulting mixture was concentrated under vacuum. The residue was purified by silica gel column chromatography, eluted with CH$_2$Cl$_2$/MeOH (0 to 10:1) to afford the title compound (540 mg) as a dark gray solid. ESI-MS m/z=240.50 [M+H]$^+$.

Example 12 Step c

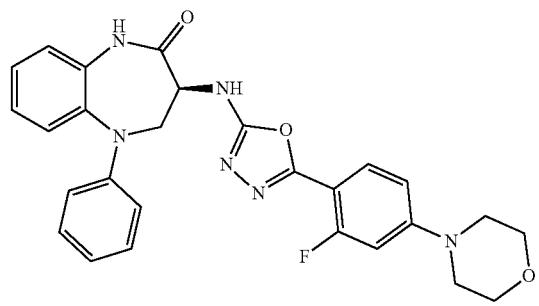 [SMILES: O=C1Nc2ccccc2N(c2ccccc2)C[C@@H]1Nc1nnc(-c2ccc(N3CCOCC3)cc2F)o1]

Prepared in a similar fashion to Example 6, step c using 2-fluoro-4-morpholinobenzohydrazide. ESI-MS m/z=501.25 [M+H]$^+$. $^1$H-NMR (300 MHz, DMSO-d$_6$): δ 3.28 (d, J=9.9 Hz, 4H), 3.74 (m, 4H), 3.94 (m, 1H), 4.18 (m, 1H), 4.35-4.51 (m, 1H), 6.65-6.75 (m, 2H), 6.79-6.98 (m, 3H), 7.23 (m, 6H), 7.64 (m, 1H), 8.23 (d, J=9.2 Hz, 1H), 10.11 (s, 1H).

Example 13

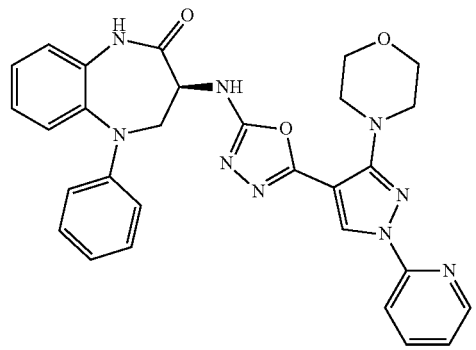 [SMILES: O=C1Nc2ccccc2N(c2ccccc2)C[C@@H]1Nc1nnc(-c2cn(-c3ccccn3)nc2N2CCOCC2)o1]

Example 13 Step a

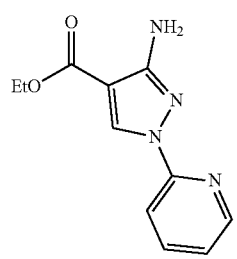 [SMILES: CCOC(=O)c1cn(-c2ccccn2)nc1N]

A solution of (E)-ethyl 2-cyano-3-ethoxyacrylate (1.69 g, 0.01 mol) in THF (5 mL) was dropwised to the solution of 2-hydrazinylpyridine (1.439 g, 0.013 mol) and NaOEt-EtOH (8.56 g, 0.026 mol) at 0° C. The mixture was stirred for 1.5 hours at 0° C. before quenched with 4 M HCl in 1,4-dioxane (6.5 mL, 0.026 mol). The solution was refluxed for 2 hours. It was adjusted pH=10-13 with 1 M NaOH and concentrated. The crude product was purified by Flash-Prep-HPLC (MeCN/H₂O) to give desired compound as an orange solid (1.07 g). ESI-MS m/z=233.25 [M+H]⁺. ¹H-NMR (300 MHz, DMSO-d₆): δ 1.29 (m, 3H), 4.24 (m, 2H), 7.32 (m, 1H), 7.71 (m, 1H), 7.97 (m, 1H), 8.43 (m, 1H), 8.67 (s, 1H).

Example 13 Step b

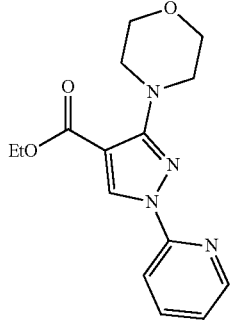 [SMILES: CCOC(=O)c1cn(-c2ccccn2)nc1N1CCOCC1]

NaH (202 mg, 8.4 mmol) was added to the solution of ethyl 3-amino-1-(pyridin-2-yl)-1H-pyrazole-4-carboxylate (970 mg, 4.2 mmol) in DMF (5 mL) at 0° C. The mixture was stirred for 10 minutes at 0° C. 1-bromo-2-(2-bromoethoxy)ethane (1.923 g, 8.4 mmol) was added, and the solution was stirred overnight. The mixture was quenched with water, extracted with EA (3×). The organic layers were combined and washed with brine (2×), dried and concentrated. The residue was chromatographied (silica, petroleum ether-ethyl acetate) to give desired compound as red oil (340 mg). ESI-MS m/z=303.30 [M+H]⁺.

Example 13 Step C

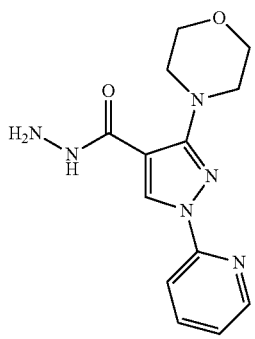 [SMILES: NNC(=O)c1cn(-c2ccccn2)nc1N1CCOCC1]

A solution of ethyl 3-morpholino-1-(pyridin-2-yl)-1H-pyrazole-4-carboxylate (340 mg, 1.122 mmol) and NH₂NH₂.H₂O (3 mL) in EtOH (4 mL) was refluxed overnight. The crude product was purified by Flash (MeCN/H₂O) to give desired compound as a white solid (280 mg). ESI-MS m/z=311.25 [M+H]⁺.

Example 13 Step d

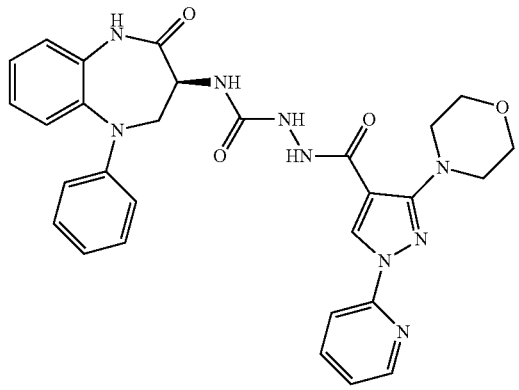 [SMILES: O=C(NNC(=O)c1cn(-c2ccccn2)nc1N1CCOCC1)N[C@H]1CN(c2ccccc2)c2ccccc2NC1=O]

Prepared in a similar fashion to Example 5 step d using 3-morpholino-1-(pyridin-2-yl)-1H-pyrazole-4-carbohydrazide. ESI-MS m/z=568.2 [M+H]⁺.

Example 13 Step e

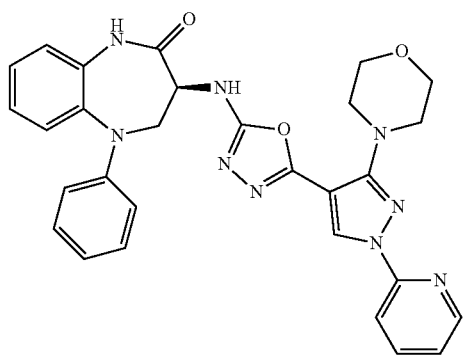 [SMILES: O=C1Nc2ccccc2N(c2ccccc2)C[C@@H]1Nc1nnc(-c2cn(-c3ccccn3)nc2N2CCOCC2)o1]

Prepared in a similar fashion to Example 5 step d using (S)-2-(3-morpholino-1-(pyridin-2-yl)-1H-pyrazole-4-carbonyl)-N-(4-oxo-1-phenyl-2,3,4,5-tetrahydro-1H-benzo[b][1,4]diazepin-3-yl)hydrazine-1-carboxamide. ESI-MS m/z=550.3 [M+H]⁺.

Example 14

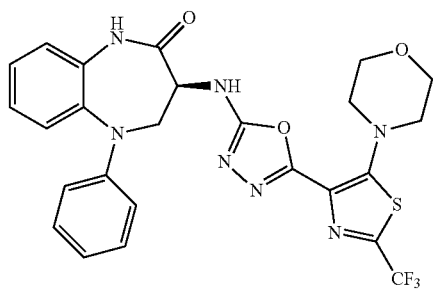 [SMILES: O=C1Nc2ccccc2N(c2ccccc2)C[C@@H]1Nc1nnc(-c2nc(C(F)(F)F)sc2N2CCOCC2)o1]

Example 14 Step a

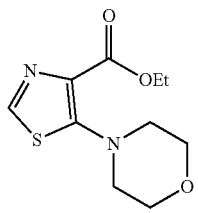 [SMILES: CCOC(=O)c1ncsc1N1CCOCC1]

In an oven-dried vial, ethyl 5-bromothiazole-4-carboxylate (200 mg, 0.88 mmol) was dissolved in MeCN (2.4 mL). Morpholine (87 uL, 0.99 mmol) and DBU (0.2 mL, 1.35 mmol) were added to the vial sequentially. The vial was sealed and heated to 80° C. for 5 hours. Cool the vial to room temperature and quench with water. Extract aqueous layer (3×) with EtOAc. The organic layer was dried with NaSO$_4$, filtered and concentrated. The crude product was purified on silica gel (hexane/EtOAc: 0% to 80%), affording ethyl 5-morpholinothiazole-4-carboxylate (120 mg) as a white solid. ESI-MS m/z=243.1 [M+H]$^+$.

Example 14 Step b

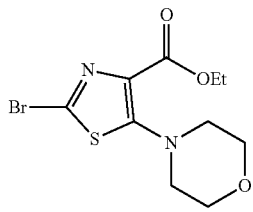 [SMILES: CCOC(=O)c1nc(Br)sc1N1CCOCC1]

To an oven-dried vial, ethyl 5-morpholinothiazole-4-carboxylate (247 mg, 1.06 mmol) was dissolved in MeCN (5.4 mL). N-bromosuccimide (208 mg, 1.17 mmol) was added to the vial in one portion at room temperature. The reaction was allowed to stir at room temperature until the starting material was consumed. The reaction mixture was concentrated and purified on silica gel (hexane/EtOAc: 0% to 80%), affording ethyl 2-bromo-5-morpholinothiazole-4-carboxylate (256 mg) as a white solid. ESI-MS m/z=322.2 [M+H]$^+$.

Example 14 Step c

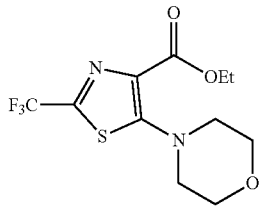 [SMILES: CCOC(=O)c1nc(C(F)(F)F)sc1N1CCOCC1]

To an oven-dried vial, ethyl 2-bromo-5-morpholinothiazole-4-carboxylate (650 mg, 2.02 mmol) was dissoved in DMF (10 mL). (1,10-Phenanthroline)(trifluoromethyl)copper (760 mg, 2.43 mmol) was added in one portion and the reaction mixture was heated at 80° C. overnight. The reaction mixture was cooled to room temperature and diluted with EtOAc. The organic layer was washed with H$_2$O (3×), brine and then dried with Na$_2$SO$_4$. The solid was filtered and the organic layer was concentrated to dryness. The residue was purified by column chromatography with 0-20% EtOAc in hexanes to give ethyl 5-morpholino-2-(trifluoromethyl)thiazole-4-carboxylate (360 mg). ESI-MS m/z=311.0 [M+H]$^+$.

Example 14 Step d

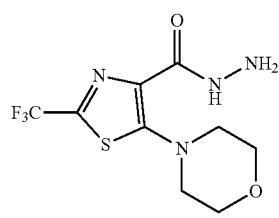 [SMILES: NNC(=O)c1nc(C(F)(F)F)sc1N1CCOCC1]

To a round-bottomed flask, ethyl 5-morpholino-2-(trifluoromethyl)thiazole-4-carboxylate (432 mg, 1.39 mmol) was dissolved in ethanol (4.64 mL) and hydrazine hydrate (2.32 mL) open to air to give a red solution. The reaction mixture was heated to 70° C. for 1 hour then cooled to room temperature. The reaction mixture was concentrated in vacuo. The crude product was added to a silica gel column and was eluted with methanol/dichloromethane 0% to 10% to give 5-morpholino-2-(trifluoromethyl)thiazole-4-carbohydrazide (367 mg) as a solid. ESI-MS m/z=297.1 [M+H]$^+$.

Example 14 Step e

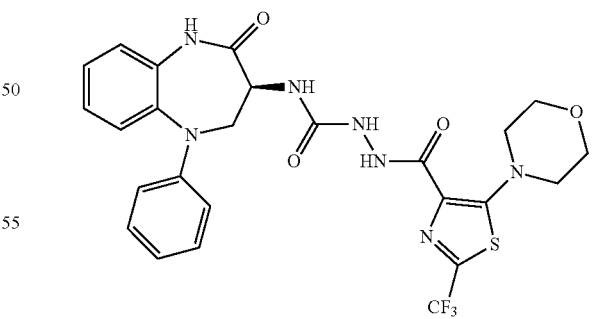

Prepared in a similar fashion to Example 6 step d using 5-morpholino-2-(trifluoromethyl)-thiazole-4-carbohydrazide. ESI-MS m/z=576.2 [M+H]$^+$.

Example 14 Step f

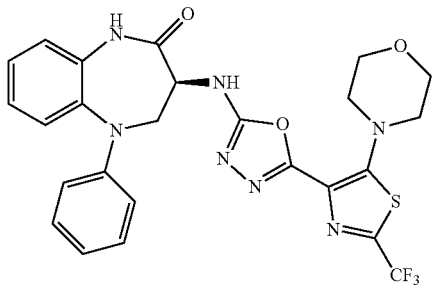 [SMILES: O=C1Nc2ccccc2N(c2ccccc2)C[C@@H]1Nc1nnc(-c2nc(C(F)(F)F)sc2N2CCOCC2)o1]

To a mixture of (S)-2-(5-morpholino-2-(trifluoromethyl)thiazole-4-carbonyl)-N-(4-oxo-1-phenyl-2,3,4,5-tetrahydro-1H-benzo[b][1,4]diazepin-3-yl)hydrazine-1-carboxamide (72 mg, 0.13 mmol) and triethylamine (52.3 µl, 0.38 mmol) in DCM (1.2 mL) was added phosphoryl trichloride (23.3 µl, 0.25 mmol) at 0° C. and stirred at room temperature for 15.5 hrs. The reaction was diluted with EtOAc, and then washed with H₂O, sat. NaHCO₃ solution and brine. The organic layer was dried (Na₂SO₄), filtered and concentrated to dryness. The residue was purified by silica gel column with 0~100% acetone in hexane to give (S)-3-((5-(5-morpholino-2-(trifluoromethyl)thiazol-4-yl)-1,3,4-oxadiazol-2-yl)amino)-5-phenyl-1,3,4,5-tetrahydro-2H-benzo[b][1,4]diazepin-2-one (2.6 mg). ESI-MS m/z=558.2 [M+H]⁺.

Example 15

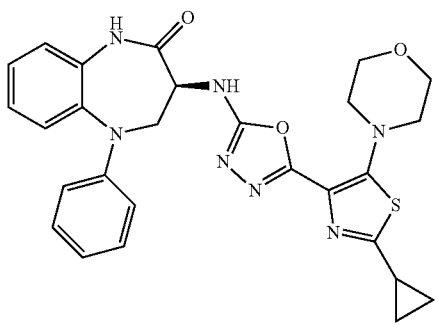 [SMILES: O=C1Nc2ccccc2N(c2ccccc2)C[C@@H]1Nc1nnc(-c2nc(C3CC3)sc2N2CCOCC2)o1]

Example 15 Step a

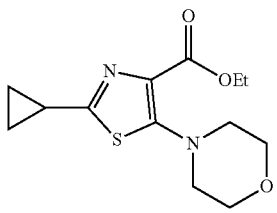 [SMILES: CCOC(=O)c1nc(C2CC2)sc1N1CCOCC1]

To a vial, add ethyl 2-bromo-5-morpholinothiazole-4-carboxylate (212 mg, 0.67 mmol), cyclopropylboronic acid (65 mg, 0.76 mmol), K₂CO₃ (286 mg, 2.07 mmol) and Pd(PPh₃)₄ (40 mg, 0.035 mmol). The vial was sealed and evacuated with nitrogen. Toluene (2.88 mL) and water (0.58 mL) were added to the vial with a syringe. The reaction mixture was heated to 80° C. and stirred at that temperature for 20 hours. The vial was cooled to room temperature and quenched with water. The aqueous layer was extracted (3×) with EtOAc. The organic layer was dried with Na₂SO₄, filtered and concentrated. The crude product was added to a silica gel column and was eluted with ethyl acetate/hexane 0% to 100% to give ethyl 2-cyclopropyl-5-morpholinothiazole-4-carboxylate (76 mg) as a solid. ESI-MS m/z=283.1 [M+H]⁺.

Example 15 Step b

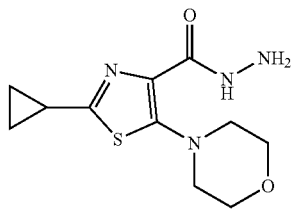 [SMILES: NNC(=O)c1nc(C2CC2)sc1N1CCOCC1]

Prepared in a similar fashion to Example 15, step d using ethyl 2-cyclopropyl-5-morpholinothiazole-4-carboxylate. ESI-MS m/z=269.2 [M+H]⁺.

Example 15 Step c

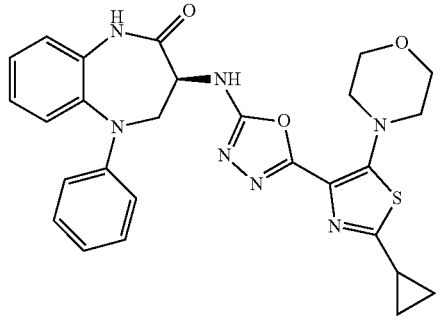 [SMILES: O=C1Nc2ccccc2N(c2ccccc2)C[C@@H]1Nc1nnc(-c2nc(C3CC3)sc2N2CCOCC2)o1]

To a solution of (S)-3-amino-5-phenyl-1,3,4,5-tetrahydro-2H-benzo[b][1,4]diazepin-2-one (47.2 mg, 0.186 mmol) in DMF (1165 µl) was added 1,1'-thiocarbonyldiimidazole (39.8 mg) and stirred for 1 hour. After an hour, 2-cyclopropyl-5-morpholinothiazole-4-carbohydrazide (50 mg, 0.186 mmol) and DMF (1165 µl) were added and the mixture was stirred for 2 hours. EDC (179 mg, 0.932 mmol) was added and the mixture was stirred for 4 hours at 60° C. The reaction mixture was diluted with water and extracted with EtOAc (3×). The organic layer was dried, filtered and concentrated. The crude product was added to a silica gel column and was eluted with acetone/hexane 0% to 50% to give the racemate as a yellow solid. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI-MS m/z=530.2 [M+H]⁺.

Example 16

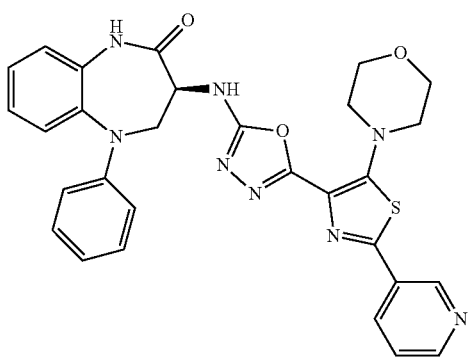 [SMILES: O=C1Nc2ccccc2N(c2ccccc2)C[C@@H]1Nc1nnc(-c2nc(-c3cccnc3)sc2N2CCOCC2)o1]

Example 16 Step a

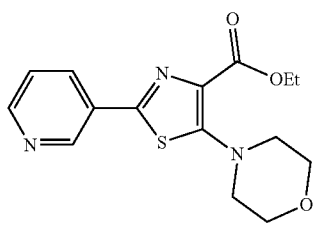 [SMILES: CCOC(=O)c1nc(-c2cccnc2)sc1N1CCOCC1]

Ethyl 2-bromo-5-morpholinothiazole-4-carboxylate (1 g, 3.11 mmol), pyridin-3-yl boronic acid (0.574 g, 4.67 mmol), Cs$_2$CO$_3$ (2.029 g, 6.23 mmol), and Pd(DPPF)Cl$_2$ (0.254 g, 0.311 mmol) were added to a oven-dried vial and sealed. The vial was evacuated and refilled with nitrogen. DMF (12.45 ml) was added through the septum via a syringe and the vial was heated to 90° C. overnight. The reaction mixture was cooled to room temperature and filtered through celite. The filtrate was concentrated in vacuo and the resultant crude residue was purified using column chromatography on silica gel (eluent: Hexane/EtOAc (4:1)) to provide ethyl 5-morpholino-2-(pyridin-3-yl)thiazole-4-carboxylate (222 mg). ESI-MS m/z=320.1 [M+H]$^+$.

Example 16 Step b

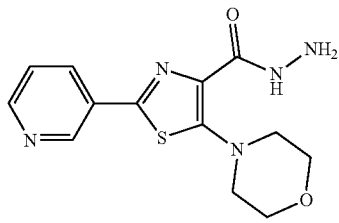 [SMILES: NNC(=O)c1nc(-c2cccnc2)sc1N1CCOCC1]

Prepared in a similar fashion to Example 15, step d using ethyl 5-morpholino-2-(pyridin-3-yl)thiazole-4-carboxylate. ESI MS m/z=306.2 [M+H]$^+$.

Example 16 Step c

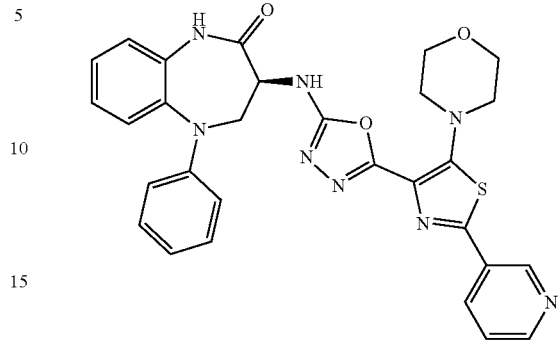

Prepared in a similar fashion to Example 15 step c using ethyl 5-morpholino-2-(pyridin-3-yl)thiazole-4-carboxylate. ESI-MS m/z=567.2 [M+H]$^+$.

Example 17

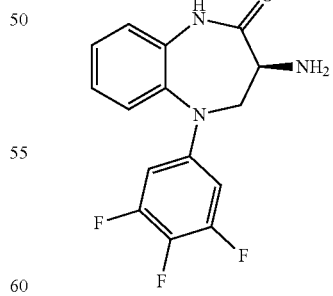

Example 17 Step a

Prepared in a similar fashion to Example 1 using 5-bromo-1,2,3-trifluorobenzene. ESI-MS m/z=308.2 [M+H]$^+$.

Example 17 Step b

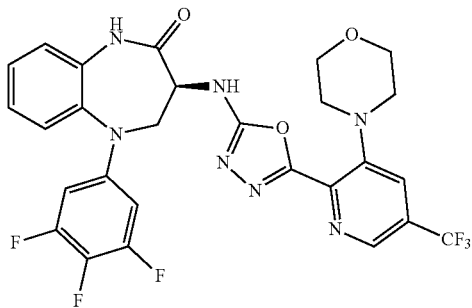 [SMILES: O=C1Nc2ccccc2N(c2cc(F)c(F)c(F)c2)C[C@@H]1Nc1nnc(-c2ncc(C(F)(F)F)cc2N2CCOCC2)o1]

Prepared in a similar fashion to Example 15 step c using (S)-3-amino-5-(3,4,5-trifluorophenyl)-1,3,4,5-tetrahydro-2H-benzo[b][1,4]diazepin-2-one and 3-morpholino-5-(trifluoromethyl)picolinohydrazide. ESI-MS m/z=606.3 [M+H]⁺.

Example 18

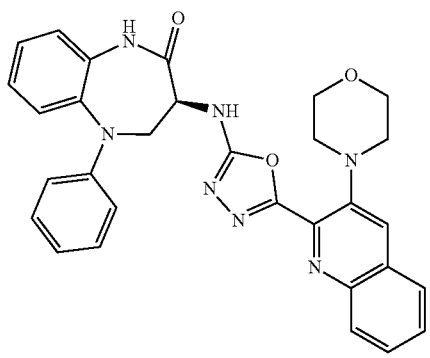 [SMILES: O=C1Nc2ccccc2N(c2ccccc2)C[C@@H]1Nc1nnc(-c2nc3ccccc3cc2N2CCOCC2)o1]

Example 18 Step a

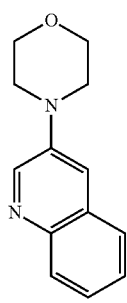

A solution of 3-bromoquinoline (2.0 g, 9.66 mmol, 1.0 equiv.), Ruphos (600 mg, 1.28 mmol, 0.13 equiv.), NaOBu-t (1.1 g, 11.6 mmol, 1.2 equiv.) and Ruphos $2^{nd}$ gen Pd precatlyst (372.8 mg, 0.48 mmol, 0.05 equiv.) in morpholine (30 mL) was stirred at 110° C. for 5 hours and then cooled to room temperature. The resulting mixture was extracted with EtOAc (3×) and the combined organic phase was dried over anhydrous Na₂SO₄, concentrated under vacuum. The residue was purified by silica gel column chromatography, eluted with EtOAc/PE (1:3) to afford 4-(quinolin-3-yl)morpholine (1.0 g, 4.9 mmol, 50%) as a yellow solid. ESI-MS m/z=215.20 [M+H]⁺.

Example 18 Step b

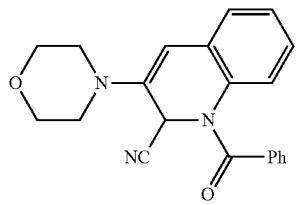 [SMILES: N#CC1C(N2CCOCC2)=Cc2ccccc2N1C(=O)c1ccccc1]

A solution of 4-(quinolin-3-yl)morpholine (1.0 g, 4.67 mmol, 1.0 equiv.) in DCM (30 mL) was added AlCl₃ (13.1 mg, 0.098 mmol, 0.013 equiv.). Benzoyl chloride (1.06 g, 7.56 mmol, 1.62 equiv.) was added dropwise. The mixture was stirred for 2 hours at room temperature and TMSCN (1.0 g, 7.5 mmol, 1.62 equiv.) was added. The resulting mixture was stirred overnight at room temperature. The mixture was diluted with DCM, washed with 1N HCl aqueous solution, saturated Na₂CO₃ aqueous solution, dried over anhydrous Na₂SO₄ and concentrated. The residue was purified by silica gel column chromatography, eluted with PE/EtOAc (0 to 5:1) to afford 1-benzoyl-3-morpholino-1,2-dihydroquinoline-2-carbonitrile (400 mg, 1.16 mmol, 25%) as a yellow solid.

Example 18 Step c

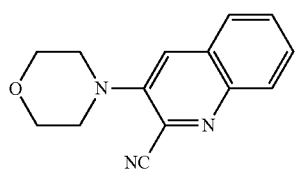 [SMILES: N#Cc1nc2ccccc2cc1N1CCOCC1]

A solution of 1-benzoyl-3-morpholino-1,2-dihydroquinoline-2-carbonitrile (400 mg, 1.16 mmol, 1 equiv.) in formic acid (10 mL) was stirred for 2 hours at room temperature. The resulting mixture was adjusted pH to 6 with saturated NaHCO₃ aqueous solution and extracted with EtOAc (3×). The combined organic phase was evaporated to afford 3-morpholinoquinoline-2-carbonitrile (250 mg, 1.05 mmol, 90%) as brown oil. ESI-MS m/z=240.10 [M+H]⁺.

Example 18 Step d

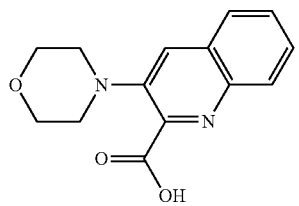 [SMILES: O=C(O)c1nc2ccccc2cc1N1CCOCC1]

A solution of 3-morpholinoquinoline-2-carbonitrile (250 mg, 1.05 mmol, 1 equiv.), KOH (291 mg, 2.1 mmol, 2 equiv.) and H₂O (2 mL) in EtOH (3 mL) was stirred for 6 hours at 100° C. The resulting mixture was cooled to room temperature, adjusted pH to 4 with HCl and extracted with EtOAc (3×). The combined organic phase was evaporated and purified by reverse phase column to afford 3-morpholinoquinoline-2-carboxylic acid (70 mg, 0.27 mmol, 26%) as yellow solid. ESI-MS m/z=259.25 [M+H]⁺.

Example 18 Step e

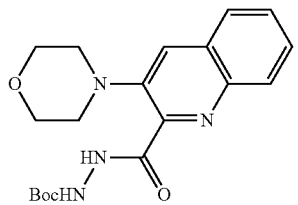 [SMILES: CC(C)(C)OC(=O)NNC(=O)c1nc2ccccc2cc1N1CCOCC1]

A solution of 3-morpholinoquinoline-2-carboxylic acid (70 mg, 0.27 mmol, 1 equiv.), tert-butyl hydrazinecarboxylate (36 mg, 0.27 mmol, 1 equiv.), DIPEA (35 mg, 0.54 mmol, 2 equiv.) and HATU (123 mg, 0.32 mmol, 1.2 equiv.) in DMF (3 mL) was stirred for 1 hour at room temperature. The resulting mixture was extracted with EtOAc (3×) and washed by water (3×). Then the combined organic phase was evaporated and purified by Prep-TLC to afford tert-butyl 2-(3-morpholinoquinoline-2-carbonyl)hydrazine-1-carboxylate (148 mg, crude) as brown oil. ESI-MS m/z=373.05 [M+H]⁺.

Example 18 Step f

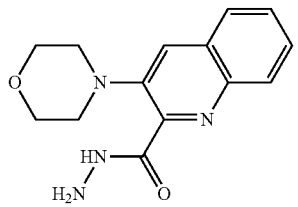 [SMILES: NNC(=O)c1nc2ccccc2cc1N1CCOCC1]

A solution of tert-butyl 2-(3-morpholinoquinoline-2-carbonyl)hydrazine-1-carboxylate (148 mg, 0.40 mmol, 1 equiv.) and HCl (0.25 mL) in EtOAc (2 mL) was stirred at room temperature for 1 hour. The resulting mixture was adjusted pH to 7 with saturated NaHCO₃ aqueous solution, extracted with DCM (3×), dried over anhydrous Na₂SO₄. The combined organic phase was evaporated to afford 3-morpholinoquinoline-2-carbohydrazide (120 mg, crude) as brown oil. ESI-MS m/z=273.05 [M+H]⁺.

Example 18 Step g

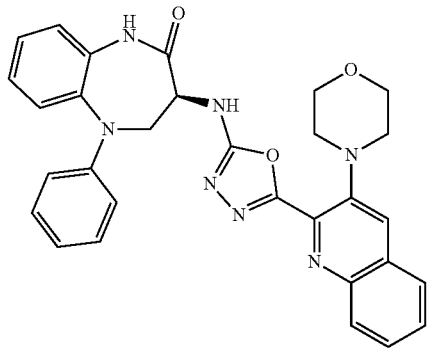 [SMILES: O=C1Nc2ccccc2N(c2ccccc2)C[C@@H]1Nc1nnc(-c2nc3ccccc3cc2N2CCOCC2)o1]

Prepared in a similar fashion to Example 15 step c using 3-morpholinoquinoline-2-carbohydrazide. ESI-MS m/z=534.30 [M+H]⁺. ¹H NMR (300 MHz, DMSO-d6) δ 3.05 (s, 4H), 3.77 (s, 4H), 3.93-4.01 (m, 1H), 4.18-4.27 (m, 1H), 4.52 (d, J=10.7 Hz, 1H), 6.72 (d, J=8.1 Hz, 2H), 6.86 (t, J=7.3 Hz, 1H), 7.16-7.35 (m, 6H), 7.62-7.75 (m, 2H), 7.99 (d, J=8.1 Hz, 2H), 8.10 (s, 1H), 8.56 (d, J=9.2 Hz, 1H), 10.16 (s, 1H).

Example 19

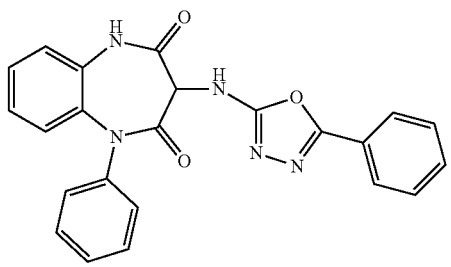 [SMILES: O=C1Nc2ccccc2N(c2ccccc2)C(=O)C1Nc1nnc(-c2ccccc2)o1]

Example 19 Step a

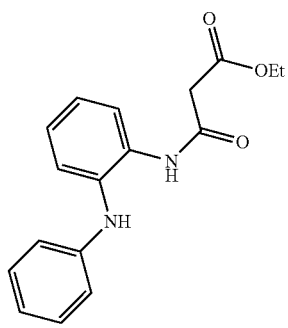 [SMILES: CCOC(=O)CC(=O)Nc1ccccc1Nc1ccccc1]

To a mixture of the N¹-phenylbenzene-1,2-diamine (10.0 g, 54 mmol), DIPEA (14.0 g108 mmol) and 3-ethoxy-3-oxopropanoic acid (7.2 g, 54 mmol) in DMF (100 mL) was added HATU (41.8 g, 108 mmol). The mixture was stirred at room temperature overnight. Then it was diluted with water, extracted by EtOAc and purified by silica gel column to afford the title compound as a red solid (8.0 g). ESI-MS m/z=299.25 [M+H]⁺.

Example 19 Step b

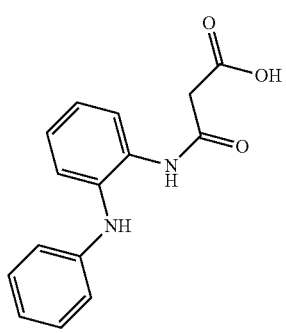 [SMILES: O=C(O)CC(=O)Nc1ccccc1Nc1ccccc1]

A solution of the compound from step a (7.0 g, 23.5 mmol) in THF/H₂O (40 mL/40 mL) was added LiOH (2.3 g, 94.0 mmol). The reaction mixture was stirred at RT for 1 hr. It was acidified by HCl, extracted by EA (×2), washed with saturated NaCl aqueous solution. The organic layer was dried and concentrated to give the desired compound as a white solid (6.2 g). ESI-MS m/z=271.20 [M+H]⁺.

Example 19 Step c

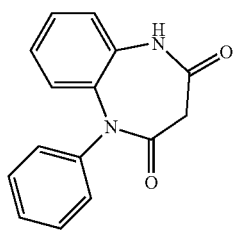 [SMILES: O=C1CC(=O)N(c2ccccc2)c2ccccc2N1]

A solution of the compound from step b (6.2 g, 23 mmol), EDCI (8.8 g, 46 mmol), HOBt (6.2 g, 46 mmol) in DMF (60 mL) was added DIEPA (5.9 g, 46 mmol). Then the reaction mixture was stirred overnight at RT. It was diluted with EA, washed with water (×2). The organic layer was dried and purified by recrystallization (PE/EA=1:1) to give the desired compound as a white solid (2.2 g). ESI-MS m/z=253.20 [M+H]⁺.

Example 19 Step d

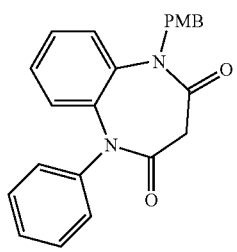

A solution of the compound from step c (2.2 g, 8.7 mmol), K₂CO₃ (2.4 g, 17.4 mmol) in DMF (20 mL) was added PMBCl (1.5 g, 10.5 mmol). Then the reaction mixture was stirred at RT overnight. LCMS showed that the reaction was complete. It was diluted with EA, washed with water (×2). The organic layer was dried and purified by recrystallization (PE/EtOAc=5:1) to give the desired compound as a white solid (2.5 g). ESI-MS m/z=373.30 [M+H]⁺.

Example 19 Step e

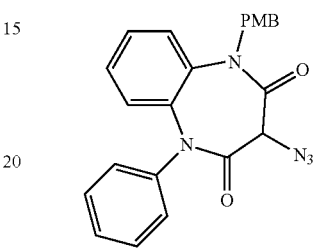

A solution of the compound from step d (2.5 g, 6.7 mmol) in THF (100 mL) was added tert-BuOK (1.5 g, 13.4 mmol) at −78° C., the reaction mixture was stirred for 30 min at −78° C. Then 2,4,6-triisopropylbenzenesulfonyl azide (3.1 g, 10.1 mmol) in THF (50 mL) was added dropwise into the reaction mixture at −78° C. After the addition, the reaction mixture was stirred at −78° C. for 10 mins. AcOH (1 mL) added and the reaction was warmed to RT overnight. It was purified by silica gel column and concentrated to give the title compound as a white solid (0.6 g). ESI-MS m/z=414.30 [M+H]⁺.

Example 19 Step f

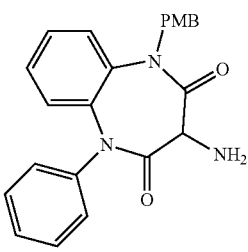

A solution of the compound from step e (0.6 g, 1.5 mmol) in MeOH/DCM (30 mL/30 mL) was added Pd/C (20 mg) at RT. Then the reaction was replaced H₂ three times and stirred for 30 min. The reaction mixture was filtered and the cake was washed with MeOH (×3), the filtrate was concentrated to give the title compound as a white solid (500 mg). ESI-MS m/z=388.35 [M+H]⁺.

Example 19 Step g

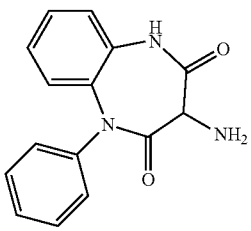 [SMILES: NC1C(=O)Nc2ccccc2N(c2ccccc2)C1=O]

A solution of the compound from step f (500 mg, 1.3 mmol) in MeCN/H₂O (8 mL/2 mL) was added CAN (7.1 g, 13 mmol) at 0° C. The reaction mixture was stirred at RT for 1 hr. It was diluted with H₂O, washed with EtOAc (×3), the aqueous phase was adjust pH=9 with saturated aqueous NaHCO₃ solution, then extracted with EA (×3) and the combined layer was concentrated to give the title compound as a yellow solid (180 mg). ESI-MS m/z=268.15 [M+H]$^+$.

Example 19 Step h

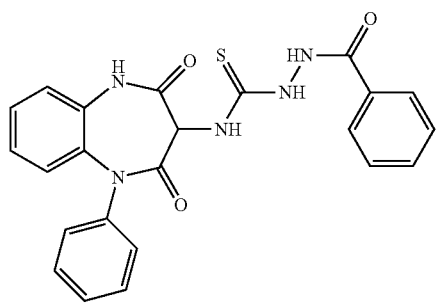 [SMILES: O=C(NNC(=S)NC1C(=O)Nc2ccccc2N(c2ccccc2)C1=O)c1ccccc1]

A solution of the compound from step g (60 mg, 0.23 mmol), 1,1'-thiocarbonyldiimidazole (48 mg, 0.27 mmol) in DMF (5 mL) was stirred for 30 minutes before benzohydrazide (100 mg, 0.69 mmol) was added. And it was stirred for 30 minutes. It was concentrated to give the title compound as yellow oil, which was used directly for the next step. ESI-MS m/z=446.05 [M+H]$^+$.

Example 19 Step i

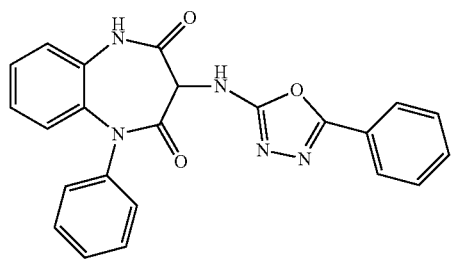 [SMILES: O=C1Nc2ccccc2N(c2ccccc2)C(=O)C1Nc1nnc(-c2ccccc2)o1]

A solution of the compound from step h (crude) and EDCI (52 mg, 0.27 mmol) in DMF (5 mL) was stirred for 30 minutes at 60° C. It was purified by Prep-HPLC (MeCN/H₂O) to give the title compound as a light solid (20.3 mg). ESI-MS m/z=412.10 [M+H]$^+$. $^1$H NMR (300 MHz, DMSO-d₆): δ 5.09 (d, J=7.8 Hz, 1H), 6.97 (d, J=8.2 Hz, 1H), 7.17-7.29 (m, 3H), 7.32-7.44 (m, 3H), 7.49 (m, 2H), 7.53-7.63 (m, 3H), 7.80-7.89 (m, 2H), 8.58 (d, J=8.2 Hz, 1H), 11.09 (s, 1H).

Example 20

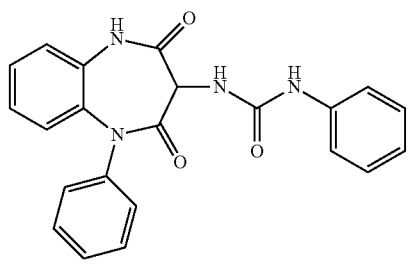 [SMILES: O=C(Nc1ccccc1)NC1C(=O)Nc2ccccc2N(c2ccccc2)C1=O]

Example 20 was prepared from the compound (step g in example 18) and phenyl isocyanate. ESI-MS m/z=387.30 [M+H]$^+$.

Example 21

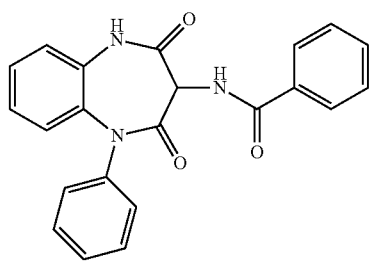 [SMILES: O=C(NC1C(=O)Nc2ccccc2N(c2ccccc2)C1=O)c1ccccc1]

A solution of the compound from step g in example 19 (60 mg, 0.23 mmol), TEA (47 mg, 0.43 mmol) in DCM (2 mL) was added BzCl (39 mg, 0.28 mmol) at RT. The reaction mixture was stirred at RT for 1 hr. LCMS showed that the starting material was consumed. It was purification by prep-HPLC to give desired compound as a white solid (18.5 mg). ESI-MS m/z=372.30 [M+H]$^+$.

Assays

Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focusses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% (TCID50) using 8,000 cells per well and 3-fold viral dilutions across a 96-well plate, cultured for 4 days.

Following extensive parameter testing, the final assay is run as follows: HEp-2 cells are seeded into the inner 60 wells of a 96-well plate at 8,000 cells per well in a volume of 50 using Growth Media (DMEM without phenol red, 1% L-Glut, 1% Penn/Strep, 1% nonessential amino acids, 10% FBS). 2-fold serial dilutions of control and test compounds are added to the wells in duplicate in a total volume of 25 μL. Viral stock is then added to the wells in a volume of 25 μL, bringing the total volume of each well to 100 μL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 μL of growth media to act as a thermal and evaporative moat around the test wells. Following a 4-day incubation period, the plates are read using ATPlite (50 uL added per well), which quantifies the amount of ATP (a measure of cell health) present in each well. Assay plates are read using the Envision luminometer. These data are used to calculate the $EC_{50}$ of each compound. $EC_{50}$ ranges are as follows: A<2 μM; B 2-5 μM; C>5 μM.

TABLE 2

Summary of Activities

| Example | Human RSV-A ("Long" strain) $EC_{50}$ |
|---|---|
| 1 | C |
| 2 | C |
| 3 | C |
| 4 | C |
| 5 | A |
| 6 | B |
| 7 | A |
| 8 | C |
| 9 | C |
| 10 | A |
| 11 | C |
| 12 | C |
| 13 | B |
| 14 | A |
| 15 | A |
| 16 | A |
| 17 | C |
| 19 | C |
| 20 | C |
| 21 | C |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I), or a pharmaceutically acceptable salt thereof:

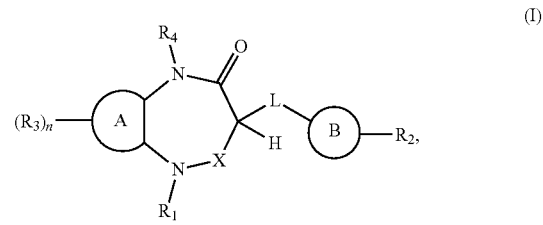

wherein:
A is selected from the group consisting of:
  1) Optionally substituted heteroaryl; and
  2) Optionally substituted aryl;
B is selected from the group consisting of:
  1) Optionally substituted heteroaryl; and
  2) Optionally substituted aryl;
L is —NH—;
X is —$CH_2$—, or —C(O)—;
$R_1$ is selected from the group consisting of:
  1) Optionally substituted heteroaryl; and
  2) Optionally substituted aryl;
$R_2$ is absent or is selected from the group consisting of:
  1) Optionally substituted —$C_1$-$C_8$ alkyl;
  2) Optionally substituted —$C_2$-$C_8$ alkenyl;
  3) Optionally substituted —$C_2$-$C_8$ alkynyl;
  4) Optionally substituted —$C_1$-$C_8$ alkoxy;
  5) Optionally substituted aryloxy;
  6) Optionally substituted —$C_3$-$C_{12}$ cycloalkyl;
  7) Optionally substituted —$C_3$-$C_{12}$ cycloalkenyl;
  8) Optionally substituted 3- to 12-membered heterocycloalkyl;
  9) Optionally substituted aryl;
  10) Optionally substituted arylalkyl;
  11) Optionally substituted heteroaryl;
  12) Optionally substituted heteroarylalkyl;
  13) —$NR_{13}R_{14}$;
  14) —CO—$NR_{13}R_{14}$; and
  15) —$SO_2$—$NR_{13}R_{14}$;
Each $R_3$ is independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —NH$C_1$-$C_8$ alkyl, optionally substituted —S—(—$C_1$-$C_8$ alkyl), optionally substituted —$SO_2$—(—$C_1$-$C_8$ alkyl), -optionally substituted —$SO_2$—NH—(—$C_1$-$C_8$ alkyl), optionally substituted —NH—$SO_2$—(—$C_1$-$C_8$ alkyl), —$CO_2R_{12}$, —$NR_{13}R_{14}$, and —CO—$NR_{13}R_{14}$;
$R_{12}$ is selected from the group consisting of:
  1) Optionally substituted —$C_1$-$C_8$ alkyl;
  2) Optionally substituted —$C_2$-$C_8$ alkenyl;
  3) Optionally substituted —$C_2$-$C_8$ alkynyl;
  4) Optionally substituted —$C_3$-$C_8$ cycloalkyl;
  5) Optionally substituted —$C_3$-$C_8$ cycloalkenyl;
  6) Optionally substituted 3- to 8-membered heterocycloalkyl;
  7) Optionally substituted aryl; and
  8) Optionally substituted heteroaryl;

R$_{13}$ and R$_{14}$ are each independently selected from hydrogen, optionally substituted —C$_1$-C$_8$-alkyl, optionally substituted —C$_2$-C$_8$-alkenyl, optionally substituted —C$_2$-C$_8$-alkynyl; optionally substituted —C$_3$-C$_8$-cycloalkyl; optionally substituted —C$_3$-C$_8$ cycloalkenyl; optionally substituted 3- to 12-membered heterocycloalkyl, optionally substituted aryl; optionally substituted heteroaryl; optionally substituted —C$_1$-C$_8$-alkoxy, —C(O)R$_{12}$, —S(O)$_2$R$_{12}$, and —S(O)$_2$NHR$_{12}$;
alternatively, R$_{13}$ and R$_{14}$ are taken together with the nitrogen atom to which they are attached to form an optionally substituted heterocyclic ring;
R$_4$ is selected from hydrogen and —C$_1$-C$_8$ alkyl; and
n is 0 to k, wherein k is the total number of CH and NH groups in A when A is unsubstituted.

2. The compound of claim 1, represented by Formula (Ib) or a pharmaceutically acceptable salt thereof:

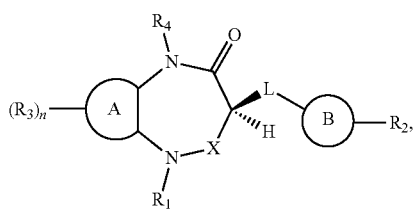

(Ib)

wherein R$_1$, R$_2$, R$_3$, R$_4$, A, B, L, X, and n are as defined in claim 1.

3. The compound of claim 1, represented by Formula (III-1) or a pharmaceutically acceptable salt thereof:

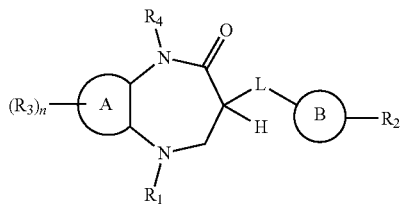

(III-1)

wherein R$_1$, R$_2$, R$_3$, R$_4$, A, B, L, and n are as defined in claim 1.

4. The compound of claim 1, wherein A is selected from one of the following by removal of hydrogen atoms from two adjacent ring carbon atoms:

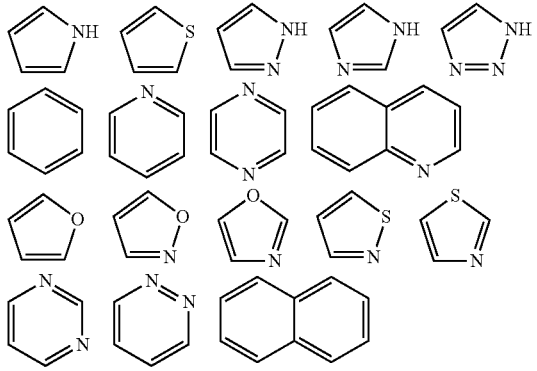

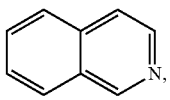

wherein each of the above shown is optionally substituted with one or more substituents which are not R$_3$ when possible.

5. The compound of claim 1, wherein B is selected from one of the following by removal of one or two hydrogen atoms:

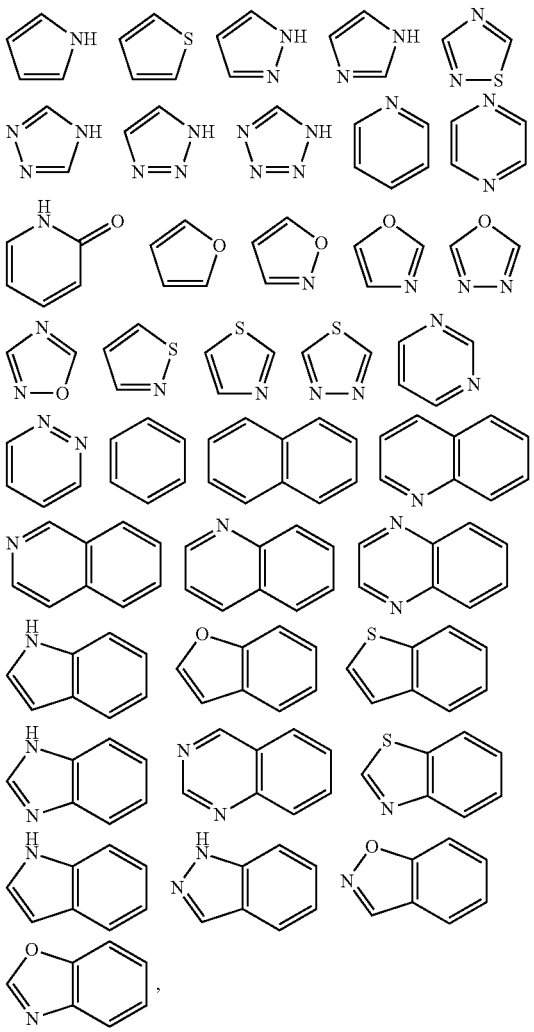

wherein each of the above shown is optionally substituted when it is possible.

6. The compound of claim 1, wherein R$_2$ is selected from one of the following by removal of one ring hydrogen atom:

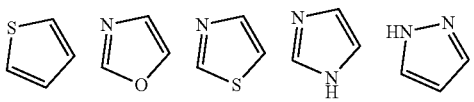

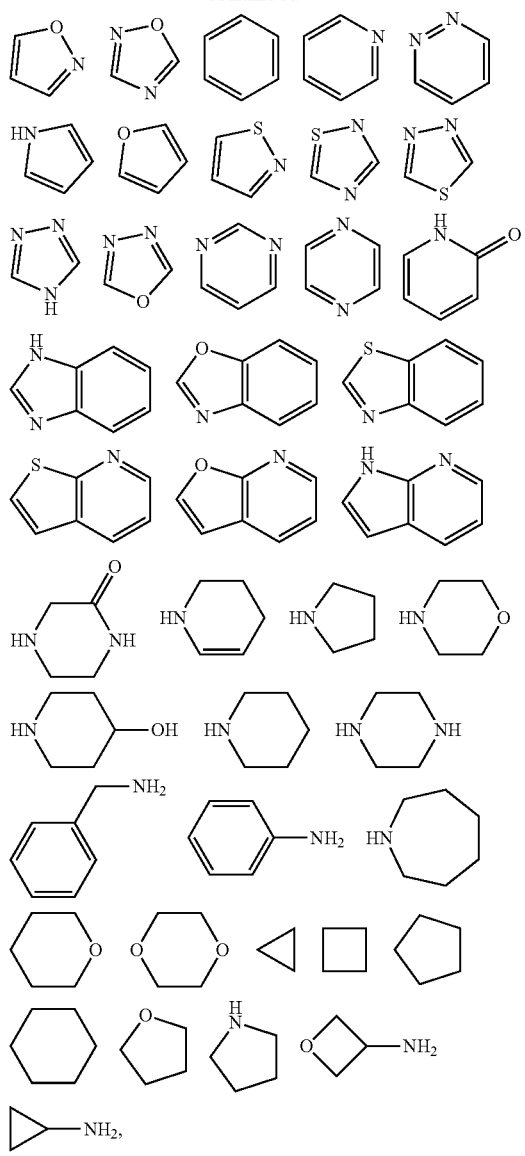
wherein each of the above shown is optionally substituted.
7. The compound of claim 1, wherein $R_2$ is selected from the following:
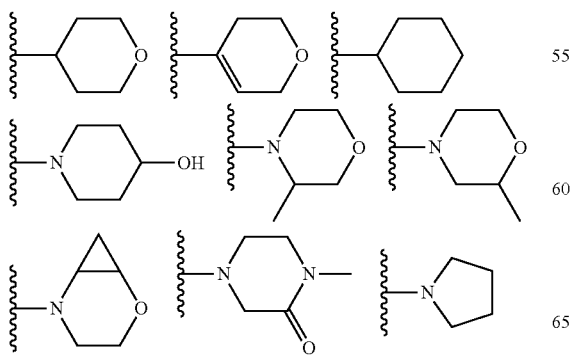
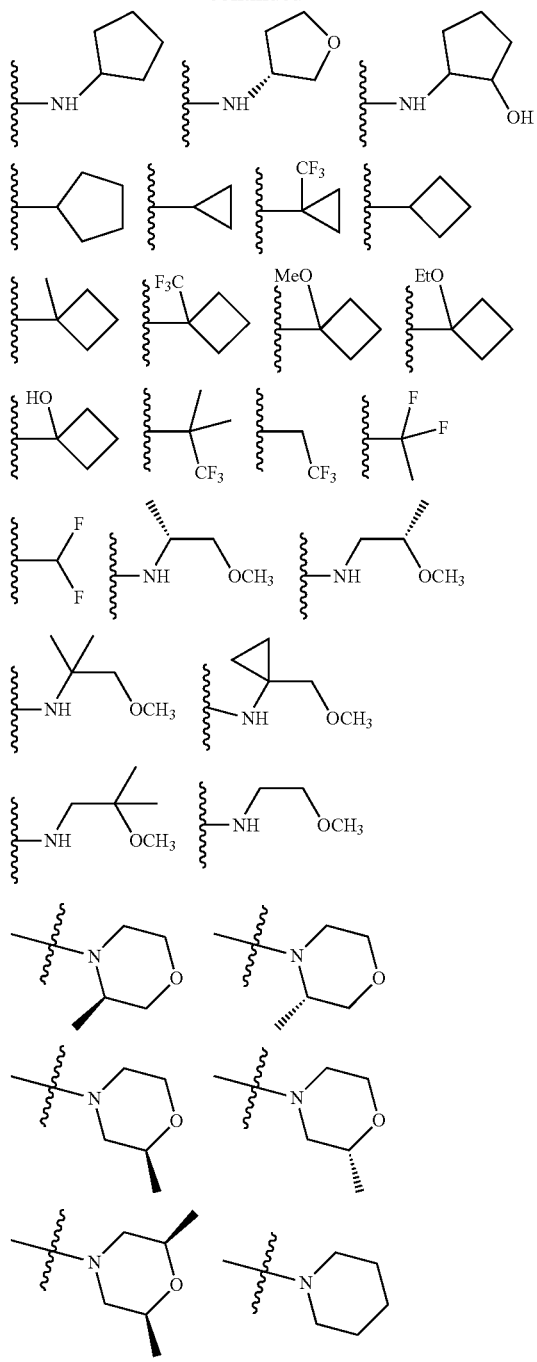
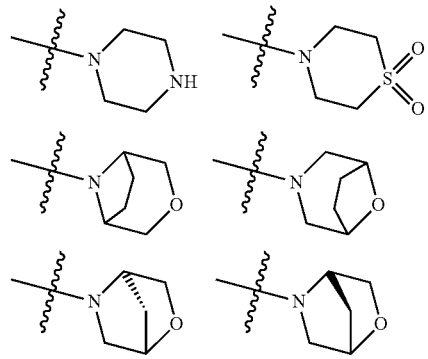

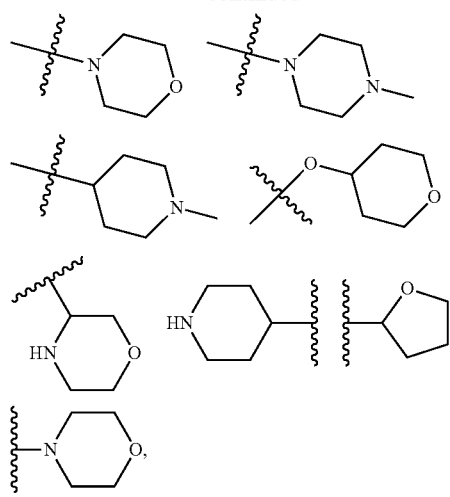
wherein each group is optionally substituted.
8. The compound of claim 1, wherein $R_2$ is selected from the groups set forth in Table 1:

TABLE 1-continued
| Entry | R₂ |
|---|---|
| 17 | 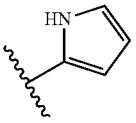 |
| 18 | 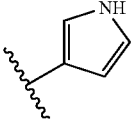 |
| 19 | 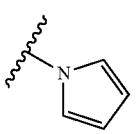 [SMILES: *n1cccc1] |
| 20 | 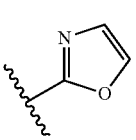 |
| 21 | 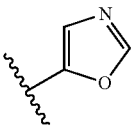 |
| 22 | 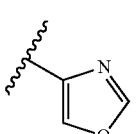 |
| 23 | 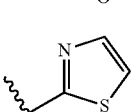 |
| 24 | 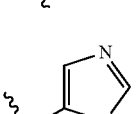 |
| 25 | 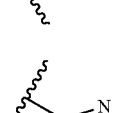 |
| 26 | 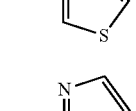 |
| 27 | 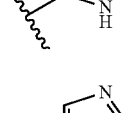 |
| 28 | 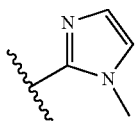 [SMILES: *c1nccn1C] |
| 29 |  |
| 30 |  |
| 31 | 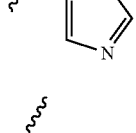 |
| 32 | 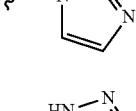 |
| 33 | 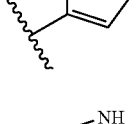 |
| 34 | 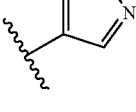 |
| 35 | 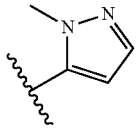 [SMILES: *c1ccnn1C] |
| 36 | 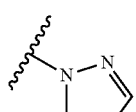 |
| 37 | 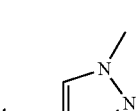 |

TABLE 1-continued

| Entry | R₂ |
|---|---|
| 38 | isoxazol-5-yl |
| 39 | isothiazol-4-yl |
| 40 | isothiazol-3-yl |
| 41 | isothiazol-5-yl |
| 42 | isoxazol-4-yl |
| 43 | 1,2,4-oxadiazol-3-yl |
| 44 | 1,3,4-oxadiazol-2-yl (O-N=) |
| 45 | 1,2,4-thiadiazol-3-yl |
| 46 | 1,3,4-thiadiazol-2-yl |
| 47 | 1,3,4-oxadiazol-2-yl |
| 48 | 1,3,4-thiadiazol-2-yl |

TABLE 1-continued

| Entry | R₂ |
|---|---|
| 49 | 4H-1,2,4-triazol-3-yl |
| 50 | 4-methyl-4H-1,2,4-triazol-3-yl |
| 51 | 4H-1,2,4-triazol-4-yl |
| 52 | pyridin-4-yl |
| 53 | pyridazin-3-yl |
| 54 | pyridazin-4-yl |
| 55 | pyrimidin-4-yl |
| 56 | pyrazin-2-yl |
| 57 | pyrimidin-2-yl |
| 58 | pyrimidin-5-yl |

TABLE 1-continued
| Entry | R₂ |
|---|---|
| 59 | 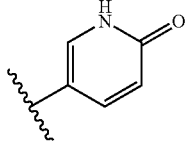 [SMILES: *c1ccc(=O)[nH]c1] |
| 60 | 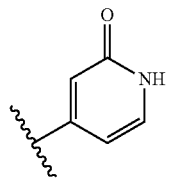 [SMILES: *c1cc[nH]c(=O)c1] |
| 61 | 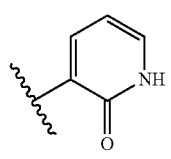 [SMILES: *c1ccc[nH]c1=O] |
| 62 | 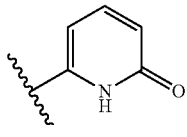 [SMILES: *c1cccc(=O)[nH]1] |
| 63 | 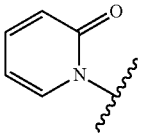 [SMILES: *n1ccccc1=O] |
| 64 | 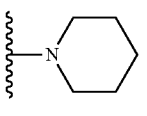 |
| 65 | 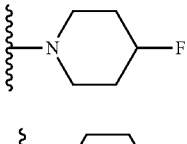 |
| 66 | 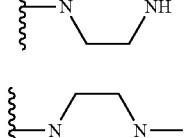 |
| 67 | 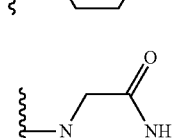 |
| 68 | 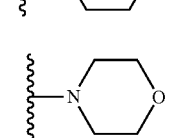 |
| 69 | 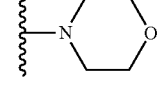 |
| 70 | 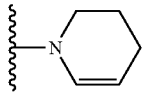 |
| 71 | 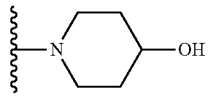 |
| 72 | 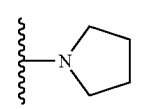 |
| 73 | 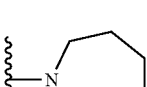 |
| 74 | 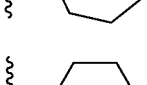 |
| 75 | 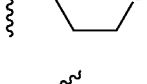 |
| 76 | 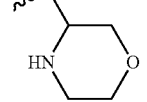 |
| 77 |  |
| 78 | 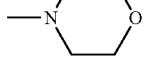 |
| 79 | 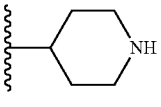 |
| 80 | 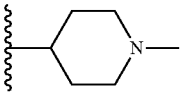 |
| 81 | 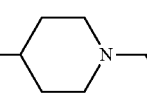 |
| 82 | 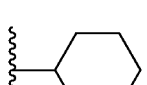 |

TABLE 1-continued

| Entry | R₂ |
|---|---|
| 83 | tetrahydrofuran-2-yl |
| 84 | pyrrolidin-2-yl (NH) |
| 85 | pyrrolidin-3-yl (NH) |
| 86 | 1-methylpyrrolidin-3-yl |
| 87 | 1-methylpyrrolidin-2-yl |
| 88 | -NH-CH₂-phenyl |
| 89 | -NH-cyclopropyl |
| 90 | -NH-phenyl |
| 91 | -NH-(oxetan-3-yl) |
| 92 | -CH₂-phenyl |
| 93 | -C(O)-NH-(3-fluorophenyl) |

TABLE 1-continued

| Entry | R₂ |
|---|---|
| 94 | -S(O)₂-NH-methyl |
| 95 | 4-methoxyphenyl |
| 96 | 3-methoxyphenyl |
| 97 | -C(O)-piperidin-1-yl |
| 98 | 2-methoxyphenyl |
| 99 | 3-methoxy-4-fluorophenyl |
| 100 | 2,3-difluorophenyl |
| 101 | 3,4-difluorophenyl |
| 102 | 4-chlorophenyl |

TABLE 1-continued

| Entry | R₂ |
|---|---|
| 103 | 4-CF₃-phenyl |
| 104 | 4-CN-phenyl |
| 105 | 4-OCF₃-phenyl |
| 106 | 4-SO₂Me-phenyl |
| 107 | 4-SO₂NH₂-phenyl |
| 108 | 4-(pyrazol-1-yl)-phenyl |
| 109 | 4-Me-phenyl |
| 110 | 3-Me-phenyl |
| 111 | 3-Cl-phenyl |

TABLE 1-continued

| Entry | R₂ |
|---|---|
| 112 | 3-CF₃-phenyl |
| 113 | 3-CN-phenyl |
| 114 | 3-OCF₃-phenyl |
| 115 | 3-SO₂Me-phenyl |
| 116 | 3-O-iPr-phenyl |
| 117 | 3-(2-methoxyethoxy)-phenyl |
| 118 | 5-fluoropyridin-2-yl |
| 119 | 5-(trifluoromethyl)pyridin-2-yl |

TABLE 1-continued
| Entry | R₂ |
|---|---|
| 120 | 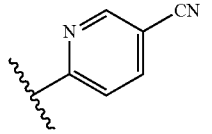 [SMILES: *c1ccc(C#N)cn1] |
| 121 | 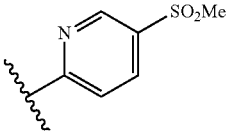 [SMILES: *c1ccc(S(C)(=O)=O)cn1] |
| 122 | 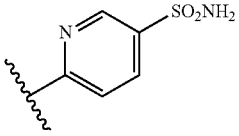 |
| 123 | 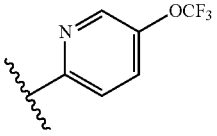 [SMILES: *c1ccc(OC(F)(F)F)cn1] |
| 124 | 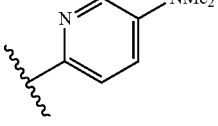 |
| 125 | 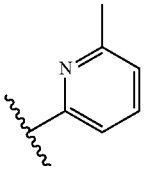 [SMILES: *c1cccc(C)n1] |
| 126 | 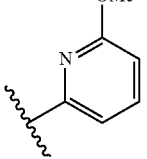 |
| 127 | 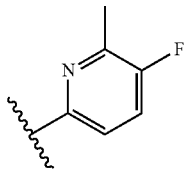 [SMILES: *c1ccc(F)c(C)n1] |
| 128 | 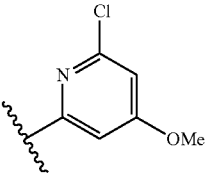 [SMILES: *c1cc(OC)cc(Cl)n1] |
| 129 | 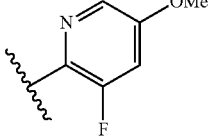 |
| 130 | 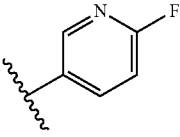 [SMILES: *c1ccc(F)nc1] |
| 131 | 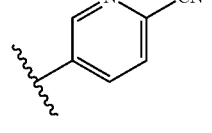 |
| 132 | 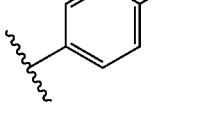 |
| 133 | 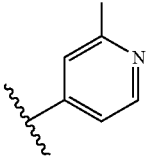 |
| 134 | 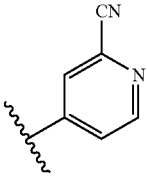 [SMILES: *c1ccnc(C#N)c1] |
| 135 | 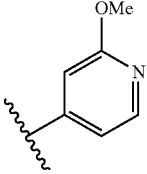 [SMILES: *c1ccnc(OC)c1] |
| 136 | 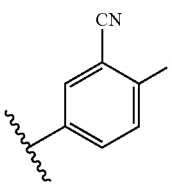 |
| 137 | 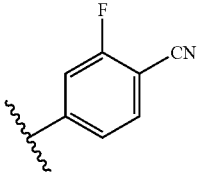 [SMILES: *c1ccc(C#N)c(F)c1] |

TABLE 1-continued

| Entry | R₂ |
|---|---|
| 138 | 3-methyl-4-cyanophenyl |
| 139 | 1-oxoisoindolin-5-yl |
| 140 | 1H-benzimidazol-5-yl |
| 141 | 3-cyano-1H-indol-6-yl |
| 142 | benzothiazol-6-yl |
| 143 | thieno[2,3-b]pyridin-2-yl |
| 144 | 5-methyl-4,5,6,7-tetrahydrothiazolo[5,4-c]pyridin-2-yl |
| 145 | 5-cyanothiophen-2-yl |
| 146 | 5-(trifluoromethyl)thiophen-2-yl |

TABLE 1-continued

| Entry | R₂ |
|---|---|
| 147 | N-phenylcarbamoyl |
| 148 | 5-(trifluoromethyl)-3-morpholinopyridin-2-yl |
| 149 | 5-cyano-3-morpholinopyridin-2-yl |
| 150 | 5-fluoro-3-morpholinopyridin-2-yl |
| 151 | 4-cyano-2-morpholinophenyl |
| 152 | 6-methyl-2-morpholinopyridin-3-yl |

TABLE 1-continued
| Entry | R2 |
|---|---|
| 153 | 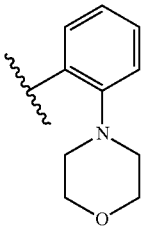 [SMILES: *c1ccccc1N1CCOCC1] |
| 154 | 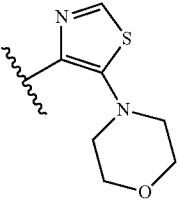 [SMILES: *c1ncsc1N1CCOCC1] |
| 155 | 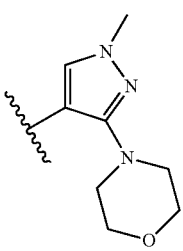 [SMILES: *c1cn(C)nc1N1CCOCC1] |
| 156 | 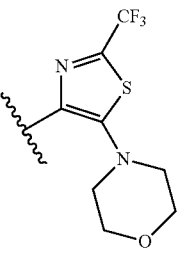 [SMILES: *c1nc(C(F)(F)F)sc1N1CCOCC1] |
| 157 | 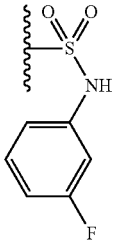 |
| 158 | 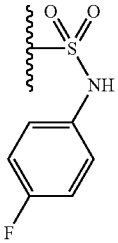 [SMILES: *S(=O)(=O)Nc1ccc(F)cc1] |
| 159 | 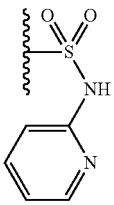 [SMILES: *S(=O)(=O)Nc1ccccn1] |
| 160 | 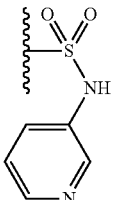 |
| 161 | 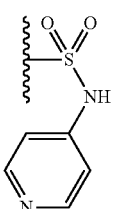 |
| 162 | 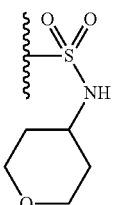 |
| 163 | 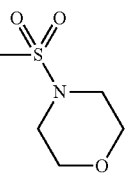 |
| 164 | 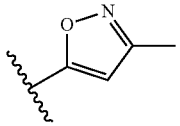 [SMILES: *c1cc(C)no1] |
| 165 | 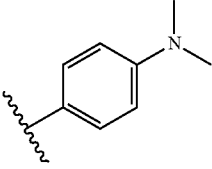 [SMILES: *c1ccc(N(C)C)cc1] |
| 166 | 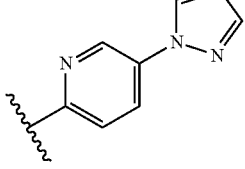 |

TABLE 1-continued
| Entry | R₂ |
|---|---|
| 167 | 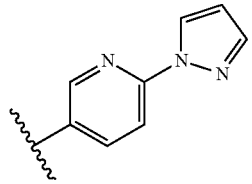 [SMILES: *c1ccc(-n2cccn2)nc1] |
| 168 | 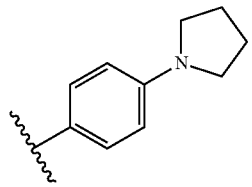 [SMILES: *c1ccc(N2CCCC2)cc1] |
| 169 | 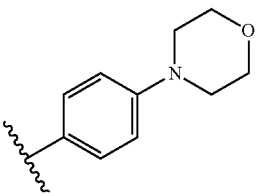 [SMILES: *c1ccc(N2CCOCC2)cc1] |
| 170 | 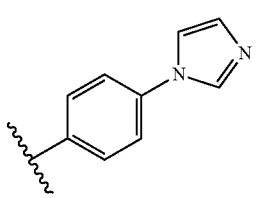 [SMILES: *c1ccc(-n2ccnc2)cc1] |
| 171 | 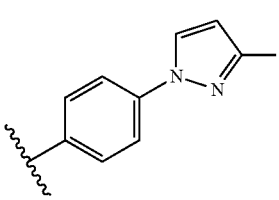 |
| 172 | 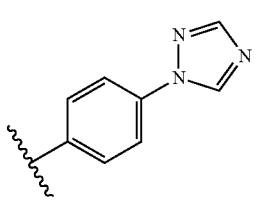 [SMILES: *c1ccc(-n2cncn2)cc1] |
| 173 | 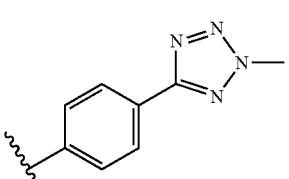 |
| 174 | 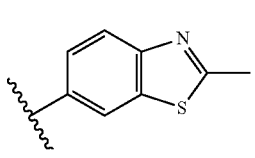 [SMILES: *c1ccc2nc(C)sc2c1] |
TABLE 1-continued
| Entry | R₂ |
|---|---|
| 175 | 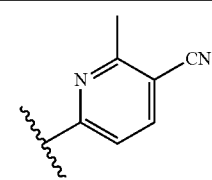 |
| 176 | 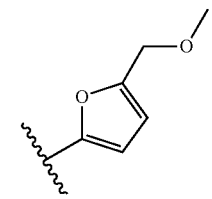 [SMILES: *c1ccc(COC)o1] |
| 177 | 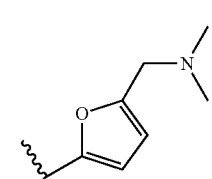 |
| 178 |  |
| 179 | 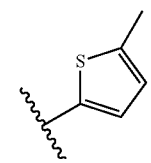 [SMILES: *c1ccc(C)s1] |
| 180 | 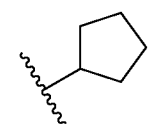 [SMILES: *C1CCCC1] |
| 181 | 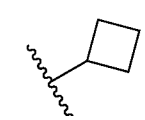 [SMILES: *C1CCC1] |
| 182 | 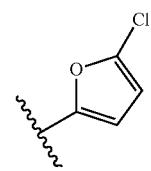 [SMILES: *c1ccc(Cl)o1] |
| 183 | 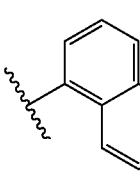 |

TABLE 1-continued

| Entry | R₂ |
|---|---|
| 184 | naphthalen-2-yl |
| 185 | -S(O)₂-N(CH₃)₂ |
| 186 | -S(O)₂-NH-cyclopropyl |

9. A compound selected from the compounds set forth below or a pharmaceutically acceptable salt thereof:

| Compound | Structure |
|---|---|
| 1 | (structure) |
| 2 | (structure) |
| 4 | (structure) |
| 5 | (structure) |
| 6 | (structure) |
| 7 | (structure) |
| 8 | (structure) |
| 9 | (structure) |

| Compound | Structure |
|---|---|
| 10 | 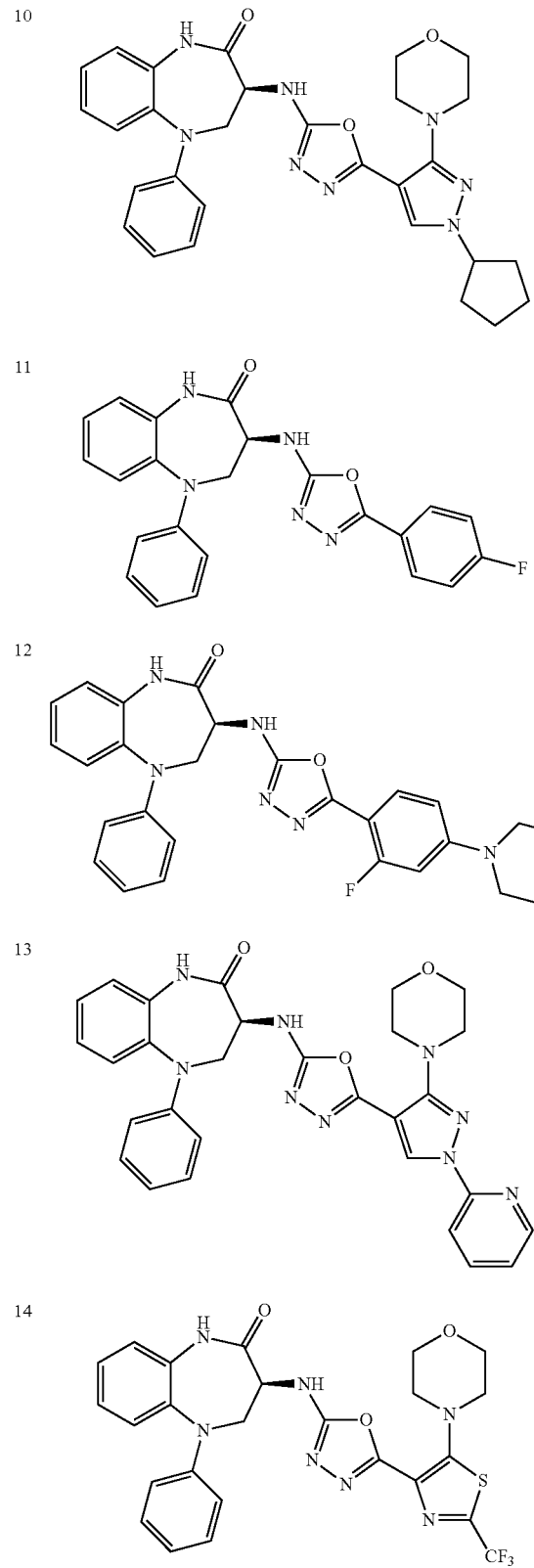 |
| 11 | |
| 12 | |
| 13 | |
| 14 | |
| Compound | Structure |
|---|---|
| 15 | 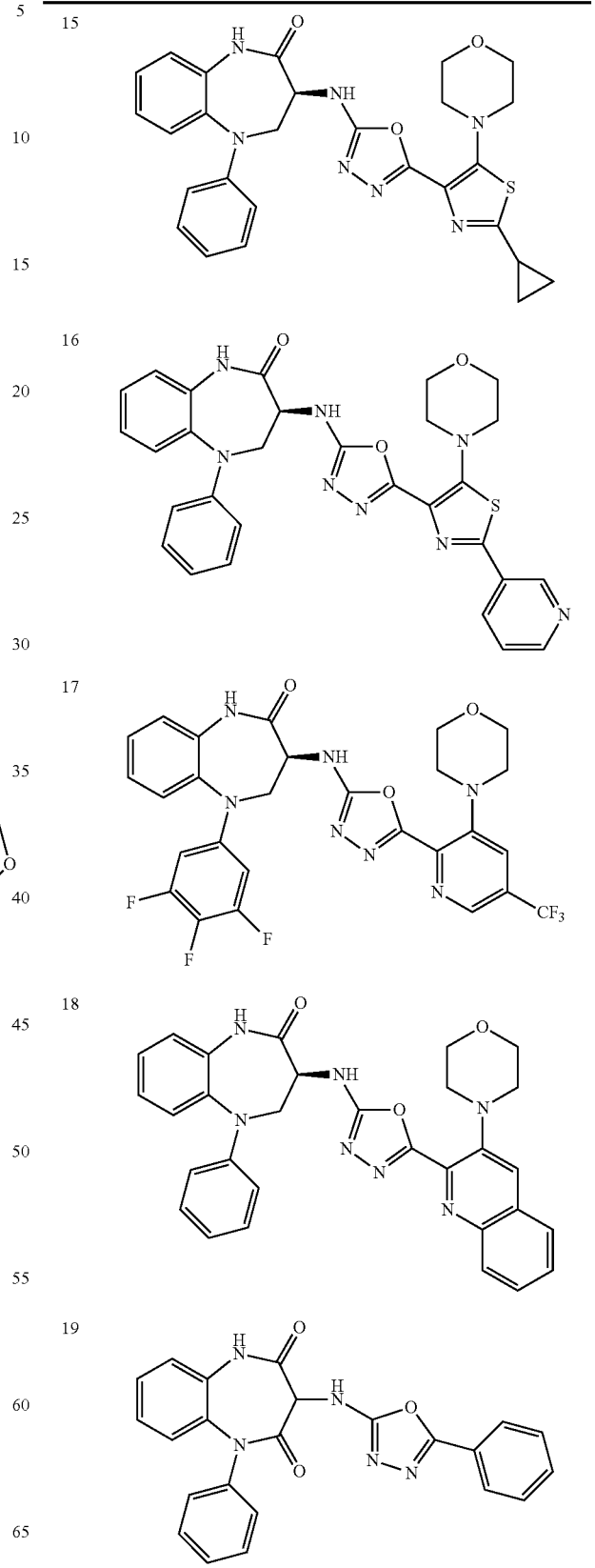 |
| 16 | |
| 17 | |
| 18 | |
| 19 | |

| Compound | Structure |
|---|---|
| 21 | 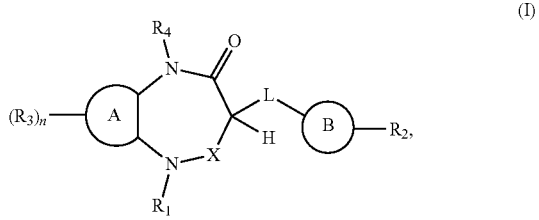 |

10. A pharmaceutical composition comprising a compound according to claim 1, in combination with a pharmaceutically acceptable carrier, diluent or excipient.

11. A method of treating or preventing an RSV infection in a subject in need thereof, comprising administering to the subject a therapeutically effective amount of a compound represented by Formula (I), or a pharmaceutically acceptable salt thereof:

(I)

wherein:
A is selected from the group consisting of:
 1) Optionally substituted heteroaryl; and
 2) Optionally substituted aryl;
B is selected from the group consisting of:
 1) Optionally substituted heteroaryl; and
 2) Optionally substituted aryl;
L is —NH—, —NHC(O)—, or —NHC(O)NH—;
X is —CH$_2$—, or —C(O)—;
$R_1$ is selected from the group consisting of:
 1) Optionally substituted heteroaryl; and
 2) Optionally substituted aryl;
$R_2$ is absent or is selected from the group consisting of:
 1) Optionally substituted —C$_1$-C$_8$ alkyl;
 2) Optionally substituted —C$_2$-C$_8$ alkenyl;
 3) Optionally substituted —C$_2$-C$_8$ alkynyl;
 4) Optionally substituted —C$_1$-C$_8$ alkoxy;
 5) Optionally substituted aryloxy;
 6) Optionally substituted —C$_3$-C$_{12}$ cycloalkyl;
 7) Optionally substituted —C$_3$-C$_{12}$ cycloalkenyl;
 8) Optionally substituted 3- to 12-membered heterocycloalkyl;
 9) Optionally substituted aryl;
 10) Optionally substituted arylalkyl;
 11) Optionally substituted heteroaryl;
 12) Optionally substituted heteroarylalkyl;
 13) —NR$_{13}$R$_{14}$;
 14) —CO—NR$_{13}$R$_{14}$; and
 15) —SO$_2$—NR$_{13}$R$_{14}$;

Each R$_3$ is independently selected from halogen, hydroxyl, protected hydroxyl, cyano, amino, protected amino, nitro, optionally substituted —C$_1$-C$_8$ alkyl, optionally substituted —C$_1$-C$_8$ alkoxy, optionally substituted —NHC$_1$-C$_8$ alkyl, optionally substituted —S—(—C$_1$-C$_8$ alkyl), optionally substituted —SO$_2$—(—C$_1$-C$_8$ alkyl), -optionally substituted —SO$_2$—NH—(—C$_1$-C$_8$ alkyl), optionally substituted —NH—SO$_2$—(—C$_1$-C$_8$ alkyl), —CO$_2$R$_{12}$, —NR$_{13}$R$_{14}$, and —CO—NR$_{13}$R$_{14}$;

R$_{12}$ is selected from the group consisting of:
 1) Optionally substituted —C$_1$-C$_8$ alkyl;
 2) Optionally substituted —C$_2$-C$_8$ alkenyl;
 3) Optionally substituted —C$_2$-C$_8$ alkynyl;
 4) Optionally substituted —C$_3$-C$_8$ cycloalkyl;
 5) Optionally substituted —C$_3$-C$_8$ cycloalkenyl;
 6) Optionally substituted 3- to 8-membered heterocycloalkyl;
 7) Optionally substituted aryl; and
 8) Optionally substituted heteroaryl;

R$_{13}$ and R$_{14}$ are each independently selected from hydrogen, optionally substituted —C$_1$-C$_8$-alkyl, optionally substituted —C$_2$-C$_8$-alkenyl, optionally substituted —C$_2$-C$_8$-alkynyl; optionally substituted —C$_3$-C$_8$-cycloalkyl; optionally substituted —C$_3$-C$_8$ cycloalkenyl; optionally substituted 3- to 12-membered heterocycloalkyl, optionally substituted aryl; optionally substituted heteroaryl; optionally substituted —C$_1$-C$_8$-alkoxy, —C(O)R$_{12}$, —S(O)$_2$R$_{12}$, and —S(O)$_2$NHR$_{12}$;

alternatively, R$_{13}$ and R$_{14}$ are taken together with the nitrogen atom to which they are attached to form an optionally substituted heterocyclic ring;

R$_4$ is selected from hydrogen and optionally substituted —C$_1$-C$_8$ alkyl; and n is 0 to k, wherein k is the total number of CH and NH groups in A when A is unsubstituted.

12. The method of claim 11, further comprising administering to the subject a steroid anti-inflammatory compound.

13. The method of claim 11, further comprising the step of administering to the subject an additional anti-RSV agent.

14. The method of claim 11, further comprising administering to the subject an anti-influenza compound.

15. The method of claim 13, wherein the compound and the additional anti-RSV agent are co-formulated.

16. The method of claim 13, wherein the compound and the additional anti-RSV agent are co-administered.

17. The compound of claim 1, represented by Formula (III-2) or a pharmaceutically acceptable salt thereof:

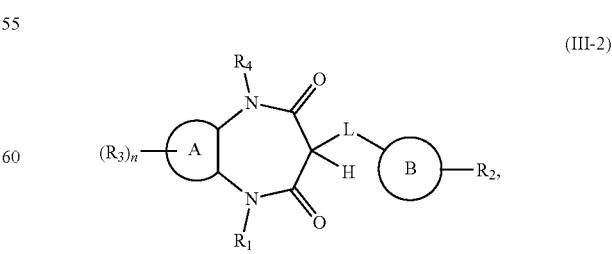

(III-2)

wherein R$_1$, R$_2$, R$_3$, R$_4$, A, B, L, and n are as defined in claim 1.

18. The compound of claim 1, represented by Formula (Ia) or a pharmaceutically acceptable salt thereof:
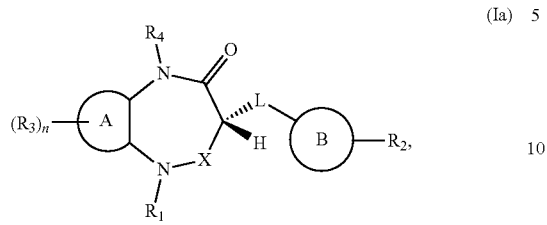
wherein $R_1$, $R_2$, $R_3$, $R_4$, A, B, L, X, and n are as defined in claim 1.
* * * * *